(12) United States Patent
Gu et al.

(10) Patent No.: US 9,108,966 B2
(45) Date of Patent: *Aug. 18, 2015

(54) BETA-LACTAMASE INHIBITORS

(71) Applicant: Cubist Pharmaceuticals, Inc., Lexington, MA (US)

(72) Inventors: Yu Gui Gu, Acton, MA (US); Yong He, Bedford, MA (US); Ning Yin, Lexington, MA (US); Dylan C. Alexander, Watertown, MA (US); Jason B. Cross, Acton, MA (US); Robert Busch, Wakefield, MA (US); Roland E. Dolle, Ashland, MA (US); Chester A. Metcalf, III, Needham, MA (US)

(73) Assignee: Cubist Pharmaceuticals, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/216,476

(22) Filed: Mar. 17, 2014

(65) Prior Publication Data
US 2014/0316133 A1    Oct. 23, 2014

Related U.S. Application Data

(63) Continuation of application No. 13/853,562, filed on Mar. 29, 2013.

(60) Provisional application No. 61/618,119, filed on Mar. 30, 2012, provisional application No. 61/792,672, filed on Mar. 15, 2013.

(51) Int. Cl.
*A61K 31/439* (2006.01)
*A61K 31/546* (2006.01)
(Continued)

(52) U.S. Cl.
CPC ............ *C07D 471/08* (2013.01); *A61K 31/439* (2013.01); *A61K 31/4545* (2013.01); *A61K 31/496* (2013.01); *A61K 31/5377* (2013.01); *A61K 31/546* (2013.01); *A61K 45/06* (2013.01)

(58) Field of Classification Search
CPC ... A61K 31/439; A61K 31/546; C07D 471/08
USPC .......................... 514/300, 203, 202; 546/121
See application file for complete search history.

(56) References Cited

U.S. PATENT DOCUMENTS 8,796,257 B2    8/2014 Maiti et al.
2012/0323010 A1 * 12/2012 Ronsheim et al. ............ 546/121
(Continued)

FOREIGN PATENT DOCUMENTS

WO    WO 2009/091856    *  7/2009
WO    2013149121 A1    10/2013

OTHER PUBLICATIONS

Liang; Tetrahedron Letters, 1996, 37, 6627-6630.*
(Continued)

*Primary Examiner* — John Mabry
*Assistant Examiner* — Daniel Carcanague
(74) *Attorney, Agent, or Firm* — Lathrop & Gage LLP; Brian C. Trinque; David F. Cauble

(57) ABSTRACT

Aryl substituted diazabicyclooctanes (DBO) compounds that inhibit β-lactamases of class A, class C or class D and potentiate β-lactam antibiotics are disclosed. In particular, this disclosure provides DBO compounds that, when used in the disclosed Synergy MIC Assay with a β-lactam antibiotic at a fixed concentration have an MIC of 8 μg/mL or less against one or more isogenic β-lactamase expressing bacterial strains.

3 Claims, 4 Drawing Sheets

(51) Int. Cl.
  C07D 471/08    (2006.01)
  A61K 31/496    (2006.01)
  A61K 31/5377   (2006.01)
  A61K 45/06     (2006.01)
  A61K 31/4545   (2006.01)

(56) References Cited

U.S. PATENT DOCUMENTS

| 2013/0289012 A1* | 10/2013 | Gu et al. | 514/203 |
| 2013/0296290 A1* | 11/2013 | Gu et al. | 514/202 |
| 2013/0296291 A1* | 11/2013 | Gu et al. | 514/202 |
| 2013/0296292 A1* | 11/2013 | Gu et al. | 514/202 |
| 2013/0296293 A1* | 11/2013 | Gu et al. | 514/202 |
| 2013/0296555 A1* | 11/2013 | Gu et al. | 544/127 |
| 2013/0303504 A1* | 11/2013 | Gu et al. | 514/202 |

OTHER PUBLICATIONS

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture-activity relationships in the S-3578 series"; Bioorganic and Medicinal Chemistry 2004, vol. 12, pp. 4211-4219.

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-y1)-2-ethoxyiminoacetamido] cephalosporins bearing 4-[3-(aminoalkyl)-ureido]-1-pyridinium at C-3'"; Bioorganic and Medicinal Chemistry 2004, vol. 12, pp. 4221-4231.

Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure-activity Relationships"; The Journal of Antibiotics 2002, vol. 55, No. 11, pp. 975-992.

Ida, T. et al. "CP6679, a new injectable cephalosporin with broad spectrum and potent activities against methicillin-resistant *Staphylococcus aureus* and *Pseudomonas aeruginosa*"; Journal of Infection and Chemotherapy 2002, vol. 8, pp. 138-144.

\* cited by examiner

Table 1: Compounds of The Invention

| Cmpd. No. | Z | R¹(R¹*) | R(R*) |
|---|---|---|---|
| 101 | R—[isoxazole] | H | —OSO₃H |
| 102 | R—[isoxazole] | -CN | —OSO₃H |
| 103 | R—[isoxazole] | -CONH₂ | —OSO₃H |
| 200 | R—[1,3,4-oxadiazole] | -CH₃ | —OSO₃H |
| 201 | R—[1,3,4-oxadiazole] | -CH₂CH₃ | —OSO₃H |
| 202 | R—[1,3,4-oxadiazole] | -CH₂CH₂OH | —OSO₃H |
| 203 | R—[1,3,4-oxadiazole] | -NHCH₃ | —OSO₃H |
| 204 | R—[1,3,4-oxadiazole] | -[N-methylpiperidin-4-yl] | —OSO₃H |
| 205 | R—[1,3,4-oxadiazole] | -[4-methylpiperazin-1-yl] | —OSO₃H |
| 206 | R—[1,3,4-oxadiazole] | -[morpholin-2-yl] | —OSO₃H |

*Fig. 1A*

Table 1: Compounds of The Invention

| Cmpd. No. | Z | R¹(R¹*) | R(R*) |
|---|---|---|---|
| 207 | R—[1,3,4-oxadiazole] | −N(morpholine) | −OSO$_3$H |
| 300 | R—[1,3,4-thiadiazole] | -H | −OSO$_3$H |
| 301 | R—[1,3,4-thiadiazole] | -CH$_2$NH$_2$ | −OSO$_3$H |
| 302 | R—[1,3,4-thiadiazole] | −N(piperazine)NH | −OSO$_3$H |
| 400 | R—[1,2,4-oxadiazole] | -CH$_3$ | −OSO$_3$H |
| 401 | R—[1,2,4-oxadiazole] | -CONH$_2$ | −OSO$_3$H |
| 402 | R—[1,2,4-oxadiazole] | -CO$_2$Et | −OSO$_3$H |
| 500 | R—[1,2,4-thiadiazole] | -H | −OSO$_3$H |

*Fig. 1B*

Table II: Synergy MIC (sMIC) Against a Panel of Isogenic Strains Expressing β-lactamases (μg/mL)

| β-Lactamase | Species | β-Lactam | CCC | 101 | 102 | 103 | 200 | 201 | 202 | 203 | 204 | 205 | 206 | 207 | 300 | 301 | 302 | 402 | 401 | 400 | 500 |
|---|---|---|---|---|---|---|---|---|---|---|---|---|---|---|---|---|---|---|---|---|---|
| none | E.coli | none | D | F | F | E | F | F | F | F | E | F | F | F | F | F | F | F | F | F | F |
| KPC-2 | E.coli | CXA-101 4 μg/ml | B | A | A | A | B | B | C | B | A | B | A | C | B | A | B | C | B | C | C |
| OXA-15 | E.coli | CXA-101 4 μg/ml | D |  | E |  | C | C | D | B | C | C | C | D | C | C | C |  |  | D | D |
| CTX-M-5 | E.coli | CXA-101 4 μg/ml | A | A | C | B | B | B | C | C | B | B | B | C | A | B | B | B | C | C | C |
| SHV-12 | E.coli | CXA-101 4 μg/ml | B | C | D | B | B | C | C | C | D | C | C | D | B | B | C | B | B | C | C |
| P99 | E.coli | CXA-101 4 μg/ml | A | A | B | B | B | B | B | C | A | B | A | C | A | A | B | C | B | C | A |

A = 0.25-0.5 μg/mL; B = 1-2 μg/mL; C = 4-8 μg/mL; D = 16-32 μg/mL; E = 64-128 μg/mL; F = >128 μg/mL

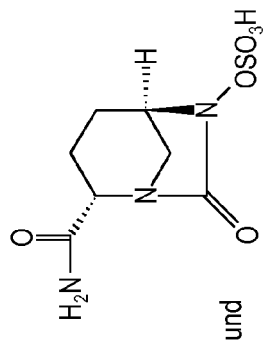

CCC is comparator compound

*Fig. 2*

Table III: Kinetic Assay

| Compound | Kinact/K mM⁻¹s⁻¹ |
|---|---|
| CCC | C |
| 101 | B |
| 102 | A |
| 103 | A |
| 200 | B |
| 201 | B |
| 202 | C |
| 203 | C |
| 204 | B |
| 205 | B |
| 206 | A |
| 207 | B |
| 300 | B |
| 301 | B |
| 302 | B |
| 400 | B |
| 401 | B |
| 402 | B |
| 500 | B |

A = 1000-5000 mM⁻¹s⁻¹; B = 100-999 mM⁻¹s⁻¹; C = 1-99 mM⁻¹s⁻¹

CCC is comparator compound

BETA-LACTAMASE INHIBITORS

RELATED APPLICATIONS

This application claims priority to U.S. Provisional Application No. 61/618,119, filed Mar. 30, 2012, incorporated herein by reference, and U.S. Provisional Application No. 61/792,672, filed Mar. 15, 2013, also incorporated herein by reference. This application is also related to U.S. patent application Ser. Nos. 13/853,443, 13/853,498 and 13/853,506, filed Mar. 29, 2013, the contents of which are incorporated herein by reference in their entirety.

TECHNICAL FIELD

This invention is directed to β-lactamase inhibitors (BLI) or compositions comprising β-lactamase inhibitors.

BACKGROUND

Bacterial resistance to β-lactam antibiotics is most commonly mediated by inactivation by β-lactamases. There is an urgent need for novel BLIs that are effective in inhibiting β-lactamases thus, slowing or preventing the degradation of the β-lactam antibiotic and restoring β-lactam antibiotic susceptibility to β-lactamase producing bacteria.

SUMMARY OF INVENTION

Aryl substituted diazabicyclooctanes (DBO) compounds that potentiate (i.e. make more potent) β-lactam antibiotics are disclosed. In particular, this invention provides DBO compounds that inhibit β-lactamases of class A, C and D, such as KPC-2, CTX-M-15, SHV-12 and P99 AmpC and potentiate a β-lactam antibiotic as evidenced by the Synergy MIC (sMIC) assay described in Example 23. Unexpectedly, many of these compounds are better inhibitors of OXA-15 β-lactamase than previously reported diazabicyclooctanes. These compounds have potential as better inhibitors of the β-lactamase enzyme.

The present invention provides, in one aspect, compounds of chemical Formula (I), or a pharmaceutically acceptable salt thereof wherein the compound of Formula I, when used in the Synergy MIC Assay of Example 23 with an antibiotic selected from CXA-101 (Ceftolozane) or ceftazidime at a fixed concentration of 4 μg/mL, has an MIC of 8 μg/mL or less against one or more isogenic β-lactamase expressing bacterial strains from Table X.

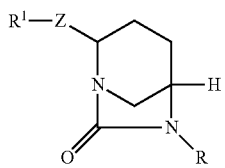
(I)

wherein
Z is a five-membered heteroaryl ring containing from one to four hetero atoms selected from N, O or S;

R is selected from

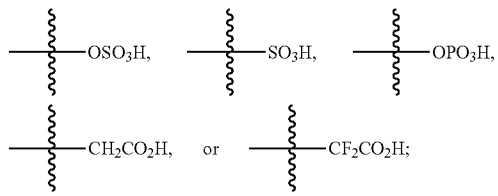

and
$R^1$ is selected from:
a. hydrogen,
b. cyano,
c. ($C_1$-$C_3$)-unsubstituted alkyl,
d. ($C_1$-$C_3$)-alkyl substituted with at least one substituent selected from hydroxyl,

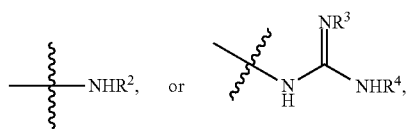

wherein each of $R^2$, $R^3$ and $R^4$ is independently selected from hydrogen, ($C_1$-$C_3$)-alkyl, aminoalkyl, aminocycloalkyl, or hydroxyalkyl, e.

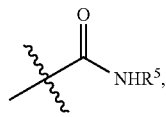

wherein $R^5$ is selected from H or aminoalkyl, f.

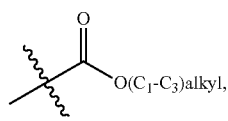

g. amino,
h. ($C_1$-$C_3$)alkylamino, or
i. a 4-6 membered heterocyclyl containing 1-2 heteroatoms selected from O and N, or NX, wherein X is H,

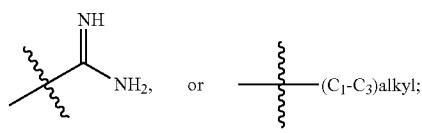

provided that the compound of Formula (I) is not a compound wherein:
(1) Z is imidazol-2-yl, $R^{1*}$ is hydrogen and R* is —OSO$_3$H;
(2) Z is 1,2,4-triazol-5-yl, $R^{1*}$ is methyl and R* is —OSO$_3$H;

(3) Z is 5-oxo-1,3,4-oxadiazol-2-yl, $R^{1*}$ is hydrogen or piperidin-4-yl, and $R^*$ is —$OSO_3H$;
(4) Z is 1,2,3-triazol-4-yl, $R^{1*}$ is methyl and $R^*$ is —$OSO_3H$;
(5) Z is pyrazol-3-yl, $R^{1*}$ is hydrogen or methyl, and $R^*$ is —$OSO_3H$; or
(6) Z is oxazol-2-yl, $R^{1*}$ is hydrogen and $R^*$ is —$OSO_3H$; wherein Table X is:

TABLE X

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQ ID 6 | A | K. pneumoniae | EU784136 |
| CTX-M-15 | pBR-CBST-CTX-M-15 SEQ ID 7 | A | K. pneumoniae | JF775516 |
| SHV-12 | pBR-CBST-SHV-12 SEQ ID 8 | A | K. pneumoniae | AY008838 |
| P99 AmpC | pBR-CBST-P99 AMPC SEQ ID 9 | C | E. cloacea | XO7274 |
| OXA-15 | pBR-CBST-OXA-15 SEQ ID 10 | D | P. aeruginosa | PAU63835 |

In another aspect, the BLIs of the invention can be used in conjunction with a β-lactam antibiotic for evaluating BLIs for treatment in humans.

BRIEF DESCRIPTION OF THE DRAWINGS

FIG. 1A shows Table I, Representative Compounds of The Invention.
FIG. 1B continues Table I.
FIG. 2 shows Table II, the Synergy MIC of representative compounds of Formula I against a panel of isogenic strains expressing β-lactamases.

DETAILED DESCRIPTION

Definitions

Figure 3:
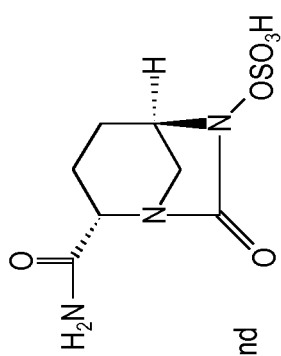
FIG. 3 shows Table III, an assay to determine inhibition kinetics of representative compounds of Formula I for the KPC-2 β-lactamase.

Molecular terms, when used in this application, have their common meaning unless otherwise specified.

The term "alkyl" is defined as a linear or branched, saturated radical having one to about twenty carbon atoms unless otherwise specified. Preferred alkyl radicals are "lower alkyl" radicals having one to about five carbon atoms. Examples of alkyl groups include, without limitation, methyl, ethyl, tert-butyl, isopropyl, and hexyl. A subset of the term alkyl is "$(C_1-C_3)$-unsubstituted alkyl" which is defined as an alkyl group that bears no substituent groups. Examples of $(C_1-C_3)$-unsubstituted alkyl groups include methyl, ethyl, propyl and isopropyl. It is understood that if a $(C_1-C_3)$-alkyl is "substituted" that one or more hydrogen atoms is replaced by a substitutent.

The term amino denotes a $NH_2$ radical

The term "aminoalkyl" denotes an alkyl in which one or more of the alkyl hydrogen atoms has been replaced by an amino group.

The term "aminocycloalkyl" denotes a cycloalkyl in which one of the cycloalkyl hydrogen atoms has been replaced by an amino group.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. Examples of a cycloalkyl group include, without limitation, cyclopropyl, cyclobutyl, cyclohexyl, and cycloheptyl.

The term "heteroaryl" or "heteroaryl ring" denotes an aromatic ring which contain one to four hetero atoms or hetero groups selected from O, N, S. Examples of 5-membered heteroaryl groups include, without limitation, furanyl, thiophenyl, pyrrolyl, oxazolyl, imidazolyl, thidiazolyl, oxadiazolyl, triazolyl and tetrazolyl.

The term "heterocyclyl," "heterocyclic" or "heterocyclyl ring" is defined as a saturated or partially unsaturated ring containing one to four hetero atoms or hetero groups selected from O, N, or NX, wherein X is H,

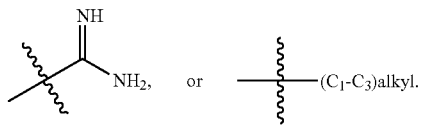

in a single or fused heterocyclic ring system having from three to twelve ring members unless otherwise specified. In a preferred embodiment, a heterocyclyl is a ring system having four to six ring members. Examples of a heterocyclyl group include, without limitation, azetidinyl, morpholinyl, piperazinyl, piperidinyl, and pyrrolidinyl.

The term "hydroxyalkyl" denotes an alkyl in which one or more of the alkyl hydrogen atoms has been replaced by a hydroxyl group.

It will be understood by one of skill in the art that a ┊ or —denote the point of attachment of a substituent group where indicated. For example

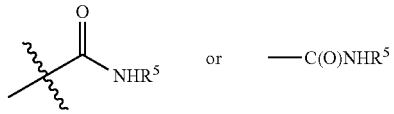

represent that the point of attachment of the amide moiety is at the carbonyl carbon.

The term "therapeutically-effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies. The term "treating" or "treatment" is defined as administering, to a subject, a therapeutically-effective amount of one or more compounds both to prevent the occurrence of an infection and to control or eliminate an infection. Those in need of treatment may include individuals already having a particular medical disease as well as those at risk for the disease (i.e., those who are likely to ultimately acquire the disorder).

The term "subject," as used herein, refers to a mammal, a plant, a lower animal, or a cell culture. In one embodiment, a subject is a human or other animal patient in need of antibacterial treatment.

The term "administering" or "administration" and the like, refers to providing the compound of Formula I to the subject in need of treatment. Preferably the subject is a mammal, more preferably a human.

The functional classification of β-lactamases and terms "class A", "class C", and "class D" β-lactamases are understood by one of skill in the art and are described in "Updated Functional Classification of β-Lactamases", Bush, K.; Jacoby, G. A.; *Antimicrob. Agents Chemother.* 2010, 54, 969-976, herein incorporated by reference.

The salts of the compounds of the invention include acid addition salts and base addition salts. In a one embodiment, the salt is a pharmaceutically acceptable salt of the compound of Formula I. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of optical isomers includes the use of a chiral chromatography column optimally chosen to maximize the separation of the enantiomers. Still another available method involves synthesis of covalent diastereoisomeric molecules by treating compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits detectable (i.e. statistically significant) activity when tested in conventional biological assays such as those described herein.

β-Lactamase Inhibitors (BLIs)

The present invention provides, in one aspect, compounds of chemical Formula (I), or a pharmaceutically acceptable salt thereof wherein the compound of Formula I, when used in the Synergy MIC Assay of Example 23 with an antibiotic selected from ceftolozane or ceftazidime at a fixed concentration of 4 μg/mL, has an MIC of 8 μg/mL or less against one or more isogenic β-lactamase expressing bacterial strains from Table X.

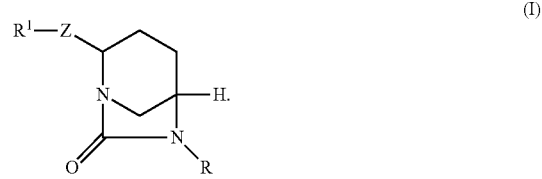

The group Z of Formula I is a five-membered heteroaryl ring containing from one to four hetero atoms selected from N, O and S. In one aspect group Z is a five membered heteroaryl ring containing from one to three heteroatoms selected from N, O, or S.

Substituent R of Formula I is selected from

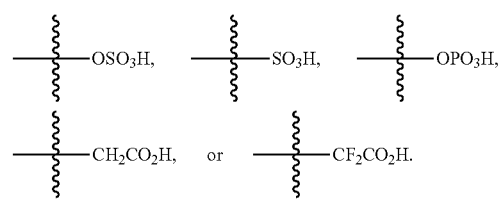

In a preferred embodiment, R is

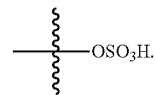

The group R¹ of Formula I is selected from:
a. hydrogen,
b. cyano,
c. ($C_1$-$C_3$)-unsubstituted alkyl,
d. ($C_1$-$C_3$)-alkyl substituted with at least one substituent selected from hydroxyl,

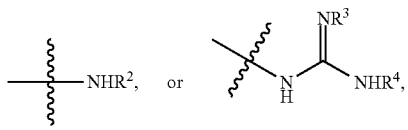

wherein each of $R^2$, $R^3$ and $R^4$ is independently selected from hydrogen, ($C_1$-$C_3$)-alkyl, aminoalkyl, aminocycloalkyl, or hydroxyalkyl,
e.

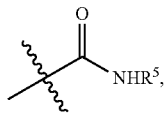

wherein $R^5$ is selected from H or aminoalkyl,
f.

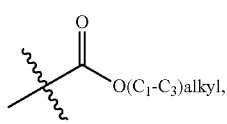

g. amino,
h. ($C_1$-$C_3$)alkylamino, or
i. a 4-6 membered heterocyclyl containing 1-2 heteroatom moieties selected from O and N, or NX, wherein X is H,

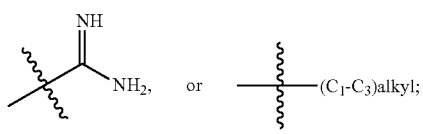

provided that the compound of Formula (I) is not a compound wherein:

(1) Z is imidazol-2-yl, $R^{1*}$ is hydrogen and R* is —$OSO_3H$;
(2) Z is 1,2,4-triazol-5-yl, $R^{1*}$ is methyl and R* is —$OSO_3H$;
(3) Z is 5-oxo-1,3,4-oxadiazol-2-yl, $R^{1*}$ is hydrogen or piperidin-4-yl, and R* is —$OSO_3H$;
(4) Z is 1,2,3-triazol-4-yl, $R^{1*}$ is methyl and R* is —$OSO_3H$;
(5) Z is pyrazol-3-yl, $R^{1*}$ is hydrogen or methyl, and R* is —$OSO_3H$; or
(6) Z is oxazol-2-yl, $R^{1*}$ is hydrogen and R* is —$OSO_3H$.

The isogenic stains are selected from Table X

TABLE X

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQ ID 6 | A | K. pneumoniae | EU784136 |
| CTX-M-15 | pBR-CBST-CTX-M-15 SEQ ID 7 | A | K. pneumoniae | JF775516 |
| SHV-12 | pBR-CBST-SHV-12 SEQ ID 8 | A | K. pneumoniae | AY008838 |
| P99 AmpC | pBR-CBST-P99 AMPC SEQ ID 9 | C | E. cloacea | XO7274 |
| OXA-15 | pBR-CBST-OXA-15 SEQ ID 10 | D | P. aeruginosa | PAU63835 |

In a preferred embodiment of the invention, the compounds of the invention are of the stereochemistry disclosed in Formula II.

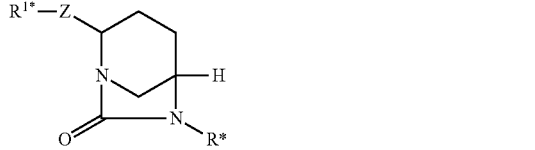

It will be understood by one of skill in the art that depending on the nature of R¹ and R, compounds of Formula I may exist in a salt or zwitterionic form.

Table 1 provides representative compounds of the invention, particularly compounds of Formula II (See FIG. 1).

In another aspect, the invention provides compounds of Formula A-I or pharmaceutically-acceptable salts thereof:

(A-I)

The group Z of Formula A-I is a five-membered heteroaryl ring containing from one to four hetero atoms selected from N, O and S. In one aspect group Z is a five membered heteroaryl ring containing from one to three heteroatoms selected from N, O, or S.

Substituent R* of Formula A-I is selected from

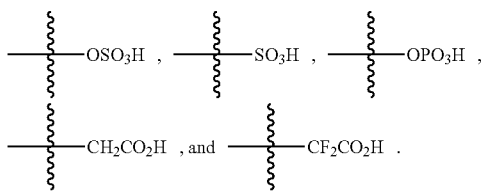

In a preferred embodiment, R* is

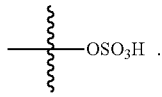

The group $R^{1*}$ of Formula A-I is selected from:
a. hydrogen;
b.

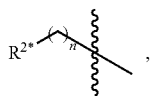

$R^{2*}$ is selected from

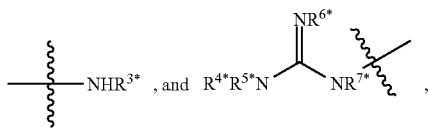

$R^{3*}$ is selected from hydrogen, $(C_1-C_3)$-alkyl, aminoalkyl, aminocycloalkyl, hydroxyalkyl,

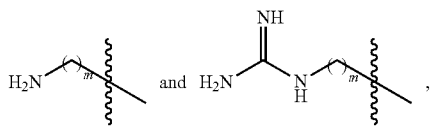

each of $R^{4*}$, $R^{5*}$, $R^{6*}$, and $R^{7*}$ is independently selected from hydrogen or $(C_1-C_6)$-alkyl, aminoalkyl, aminocycloalkyl, and hydroxyalkyl, provided that at least one of $R^{4*}$, $R^{5*}$, $R^{6*}$ and $R^{7*}$ is hydrogen,
n is selected from 1, 2, 3 and 4, and
m is selected from 1, 2 and 3;
c.

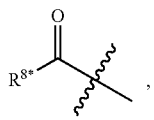

wherein $R^{8*}$ is selected from $NH_2$,

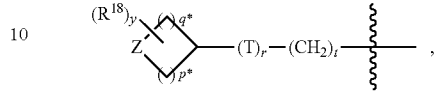

wherein each of $R^{4*}$, $R^{5*}$, $R^{6*}$, and $R^{7*}$ is as described previously and each of $R^9$, $R^{10}$, and $R^{11}$ is independently selected from hydrogen or $(C_1-C_6)$-alkyl, provided that at least one of $R^9$, $R^{10}$, and $R^{11}$ is hydrogen;
d. amino;
e.

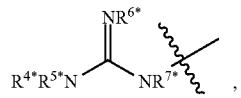

Z is selected from $CR^{12}R^{13}$ or $NR^{14}$,
each of $R^{12}$ and $R^{13}$ is independently selected from H, $NH_2$ and

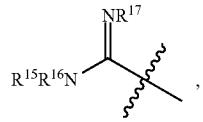

wherein each of $R^{4*}$, $R^{5*}$, $R^{6*}$, and $R^{7*}$, is as described previously,
alternatively, $R^{12}$ and $R^{13}$ together with the carbon to which they are attached, form a cycloalkyl or heterocyclyl ring containing 4-6 ring members,
$R^{14}$ is selected from H and

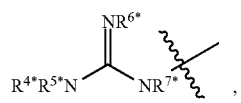

each of $R^{15}$, $R^{16}$ and $R^{17}$ is independently selected from hydrogen, $(C_1-C_6)$-alkyl, aminoalkyl, aminocycloalkyl, and hydroxyalkyl, provided that at least one of $R^{15}$, $R^{16}$ and $R^{17}$ is hydrogen,
$R^{18}$ is selected from $NH_2$ and

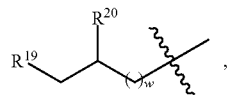

wherein each of $R^{4*}$, $R^{5*}$, $R^{6*}$, and $R^{7*}$ is as described previously,
each of p* and q* is independently selected from 0, 1, 2 and 3,
T is selected from NH and O
t is selected from 0, 1, 2, 3, and 4, and
each of r and y is independently selected from 0 and 1;
f.

wherein $R^{19}$ is selected from $NH_2$ and

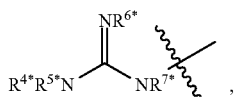

wherein each of $R^{4*}$, $R^{5*}$, $R^{6*}$, and $R^{7*}$ is as described previously,
$R^{20}$ is selected from amino and hydroxyl, and
w is selected from 0 and 1;

g.

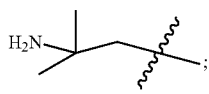

h.

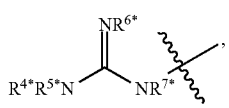

wherein each of $R^{4*}$, $R^{5*}$, $R^{6*}$, and $R^{7*}$ is as described previously;

i.

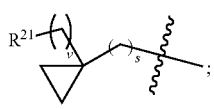

wherein $R^{21}$ is selected from $NH_2$, $-NH(C_1-C_3)$-alkyl and

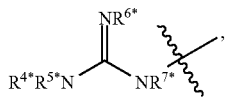

wherein each of $R^{4*}$, $R^{5*}$, $R^{6*}$, and $R^{7*}$ is as described previously,
s selected from 0 and 1, and
v is selected from 0, 1, 2, and 3;

j.

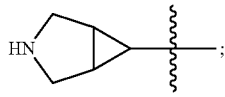

k.

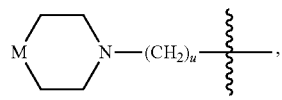

wherein M is selected from $NR^{22}$, $CR^{23}R^{24}$ and O,
wherein $R^{22}$ is H or

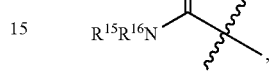

wherein each of $R^{15}$, $R^{16}$, K and $R^{17}$ is as described previously,
each of $R^{23}$ and $R^{24}$ is independently selected from H, $NH_2$ and

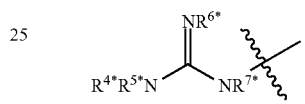

wherein each of $R^{4*}$, $R^{5*}$, $R^{6*}$ and $R^{7*}$ is as described previously, and
u is selected from 0, 1 and 2;

l.

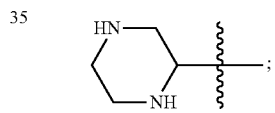

m.

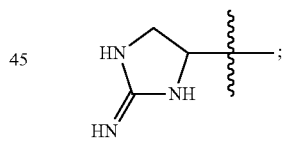

n.

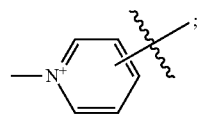

o. $(C_1-C_3)$-unsubstituted alkyl;
p. and

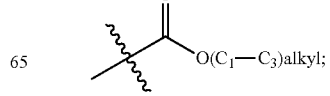

provided that the compound of Formula (A-I) is not a compound wherein:

(1) Z is imidazol-2-yl, $R^{1*}$ is hydrogen and R* is —OSO$_3$H;
(2) Z is 1,2,4-triazol-5-yl, $R^{1*}$ is methyl and R* is —OSO$_3$H;
(3) Z is 5-oxo-1,3,4-oxadiazol-2-yl, $R^{1*}$ is hydrogen or piperidin-4-yl, and R* is —OSO$_3$H;
(4) Z is 1,2,3-triazol-4-yl, $R^{1*}$ is methyl and R* is —OSO$_3$H;
(5) Z is pyrazol-3-yl, $R^{1*}$ is hydrogen or methyl, and R* is —OSO$_3$H; or
(6) Z is oxazol-2-yl, $R^{1*}$ is hydrogen and R* is —OSO$_3$H.

Use of the Compounds of Formulas I, A-I and II

In one aspect of the invention the compounds of Formulas I, A-I and II are effective in inhibiting β-lactamases expressed by isogenic strains. In one aspect of the invention, the β-lactamases are selected from class A, class C or class D β-lactamases. Class A β-lactamases for example, include, but are not limited to, TEM, SHV, CTX-M, KPC, GES, VEB, SME, and GEX. In a preferred aspect of the invention, the compounds of the invention inhibit KPC β-lactamases. More preferably the compounds of the invention inhibit KPC-2 or KPC-3 β-lactamases. Class C β-lactamases for example, include, but are not limited to chromosomal AmpCs, and plasmid based ACC, DHA, CMY, FOX, ACT, MIR, LAT, MOX β-lactamases. Class D β-lactamase enzymes are OXA β-lactamases.

In one aspect of the invention, the β-lactamases expressed by isogenic strains are selected from KPC, CTX-M, SHV, OXA or AmpC β-lactamases. In another aspect of the invention, the isogenic strains that express β-lactamases are prepared according to the method described in Example 22. In another aspect of the invention the isogenic strains are those described in Table X.

Unless otherwise indicated, the activity of the BLI compounds can be described by the MIC value obtained from a Synergy MIC assay (e.g. as described herein). The lower the sMIC value the more active the BLI, regardless of the mechanism of action of the BLI compound (e.g., including inhibition of β-lactamases by the BLI or any other mechanism of action or combination of mechanisms of action). The sMIC data supports that the compounds of Formulas I, A-I and II potentiate (i.e. make more potent) the activity of the β-lactam antibiotic against beta-lactamase producing strains by inhibiting the β-lactamase.

In one aspect of the invention, the BLI activity is measured by the Synergy MIC Assay described in Example 23 as the sMIC. The sMIC gives the value required for the BLI to potentiate the activity of 4 μg/mL of CXA-101 (Ceftolozane) or ceftazidime to inhibit the growth of β-lactamase producing bacteria. Growth is defined as turbidity that could be detected with the naked eye or achieving minimum OD600 of 0.1. sMIC values were defined as the lowest concentration producing no visible turbidity.

Preferably, the Synergy MIC is 8 μg/mL or less. In a more preferred aspect of the invention, the Synergy MIC is 4 to 8 μg/mL. In an even more preferred aspect of the invention, the Synergy MIC is 1 to 2 μg/mL. In a still more preferred aspect of the invention, the Synergy MIC is 0.2 to 0.5 μg/mL. Synergy MICs for representative compounds of the invention are described in Table II (See FIG. 2). It will be understood by one of skill in the art that the growth inhibition of the isogenic β-lactamase producing strains can also be measured by a checkerboard synergy assay like that disclosed in International Patent Application Number WO 2008039420 or a standard BLI potentiation assay using a fixed concentration of BLI.

The compounds of the present invention have a broad spectrum of activity across a wide variety of β-lactamase producing bacteria. It was surprisingly found that the compounds of the present invention are active in potentiating activity of β-lactam antibiotics, in particular, Ceftolozane, against strains expressing class D β-lactamases, in particular the OXA-15 β-lactamase. Currently marketed BLIs inhibit most of the class A β-lactamases, but poorly inhibit class A KPC and class C β-lactamases and have variable success in inhibiting penicillinase and carbapenemase-type class D β-lactamases. The compounds of the present invention are active against bacterial strains that express class A and C β-lactamases and also, surprisingly are active against bacterial strains that express the class D cephalosporinase OXA-15 (Tables II). This increased activity against the class D β-lactamase is critical because differential effectiveness against different types of β-lactamase producing bacteria is necessary in order to effectively use β-lactam antibiotics to treat resistant strains of bacteria (vide infra).

In one embodiment, the compounds of Formulas I, A-I and II are as active, or more active against bacterial strains that express KPC β-lactamase than the most structurally similar compound Avibactam (comparator compound CCC). Compounds that are as active or more active than Avibactam are, for example, compounds 101, 102, 103, 200, 201, 203, 204, 205, 206, 300, 301, 302 and 401.

In one embodiment, the compounds of Formulas I, A-I and II are as active against bacterial strains that express CTX-M-15 β-lactamase than the most structurally similar compound Avibactam (comparator compound CCC). Compounds that are as active as Avibactam are, for example, compounds 101, and 300.

In one embodiment, the compounds of Formulas I, A-I and II are as active against bacterial strains that express SHV-12 β-lactamase than the most structurally similar compound Avibactam (comparator compound CCC). Compounds that are as active as Avibactam are, for example, compounds 103, 200, 300, 301, 302, 401, and 402.

In one embodiment, the compounds of Formulas I, A-I and II are as active against bacterial strains that express P99 β-lactamase than the most structurally similar compound Avibactam (comparator compound CCC). Compounds that are as active as Avibactam are, for example, compounds 101, 204, 206, 300, 301, and 500.

In one embodiment, the compounds of Formulas I, A-I and II are unexpectedly more active against bacterial strains that express OXA-15 β-lactamase than the most structurally similar compound Avibactam (comparator compound CCC). Compounds that are more active than Avibactam are, for example, compounds 200, 201, 204, 205, 206, 300, 301, and 302.

In another embodiment, the compounds of Formulas I, A-I and II have high binding affinity for the β-lactamase enzyme. Consequently these compounds are better inhibitors of the β-lactamase enzyme. The inhibition kinetics of the compounds of Formulas I, A-I and II was measured according to the procedure outlined in Example 24. The compounds of Formulas I, A-I and II have a high binding affinity for the β-lactamase enzyme.

In one embodiment the compounds of Formulas I, A-I and II have a binding affinity of 1000-5000 $mM^{-1}s^{-1}$. Compounds that have a binding affinity of 1000-5000 $mM^{-1}s^{-1}$ are, for example, compounds 102 and 103 (Table III).

In one embodiment the compounds of Formulas I, A-I and II have a binding affinity of 100-999 $mM^{-1}s^{-1}$. Compounds that have a binding affinity of 100-999 $mM^{-1}s^{-1}$ are, for example, compounds 101, 200, 201, 204, 205, 206, 300, 301, 302, 400, 401, 402, and 500 (Table III).

In one embodiment the compounds of Formulas I, A-I and II have a binding affinity of 1-99 $mM^{-1}s^{-1}$. Compounds that have a binding affinity of 1-99 $mM^{-1}s^{-1}$ are, for example, compounds 202 and 203 (Table III).

It was surprisingly found that the compounds of the present invention have a higher binding affinity for the β-lactamase enzyme than the closest structural comparator Avibactam. (Table III, See FIG. 3)

In another aspect, the compounds of the present invention are useful in evaluating BLIs for treatment in humans. Compounds of Formulas I, A-I and II when used in the Synergy MIC Assay of Example 23 with an antibiotic selected from ceftolozane or ceftazidime at a fixed concentration of 4 μg/mL, that have a sMIC value of 8 μg/mL or less against at least one isogenic β-lactamase expressing strain of Table X are useful candidates for human treatment against β-lactamase producing bacteria Inhibition of β-lactamases with BLIs slows or prevents degradation of β-lactam antibiotics and restores β-lactam antibiotic susceptibility to β-lactamase producing bacteria. Thus these compounds in conjunction with a β-lactam antibiotic are useful in treating bacterial infections in humans caused or exacerbated by β-lactamase producing bacteria.

In one aspect of the invention, the bacterial infection is caused by class A, class C or class D β-lactamase producing bacteria.

Representative Gram-negative pathogens known to express β-lactamases include, but are not limited to *Acinetobacter* spp. (including *Acinetobacter baumannii*), *Citrobacter* spp., *Escherichia* spp. (including *Escherichia coli*), *Haemophilus influenzae*, *Morganella morganii*, *Pseudomonas aeruginosa*, *Klebsiella* spp. (including *Klebsiella pneumoniae*), *Enterobacter* spp. (including *Enterobacter cloacae* and *Enterobacter aerogenes*), *Pasteurella* spp., *Proteus* spp. (including *Proteus mirabilis*), *Serratia* spp. (including *Serratia marcescens*), and *Providencia* spp. Bacterial infections can be caused or exacerbated by Gram-negative bacteria including strains which express β-lactamases that may confer resistance to penicillins, cephalosporins, monobactams and/or carbapenems. The co-administration of a novel BLI that inhibits these β-lactamases with a β-lactam antibiotic could be used to treat infections caused β-lactam resistant bacteria.

β-Lactam antibiotics that may be co-administered with compounds of Formula I include, but are not limited to cephalosporins (e.g. Ceftolozane), carbapenem (e.g. Meropenem), monobactam (e.g. Aztreonam), and penicillin (e.g. Piperacillin) classes of antibiotics.

Another object of the invention is pharmaceutical compositions or formulations comprising compounds of Formulas I, A-I and II, or salts thereof, preferably further comprising a β-lactam antibiotic.

The pharmaceutical compositions can be formulated for oral, intravenous, intramuscular, subcutaneous or parenteral administration for the therapeutic or prophylactic treatment of diseases, such as bacterial infections. Preferably, the pharmaceutical composition is formulated for intravenous administration. The pharmaceutical compositions can comprise one or more of the compounds disclosed herein, preferably a compound of Formula I, A-I or II in conjunction with a β-lactam antibiotic, in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art and includes tablet binders, lubricants, flavoring agents, preservatives, wetting agents, emulsifying agents, and dispersing agents. Compounds of the present invention preferably a compound of Formula I, A-I or II in conjunction with a β-lactam antibiotic, can be, for example:

1. in the form of tablets, capsules, elixirs, suspensions, syrups, wafers, pills powders, granules and the like,
2. dissolved or suspended in any of the commonly used intravenous fluids (e.g. physiological saline or Ringer's solution) and administered by infusion,
3. in the form of aqueous or non-aqueous solutions, dispersions, suspensions or emulsions as well as sterile powders for reconstitution into sterile injectable solutions or dispersions just prior to use,
4. in the form of microencapsulating matrices of the drug in biodegradable polymers such as polylactide-polyglycolide,
5. dissolved and administered in a pharmaceutical diluent such as Water-for-Injection (WFI), physiological saline or 5% glucose,
6. in liquid or semi-liquid form formulated in hydrophobic or hydrophilic bases as ointments, creams, lotions, paints or powders,
7. in the form of suppositories admixed with conventional carriers such as cocoa butter, polyethylene glycol or a suppository wax or other glyceride that are solid at room temperature but liquid at body temperature,
8. in powder form for reconstitution in the appropriate pharmaceutically acceptable carrier at the time of delivery.

In one embodiment of the invention, is provided a method of treating or preventing a bacterial infection comprising administering to a subject in need thereof a therapeutically-effective amount of the pharmaceutical composition comprising a compound of Formula I and a β-lactam antibiotic.

In one embodiment of the invention, is provided a method of treating or preventing a bacterial infection comprising administering to a subject in need thereof, a therapeutically-effective amount of a β-lactam antibiotic in conjunction with a compound of Formula I, A-I or II.

In one embodiment of the invention, is provided a method of treating or preventing a bacterial infection in a subject comprising the steps of
a. administering to the subject a compound of Formula I, A-I or II; and
b. administering to a subject a therapeutically-effective amount of a β-lactam antibiotic.

In one embodiment of the invention, is provided a method of treating or preventing a bacterial infection in a subject comprising the steps of
a. administering to a subject a therapeutically-effective amount of a β-lactam antibiotic; and
b. administering to the subject a compound of Formula I, A-I or II.

The pharmaceutical compositions, preferably a compound of Formula I, A-I or II in conjunction with a β-lactam antibiotic, can be used to treat a bacterial infection of any organ or tissue in the body caused by β-lactam resistant bacteria, preferably, Gram-negative β-lactam resistant bacteria.

Actual dosage levels of active ingredients in the pharmaceutical compositions of one or more compounds according to Formula I, A-I or II, preferably a compound of Formula I, A-I or II in conjunction with a β-lactam antibiotic, may be varied so as to obtain a therapeutically-effective amount of the active compound(s) to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans. It will be understood by one of skill in the art that when the composition comprises a compound of Formula I, A-I or II and a β-lactam antibiotic, both the compound of Formula I, A-I or II and the β-lactam antibiotic are active compounds.

The method comprises administering to the subject an effective dose of one or more compounds of Formula I, A-I or II, preferably in conjunction with a β lactam antibiotic. An effective dose of a compound of Formula I, A-I or II is generally between 125 mg/day to 2000 mg/day.

In one embodiment, a β-lactam antibiotic and a compound of Formula I, A-I or II are administered in ratio of 1:4 to 8:1 antibiotic:Formula I, A-I or II compound. In one embodiment the ratio is 1:4. In another embodiment the ratio is 3:4. In another embodiment the ratio is 5:4. In another embodiment the ratio is 7:4. In another embodiment the ratio is 1:2. In another embodiment the ratio is 3:2. In another embodiment the ratio is 5:2. In another embodiment the ratio is 7:2. In another embodiment the ratio is 1:3. In another embodiment the ratio is 2:3. In another embodiment the ratio is 4:3. In another embodiment the ratio is 5:3. In another embodiment the ratio is 7:3. In another embodiment the ratio is 1:2. In another embodiment the ratio is 3:2. In another embodiment the ratio is 5:2. In another embodiment the ratio is 7:2. In another embodiment the ratio is 1:1. In another embodiment the ratio is 2:1. In another embodiment the ratio is 3:1. In another embodiment the ratio is 4:1. In another embodiment the ratio is 5:1. In another embodiment the ratio is 6:1. In another embodiment the ratio is 7:1. In another embodiment the ratio is 8:1. It will be understood by one of skill in the art that the β-lactam antibiotic and compound of Formula I, A-I or II can be administered within the range of ratios provided regardless of the method of drug delivery. It will also be understood by one of skill in the art that the β-lactam antibiotic and compound of Formula I, A-I or II can be administered within the range of ratios provided together, for example, in a pharmaceutical composition, or sequentially, i.e. the β-lactam antibiotic is administered, followed by administration of a compound of Formula I, A-I or II or vice versa.

One or more compounds of Formulas I, A-I and II, preferably a compound of Formula I, A-I or II in conjunction with a β-lactam antibiotic, can be administered as a single daily dose or in multiple doses per day.

One or more compounds of Formulas I, A-I and II, preferably a compound of Formula I, A-I or II in conjunction with a β-lactam antibiotic, may be administered according to this method until the bacterial infection is eradicated or reduced.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Preparation of Compounds of Formulas I, A-I and II

A compound of Formulas I, A-I and II can be prepared by a variety of synthetic routes, including synthetic schemes described herein. These synthetic routes can be applied to large scale synthesis with appropriate adjustment of reaction sequence, reaction conditions, isolation/purification methods and choice of solvents which are environmentally friendly and cost-effective.

The following abbreviations have the following meanings unless otherwise indicated. Abbreviations not defined below have their generally accepted meaning.

Bn=benzyl
Boc=tert-butoxycarbonyl
Boc$_2$O=di-tert-butyldicarbonate
Burgess reagent=methyl N-triethylammoniumsulfonyl) carbamate
CDI=carbonyldiimidazole
CFU=colony-forming units
CLSI=Clinical Laboratory Standards Institute
cSSSI=complicated skin and skin structure infections
DBU=1,8-diazabicyclo[5.4.0]undec-7-ene
DCM=dichloromethane
DEAD=diethyl azodicarboxylate
DIAD=diisopropyl azodicarboxylate
DIPEA=diisopropylethylamine
DMF=N,N-dimethylformamide
DMAc=N,N-dimethylacetamide
DMSO=dimethyl sulfoxide
EDCI=1-ethyl-3-(3'-dimethylaminopropyl)carbodiimide
ELSD=evaporative light scattering detector
EtOAc=ethyl acetate
ESI-MS=electrospray ionization mass spectrometry
Fmoc=Fluorenylmethyloxycarbonyl
HAP=Hospital-Acquired Pneumonia
HATU=2-(7-aza-1H-benzotriazole-1-yl)-1,1,3,3-tetramethyluronium hexafluorophosphate
HCl=hydrochloride
HOBt=1-hydroxybenzotrizole
Hrs=hours
HPLC=high performance liquid chromatography
Hunig's base=N,N-Diisopropylethylamine
Lawesson's reagent=2,4-bis(4-methoxyphenyl)-1,3,2,4-dithiadiphosphetane-2,4-disulfide
MIC=minimum inhibitory concentration
mL=milliliter
MS=mass spectrometry
MRSA=methicillin-resistant *Staphylococcus aureus*
NMR=nuclear magnetic resonance
Ns=nitrobenzenesulfonyl
Pa=*Pseudomonas aeruginosa*
Prep=preparative
Ppm=parts per million
sat.=saturated
rt=room temperature
TBAF=tetrabutylammonium fluoride
TBS=t-butyldimethylsilyl
TES=triethylsilyl
TEA=triethylamine
TEMPO=2,2,6,6-tetramethyl-1-piperidinyloxy, free radical
THF=tetrahydrofuran
TFA=trifluoroacetic acid
TMS=trimethylsilyl
TLC=thin layer chromatography
VAP=Ventilator-Associated Pneumonia The compounds of Formulas I, A-I and II can be prepared from intermediates 1 or 7, according to the following reaction schemes and examples, or modifications thereof, using readily available starting materials, reagents and conventional synthetic procedures including, for example, procedures described in U.S. Pat. No. 7,112,592 and WO2009091856. As depicted in Scheme 1, compound 3 can be synthesized following standard heterocyclic ring formation chemistry under appropriate reaction conditions from ester intermediate 1, or its corresponding derivatives, such as carboxylic acid derivative 2a and aldehyde derivative 2b (see, e.g., Walker, D. G.; Brodfuehrer, P. R.; Brundidge, S. P. Shih, K. M.; Sapino, C. Jr. *J. Org. Chem.* 1988, 53, 983-991 and references cited therein, hereafter Walker). Appropriate functional group protections for the R group are needed when necessary Scheme 1

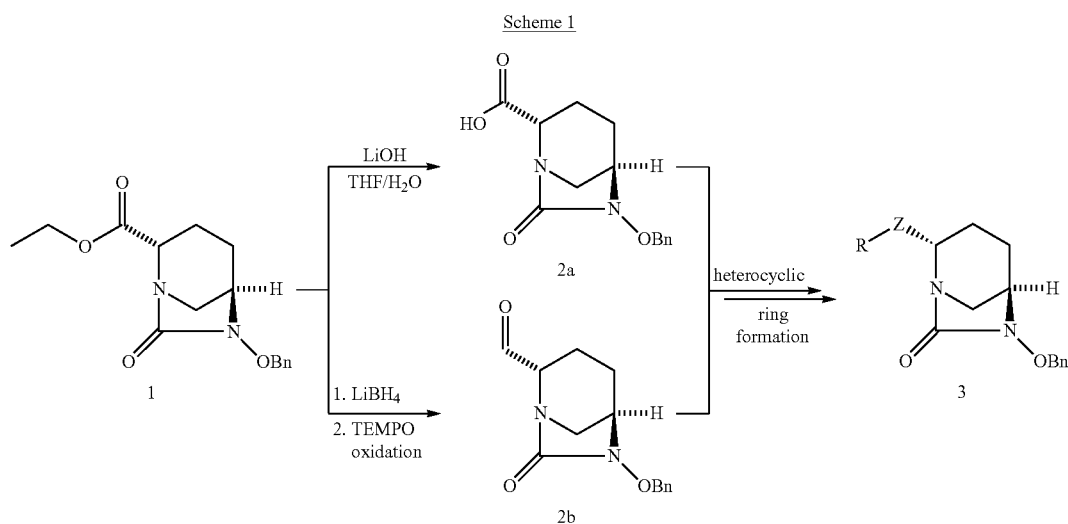

Alternatively, compound 3 can be synthesized from intermediate 7 as shown in Scheme 2. Monocyclic ester intermediate 7 can be converted to 8 under standard Mitsunobu reaction conditions. Compound 9 can then be prepared following standard heterocyclic ring formation chemistry under appropriate reaction conditions from ester intermediate 8, or its corresponding derivatives (see, e.g., Walker.

It may be necessary to protect certain functionalities in the molecule depending on the nature of the $R^1$ group. Protecting these functionalities should be within the expertise of one skilled in the art. See, e.g. P. G. M. Wuts and T. W. Greene, *Protective Groups in Organic Synthesis*, Fourth Edition, John Wiley and Sons, 2006, hereafter Greene.

Deprotection of the N-Ns group in compound 9 provides compound 10, which can be converted to compound 11 by treatment with diphosgene. Compound 3 can be obtained upon deprotection of the N-Boc group from compound 11 under appropriate conditions, such as 4M HCl in dioxane, and subsequent treatment with base, such as $NEt_3$. Alternatively, deprotection of the N-Boc and N-Ns groups in compound 11 under appropriate conditions provides bis-amine derivative 12, which can then be cyclized to form compound 3 by treatment with diphosgene or triphogene, under appropriate conditions.

Scheme 2

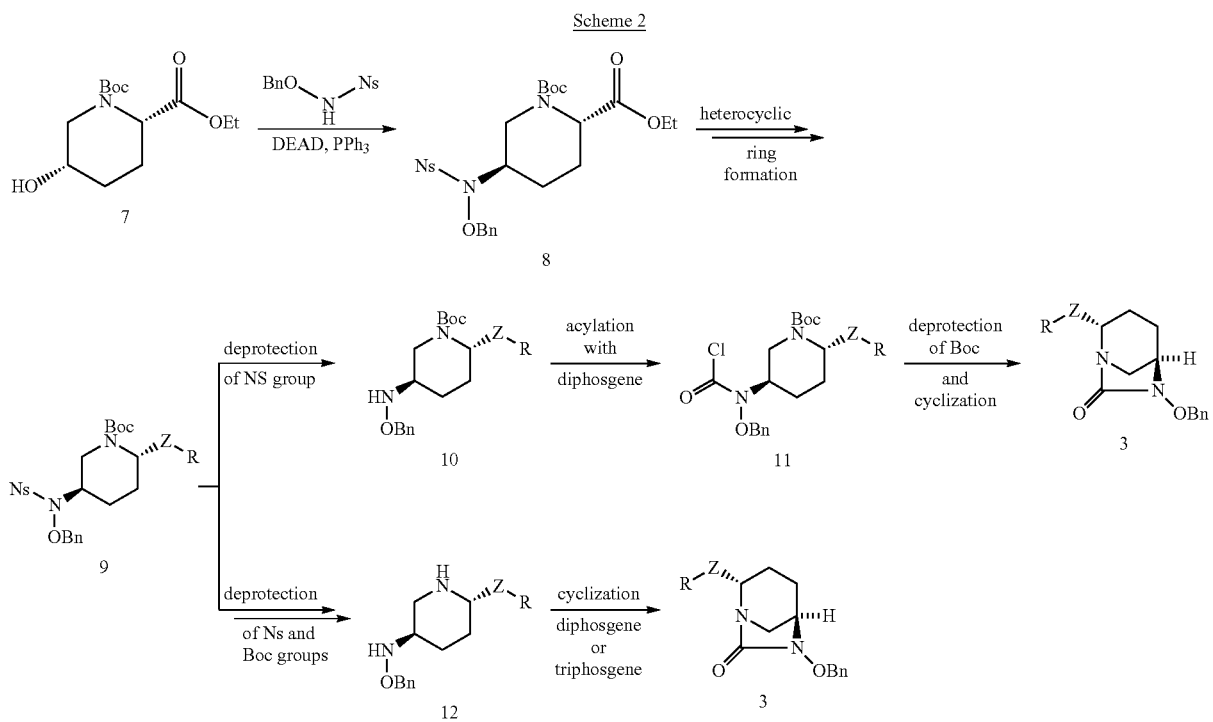

The benzylic ether protecting group in 3 can be removed via standard hydrogenolysis conditions, such as, but not limited to, Pd/H$_2$ in MeOH or THF or by acid-catalysed hydrolysis, such as, but not limited to, BCl$_3$ in DCM to provide the hydroxy-urea intermediate 4, which can be used directly in the next step without further purification. Sulfation of 4 can be achieved by treatment with a sulfating reagent, such a, but not limited to, SO$_3$.pyridine complex, in an appropriate solvent, such as pyridine, DMF or DMAC at a temperature of 0-80° C., preferable at room temperature. Compound 5 can then be isolated and purified via conventional methods. For example, 5 can be purified by standard reverse phase prep-HPLC using an appropriate buffer system, i.e. ammonium formate buffer. In some cases, 5 can be purified by normal phase silica gel chromatography after converting to an appropriate salt form, such as sulfate tetrabutyl ammonium salt. The tetrabutyl ammonium salt can be converted to a sodium salt by cation exchange. When protecting group(s) are present in the sidechain (i.e. Boc or Fmoc for amine and guanidine protection, TBS or TES for alcohol protection, etc), a deprotection step is needed to convert 5 to its final product 6, which can be purified by reverse phase prep-HPLC using the conditions mentioned above. For example, for N-Boc deprotection, 5 can be treated with an acid, such as TFA, in an appropriate solvent, such as DCM at a temperature of 0-30° C., preferable at 0° C. to rt to give 6. For an O-TBS, or O-TES deprotection, a fluoride reagent such as HF.pyridine, HF.NEt$_3$, or TBAF can be used. For an Fmoc deprotection, amines, such as diethylamine, DBU, piperidine, etc can be used.

adopted to variations in order to produce compounds of Formulas I, A-I and II, but not otherwise specifically disclosed. Further, the invention includes variations of the methods described herein to produce the compounds of Formulas I, A-I and II that would be understood by one skilled in the art based on the instant invention.

All temperatures are understood to be in Centigrade (C) when not specified. The nuclear magnetic resonance (NMR) spectral characteristics refer to chemical shifts (γ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-d6 (perdeuterodimethysulfoxide), D$_2$O (deuterated water), CDCl$_3$ (deuterochloroform) and other conventional deuterated solvents. The prep-HPLC conditions are: Waters SunFire® C18 (30×100 mm, 5 μm OBD) column; flow rate: 30-80 mL/minutes, ELSD or Mass-triggered fraction collection; sample loading: Each injection loading varied from 30-300 mg for different crude samples depending on their solubility and purity profiles; Solvent system using ammonium formate buffer: solvent A: water with 20 mM ammonium formate, solvent B: 85% of acetonitrile in water with 20 mM ammonium formate. Solvent system using NH$_4$HCO$_3$ buffer: solvent A: water with 10 mM NH$_4$HCO$_3$, solvent B: acetonitrile. Solvent system using NH$_4$OH buffer: solvent A: water with 0.1% NH$_4$OH, solvent B: acetonitrile with 0.1% NH$_4$OH.

Example 1

Synthesis of (2S,5R)-ethyl 6-(benzyloxy)-7-oxo-1,6-diazabicyclo[3.2.1]octane-2-carboxylate (Intermediate Compound 1)

Scheme 3

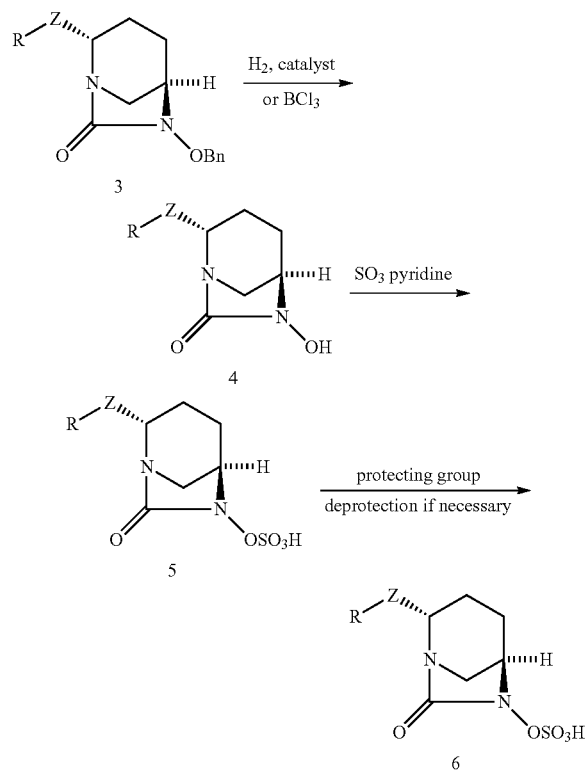

EXAMPLES

The specific examples which follow illustrate the synthesis of certain compounds. The methods disclosed may be

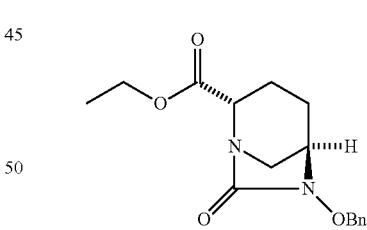

Step 1: Synthesis of (S)-1-tert-butyl 2-ethyl 5-oxopiperidine-1,2-dicarboxylate

Method A:

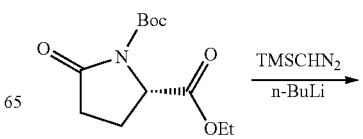

-continued

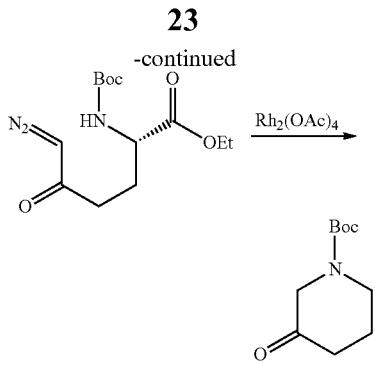

n-BuLi was added dropwise to a solution of TMSCHN$_2$ (690 mL, 1.38 mol) in dry THF (3 L) (600 mL, 1.5 mol) at −78° C., and the mixture was stirred at −78° C. for 30 min. The mixture was then transferred to a solution of (S)-1-tert-butyl 2-ethyl 5-oxopyrrolidine-1,2-dicarboxylate (300 g, 1.17 mol) in dry THF (3 L) via cannula, and the mixture was stirred at −78° C. for 30 mM The reaction mixture was then quenched with sat. NH$_4$Cl solution, and extracted with DCM three times. The combined organic layer was concentrated in vacuum and the crude product was purified by silica gel column chromatography (3:1 petroleum ether:EtOAc) to afford (S)-ethyl 2-((tert-butoxycarbonyl)amino)-6-diazo-5-oxohexanoate (262 g, 75%) as a yellow solid.

A solution of (S)-ethyl 2-((tert-butoxycarbonyl)amino)-6-diazo-5-oxohexanoate (350 g, 1.18 mol) in DCM (1500 mL) was added to a solution of Rh$_2$(OAc)$_4$ (3.5 g, 7.9 mmol) in DCM (750 mL) at 0° C. The reaction was then stirred at 20° C. overnight and then concentrated in vacuum. The crude sample was purified by silica gel column chromatography (5:1 petroleum ether/EtOAc) to afford (S)-1-tert-butyl 2-ethyl 5-oxopiperidine-1,2-dicarboxylate (175.9 g, 55%) as a yellow oil.

Method B:

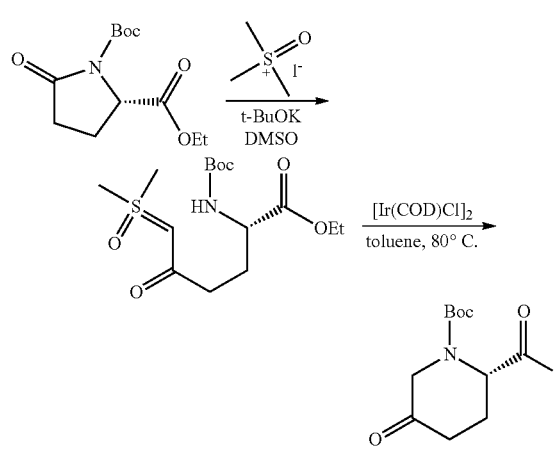

t-BuOK (330 g, 2.9 mol) was added to a solution of trimethylsulfoxonium iodide (750 g, 3.5 mol) in dry DMSO (3 L) and the mixture was stirred at rt for 1 h. (S)-1-tert-Butyl 2-ethyl 5-oxopyrrolidine-1,2-dicarboxylate (900 g, 3.5 mol) was added and the mixture was stirred at rt for 2-3 hrs. Water was added to quench the reaction and the mixture was extracted with EtOAc 5 times. The combined organic layer was concentrated in vacuum and the crude sample was purified by silica gel column chromatography (1:1 petroleum ether/EtOAc then 1:10 MeOH/DCM) to afford sulfoxonium ylide intermediate (977 g, 80%) as a white solid.

A solution of sulfoxonium ylide intermediate (156 g, 0.446 mol) and [Ir(COD)Cl]$_2$ (3 g, 4.46 mmol) in toluene (4 L) was degassed by bubbling nitrogen through the solution for 10 minutes. The reaction mixture was heated to 80-90° C. for 2-3 hrs and then cooled to 20° C. Then toluene was concentrated in vacuum, the residue was purified by silica gel column chromatography (10:1 to 3:1 gradient petroleum ether/EtOAc) to afford (S)-1-tert-butyl 2-ethyl 5-oxopiperidine-1,2-dicarboxylate (140 g, 57.8%) as a yellow oil.

Step 2: Synthesis of (2S,5S)-1-tert-butyl 2-ethyl 5-hydroxypiperidine-1,2-dicarboxylate

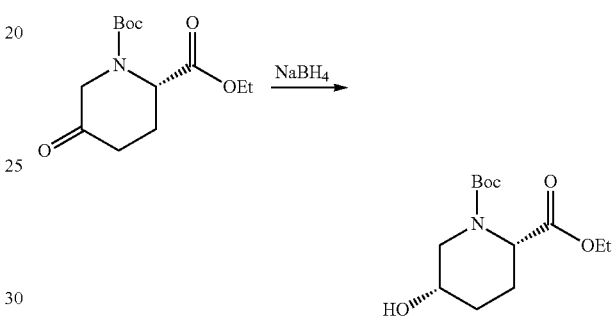

NaBH$_4$ (36 g, 1.0 mol) was added in portions to a solution of (S)-1-tert-butyl 2-ethyl 5-oxopiperidine-1,2-dicarboxylate (250 g, 0.92 mol) in EtOH (1500 mL) at −40° C. The reaction mixture was then stirred at −40° C. for 0.5 hr then quenched with 10% HOAc solution. After diluting with water, the mixture was extracted with DCM three times. The combined organic layer was concentrated in vacuum and purified by silica gel column chromatography (1:1 petroleum ether/EtOAc) to afford (2S,5S)-1-tert-butyl 2-ethyl 5-hydroxypiperidine-1,2-dicarboxylate (205 g, 80%) as a yellow oil.

Step 3: Synthesis of (2S,5R)-1-tert-butyl 2-ethyl 5-(N-(benzyloxy)-2-nitrophenylsulfonamido)piperidine-1,2-dicarboxylate

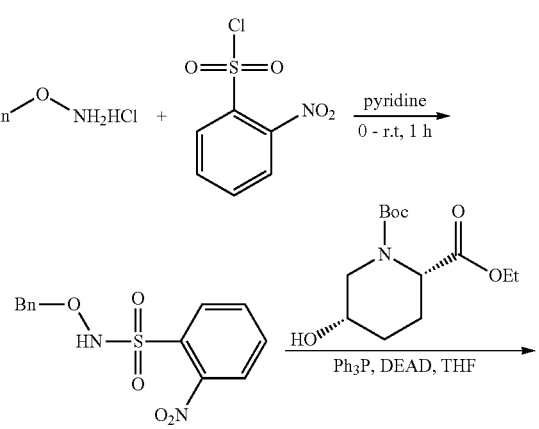

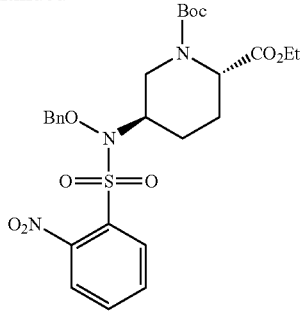

A solution of 2-nitrobenzene-1-sulfonyl chloride (500 g, 2.26 mol) in pyridine (1500 mL) was added dropwise to a solution of O-benzylhydroxylamine hydrochloride (400 g, 2.51 mol) in pyridine (1500 mL) at 0° C. The reaction mixture was then stirred at 20° C. overnight. The mixture was concentrated in vacuum, diluted with DCM and washed with HCl (10%) three times. The combined organic layer was concentrated in vacuum and re-crystallized with DCM to afford N-(benzyloxy)-2-nitrobenzenesulfonamide (485 g, 62.6%) as a yellow solid.

To a solution of N-(benzyloxy)-2-nitrobenzenesulfonamide (212 g, 0.69 mol) in THF (1000 mL) was added (2S, 5S)-1-tert-butyl 2-ethyl 5-hydroxypiperidine-1,2-dicarboxylate (171 g, 0.63 mol) and PPh$_3$ (275 g, 1.05 mol), followed by dropwise addition of a solution of DEAD (195 g, 1.12 mol) in THF (500 mL). The mixture was then stirred at 20° C. overnight. The reaction mixture was then concentrated in vacuum and purified by silica gel column chromatography (3:1 petroleum ether/EtOAc) to afford (2S,5R)-1-tert-butyl 2-ethyl 5-(N-(benzyloxy)-2-nitrophenylsulfonamido)piperidine-1,2-dicarboxylate (283.8 g, 80%) as a yellow oil.

Step 4: Synthesis of (2S,5R)-1-tert-butyl 2-ethyl 5-((benzyloxy)amino)piperidine-1,2-dicarboxylate

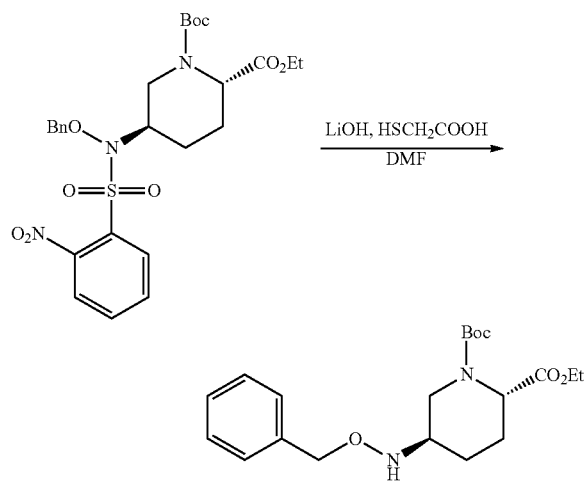

LiOH.H$_2$O (95 g, 2.3 mol) and 2-mercaptoacetic acid (124 g, 1.3 mol) were added to a solution of (2S,5R)-1-tert-butyl 2-ethyl 5-(N-(benzyloxy)-2-nitrophenylsulfonamido)piperidine-1,2-dicarboxylate (251 g, 0.45 mol) in DMF (1200 mL). The reaction mixture was then stirred at 20° C. overnight. The reaction mixture was diluted with water and extracted with EtOAc (3×). The combined organic layer was washed with brine (3×), concentrated in vacuum and purified by silica gel column chromatography (3; 1 petroleum ether/EtOAc) to afford (2S,5R)-1-tert-butyl 2-ethyl 5-((benzyloxy)amino)piperidine-1,2-dicarboxylate (122.9 g, 85%) as a yellow solid.

Step 5: Synthesis of (2S,5R)-ethyl 5-((benzyloxy)amino)piperidine-2-carboxylate

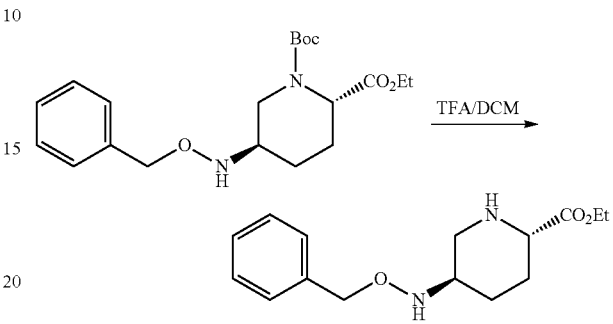

TFA (600 mL) was added to a solution of (2S,5R)-1-tert-butyl 2-ethyl 5-((benzyloxy)amino)piperidine-1,2-dicarboxylate (263 g, 0.7 mol) in DCM (600 mL) at 20° C. The mixture was stirred at rt overnight and then concentrated in vacuum. The crude product was adjusted to pH 10 with sat. NaHCO$_3$ solution, and then extracted with DCM three times. The combined organic layer was concentrated in vacuum and purified by silica gel column chromatography (20:1 DCM/MeOH) to afford (2S,5R)-ethyl 5-((benzyloxy)amino)piperidine-2-carboxylate (184.9 g, 95%) as a yellow oil.

Step 6: Synthesis of (2S,5R)-ethyl 6-(benzyloxy)-7-oxo-1,6-diazabicyclo[3.2.1]octane-2-carboxylate

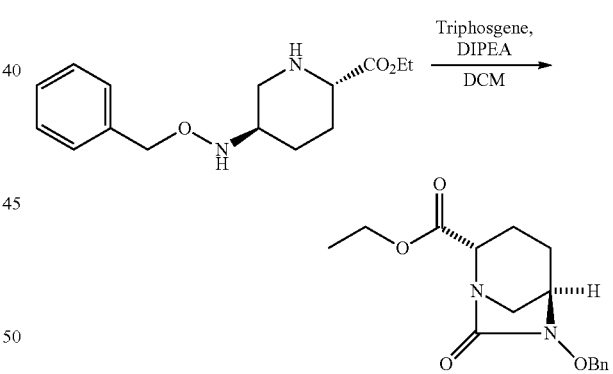

Triphosgene (21.3 g, 72 mmol) was added in portions to a solution of (2S,5R)-ethyl 5-((benzyloxy)amino)piperidine-2-carboxylate (50 g, 0.18 mol) and DIPEA (128 mL, 0.72 mol) in DCM (2000 mL) at 0° C. After stirring at 20° C. overnight, the reaction mixture was washed with H$_3$PO$_4$ (10%), sat. NaHCO$_3$ and saturated NaCl. The combined organic layer was concentrated in vacuum and purified by silica gel column chromatography (3:1 petroleum ether/EtOAc) to afford (2S,5R)-ethyl 6-(benzyloxy)-7-oxo-1,6-diazabicyclo[3.2.1]octane-2-carboxylate (27.4 g, 50%) as a yellow solid. $^1$H NMR (400 Mz, CDCl$_3$): δ 7.43-7.36 (m, 5H), 5.06 (d, J=11.4 Hz, 1H), 4.90 (d, J=11.4 Hz, 1H), 4.24 (q, J=7.1 Hz, 2H), 4.11-4.08 (m, 1H), 3.32-3.31 (m, 1H), 3.08-3.05 (m, 1H), 2.93 (d, J=11.9 Hz, 1H), 2.14-2.05 (m, 2H), 2.05-2.00 (m, 1H), 1.71-1.63 (m, 1H), 1.29 (t, J=7.1 Hz, 3H).

Example 2

Synthesis of (2S,5R)-6-(benzyloxy)-7-oxo-1,6-diazabicyclo[3.2.1]octane-2-carboxylic acid (Intermediate Compound 2a)

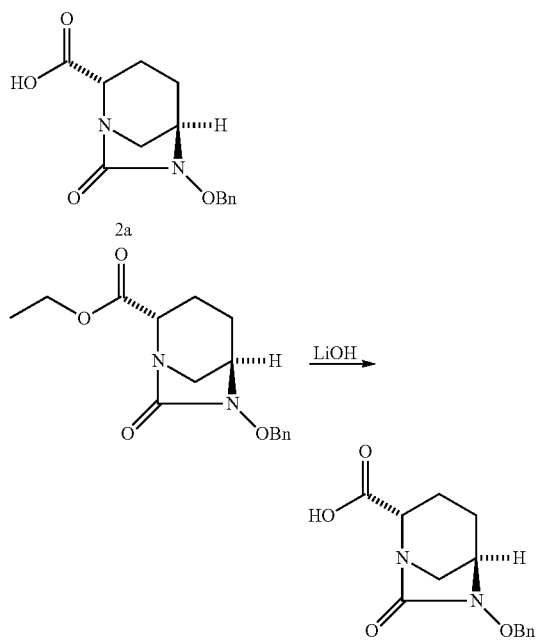

LiOH (1.2 g, 29.6 mmol) was added to a solution of (2S,5R)-ethyl 6-(benzyloxy)-7-oxo-1,6-diazabicyclo[3.2.1]octane-2-carboxylate (9 g, 29.6 mmol) in THF/H$_2$O (3:1, 240 mL). The mixture was then stirred at rt overnight. The reaction mixture was washed with EtOAc twice, then the aqueous solution was adjusted pH 2-3 with 1N HCl. The resulting mixture was extracted with DCM three times, and the combined organic layer was dried over saturated Na$_2$SO$_4$ and concentrated in vacuum to provide (2S,5R)-6-(benzyloxy)-7-oxo-1,6-diazabicyclo[3.2.1]octane-2-carboxylic acid (7.0 g, 77.7%), which was directly used in the next step without further purification. ESI-MS (EI$^+$, m/z): 277.31. $^1$H NMR (300 MHz, CDCl$_3$) δ 7.49-7.29 (m, 5H), 5.06 (d, J=11.4 Hz, 1H), 4.91 (d, J=11.4 Hz, 1H), 4.15-4.10 (m, 1H), 3.36-3.34 (m, 1H), 3.15-3.11 (m, 1H), 2.83 (d, J=11.8 Hz, 1H), 2.32-2.15 (m, 1H), 2.11-2.01 (m, 2H), 1.74-1.56 (m, 1H).

Example 3

Synthesis of (2S,5R)-6-(benzyloxy)-7-oxo-1,6-diazabicyclo[3.2.1]octane-2-carbaldehyde (Intermediate Compound 2b)

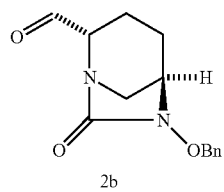

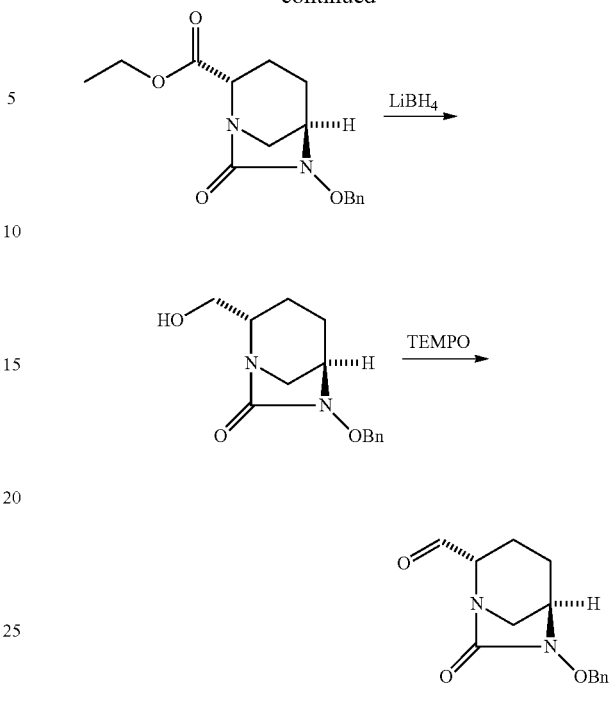

LiBH$_4$ (0.54 g, 24.67 mmol) was added to a solution of (2S,5R)-ethyl 6-(benzyloxy)-7-oxo-1,6-diazabicyclo[3.2.1]octane-2-carboxylate (5 g, 16.44 mmol) in MeOH (50 mL) at −10° C. After 15 min, another portion of LiBH$_4$ (0.54 g, 24.67 mmol) was added and the mixture was stirred at −10 to 0° C. for 4-5 h. The reaction mixture was carefully quenched by addition of sat. NaH$_2$PO$_4$ (50 mL) at 0° C. The mixture was diluted with water (20 mL) and extracted with DCM three times. The combined organic layer was concentrated and purified by silica gel column chromatography (gradient elution 0-100% petroleum ether/EtOAc, then 0-2% MeOHEtOAc) to give (2S,5R)-6-(benzyloxy)-2-(hydroxymethyl)-1,6-diazabicyclo[3.2.1]octan-7-one (3.8 g, 88%) as a white solid. ESI-MS (EI$^+$, m/z): 263.1. $^1$H-NMR (500M, CDCl$_3$): 7.44-7.35 (m, 5H), 5.05 (d, J=11.5 Hz, 1H), 4.90 (d, J=11.5 Hz, 1H), 3.73-3.69 (m, 1H), 3.61-3.58 (m, 2H), 3.33 (m, 1H), 3.01 (br d, J=12.0 Hz, 1H), 2.91 (m, 1H), 2.03-1.95 (m, 2H), 1.58-1.54 (m, 1H), 1.39-1.24 (m, 1H).

TEMPO (48 mg, 0.3 mmol) was added in portioned to a solution of (2S,5R)-6-(benzyloxy)-2-(hydroxymethyl)-1,6-diazabicyclo[3.2.1]octan-7-one (7.8 g, 30 mmol) and 1,3,5-trichloro-1,3,5-triazinane-2,4,6-trione (7.0 g, 30 mmol) in DCM (100 mL) at 0° C. The mixture was stirred at 0° C. for 2 h, and filtered through Celite®. The filtrate was dried over Na$_2$SO$_4$ and concentrated to afford (2S,5R)-6-(benzyloxy)-7-oxo-1,6-diazabicyclo[3.2.1]octane-2-carbaldehyde (7.0 g, 90%) as a yellow oil. ESI-MS (EI$^+$, m/z): 261.1. $^1$H-NMR (500M, CDCl$_3$): 9.74 (s, 1H), 7.45-7.36 (m, 5H), 5.07 (d, J=11.5 Hz, 1H), 4.92 (d, J=11.5 Hz, 1H), 3.89 (d, J=8.0 Hz, 1H), 3.27 (m, 1H), 3.21-3.05 (m, 1H), 2.56 (d, J=12.0 Hz, 1H), 2.20-2.15 (m, 1H), 2.05-2.01 (m, 1H), 1.95-1.93 (m, 1H), 1.49-1.46 (m, 1H).

Example 4

Synthesis of (2S,5R)-2-(isoxazol-3-yl)-7-oxo-1,6-diazabicyclo[3.2.1]octan-6-yl hydrogen sulfate (Compound 101)

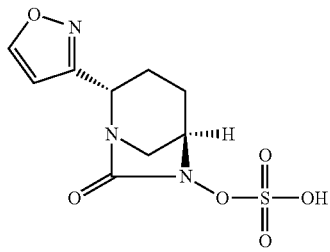 [SMILES: O=C1N2C[C@@H](CC[C@H]2c2ccon2)N1OS(=O)(=O)O]

Step 1: Synthesis of (E)-6-(benzyloxy)-7-oxo-1,6-diazabicyclo[3.2.1f]octane-2-carbaldehyde oxime

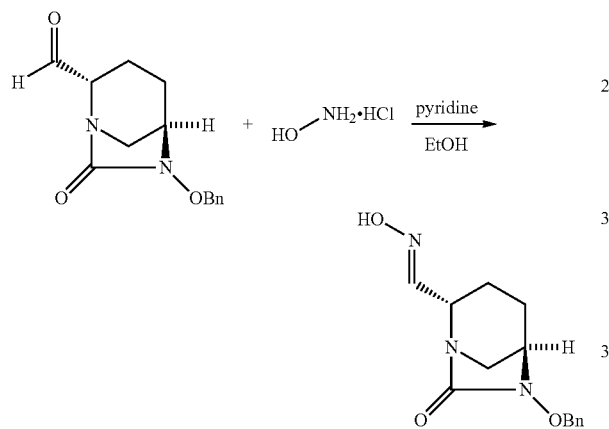

A solution of (2S,5R)-6-(benzyloxy)-7-oxo-1,6-diazabicyclo[3.2.1]octane-2-carbaldehyde (510 mg, 1.96 mmol), hydroxylamine hydrochloride (158 mg, 2.27 mmol) and pyridine (621 mg, 7.85 mmol) in EtOH (15 mL) was stirred at rt for 2 hrs. The reaction mixture was then concentrated and the residue was diluted with DCM (25 mL), washed with water (3×), saturated sodium chloride, dried over $Na_2SO_4$ and concentrated. The residue was purified by silica gel column chromatography (gradient elution 3:1 to 3:2 petroleum ether/EtOAc) to afford (E)-6-(benzyloxy)-7-oxo-1,6-diazabicyclo[3.2.1]octane-2-carbaldehyde oxime (228 mg, 42%) as a white solid. ESI-MS (EI$^+$, m/z): 276 [M+H]$^+$.

Step 2-4: Synthesis of (2S,5R)-6-(benzyloxy)-2-(isoxazol-3-yl)-1,6-diazabicyclo[3.2.1]octan-7-one

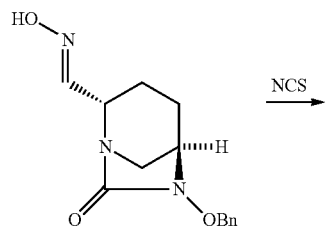

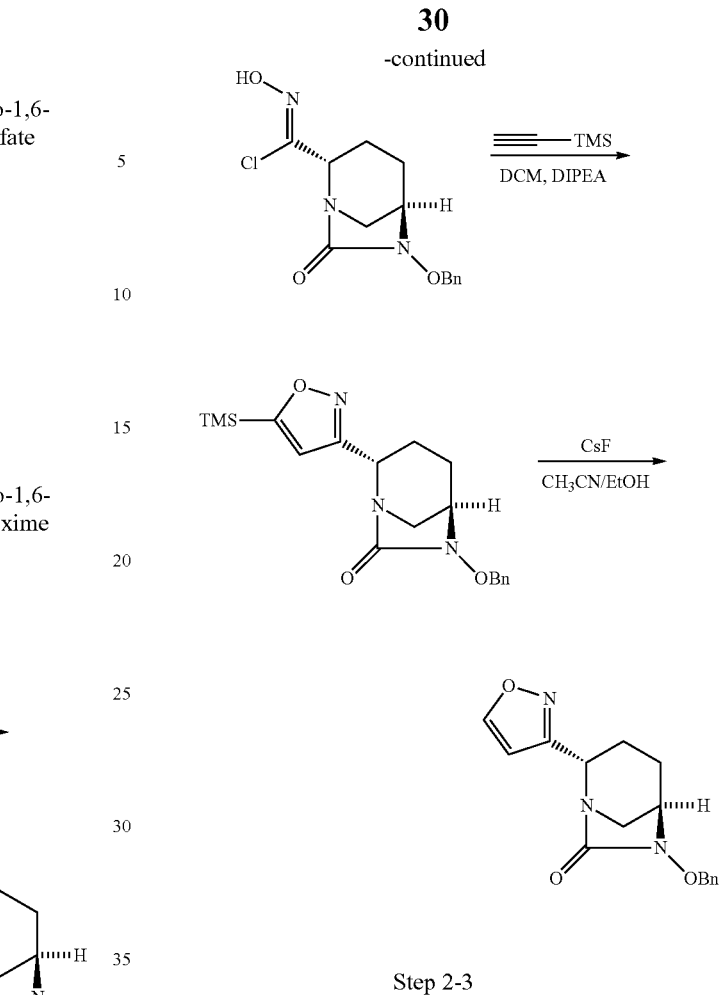

Step 2-3

NCS (290 mg, 2.17 mmol) and pyridine (2 drops) were added to a solution of (E)-6-(benzyloxy)-7-oxo-1,6-diazabicyclo[3.2.1]octane-2-carbaldehyde oxime (560 mg, 2.04 mmol) in dry DCM (15 mL). The reaction mixture was stirred at rt for about 3-4 hrs. Ethynyltrimethylsilane (240 mg, 2.44 mmol) was added, then a solution of DIPEA (290 mg, 2.24 mmol) in dry DCM (5 mL) was added slowly over a 0.5 h period. After addition, the reaction mixture was stirred at rt overnight. The reaction mixture was then washed with 10% citric acid, water, saturated sodium chloride (10 mL), dried and concentrated. The residue was purified by silica gel column chromatography (10:1 petroleum ether/EtOAc) to afford (2S,5R)-6-(benzyloxy)-2-(5-(trimethylsilyl)isoxazol-3-yl)-1,6-diazabicyclo[3.2.1]octan-7-one (300 mg, 41%) as a colorless oil. ESI-MS (EI$^+$, m/z): 372 [M+H]$^+$.

Step 4

CsF (230 mg, 1.512 mmol was added to a solution of (2S,5R)-6-(benzyloxy)-2-(5-(trimethylsilyl)isoxazol-3-yl)-1,6-diazabicyclo[3.2.1]octan-7-one (187 mg, 0.504 mmol) in $CH_3CN$/EtOH (15 mL, 3:1). After stirring at rt for 2 hrs, the reaction mixture was concentrated and the residue was dissolved in DCM (25 mL), washed with water (3×), and saturated sodium chloride, then, dried, and concentrated. The residue was purified by silica gel column chromatography (6:1 petroleum ether/EA) to afford (2S,5R)-6-(benzyloxy)-2-(isoxazol-3-yl)-1,6-diazabicyclo[3.2.1]octan-7-one (116 mg, 77%) as a white solid. ESI-MS (EI$^+$, m/z): 300 [M+H]$^+$.

Step 5-6: Synthesis of (2S,5R)-2-(isoxazol-3-yl)-7-oxo-1,6-diazabicyclo[3.2.1]octan-6-yl hydrogen sulfate

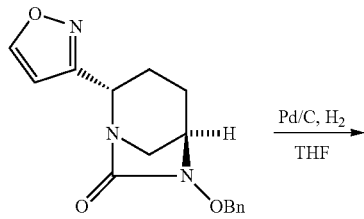

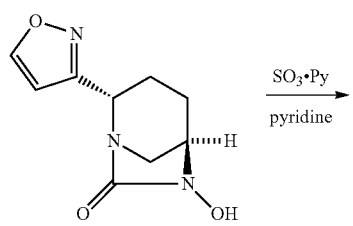

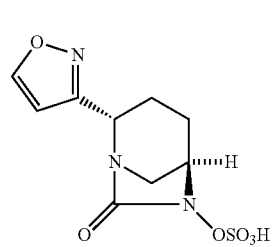

A mixture of (2S,5R)-6-(benzyloxy)-2-(isoxazol-3-yl)-1,6-diazabicyclo[3.2.1]octan-7-one (196 mg, 0.656 mmol) and 10% Pd/C (80 mg) in THF (20 mL) was stirred at rt for 1.5 h under $H_2$. The reaction mixture was then filtered and concentrated. The residue was washed with $Et_2O$ (3×) and dried under high vacuum to afford (2S,5R)-6-hydroxy-2-(isoxazol-3-yl)-1,6-diazabicyclo[3.2.1]octan-7-one (130 mg, 98%), which was in the next step directly. ESI-MS (EI$^+$, m/z): 210 [M+H]$^+$.

A mixture of (2S,5R)-6-hydroxy-2-(isoxazol-3-yl)-1,6-diazabicyclo[3.2.1]octan-7-one (130 mg, 0.621 mmol) and $SO_3$.Py complex (495 mg, 3.11 mmol) in dry pyridine (5.5 mL) was stirred at rt for 3 hrs. The reaction mixture was then concentrated in vacuum and the residue was redissolved in aqueous $NaH_2PO_4$ (1.5 M, 20 mL). Tetra-butylammonium hydrogensulphate (320 mg) was added. The mixture was stirred at rt for 20 min, and extracted with DCM (4×). The combined organic layer was dried and concentrated and the residue was purified by prep-HPLC using ammonium bicarbonate buffer to afford ammonium (2S,5R)-2-(isoxazol-3-yl)-7-oxo-1,6-diazabicyclo[3.2.1]octan-6-yl sulfate (10 mg, 13%) as a white solid. ESI-MS (EI$^-$, m/z): 288 [M]$^-$. $^1$H NMR (500 MHz, $D_2O$) δ 8.06 (s, 1H), 6.53 (s, 1H), 4.66 (m, 1H), 4.14 (m, 1H), 3.12-3.08 (m, 1H), 2.92 (d, J=12.5 Hz, 1H), 2.24-2.21 (m, 1H), 2.11-2.08 (m, 2H), 1.87-1.86 (m, 1H).

Example 5

Synthesis of (2S,5R)-2-(5-cyanoisoxazol-3-yl)-7-oxo-1,6-diazabicyclo[3.2.1]octan-6-yl hydrogen sulfate (Compound 102)

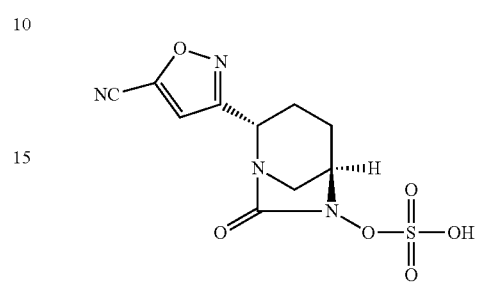

Step 1: Synthesis of 3-((2S,5R)-6-(benzyloxy)-7-oxo-1,6-diazabicyclo[3.2.1]octan-2-yl)isoxazole-5-carbonitrile

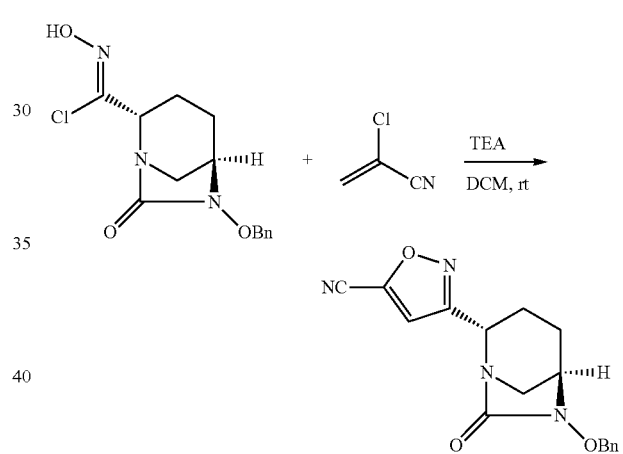

2-Chloroacrylonitrile (1.08 g, 12.4 mmol) was added to a solution of (2S,5R)-6-(benzyloxy)-N-hydroxy-7-oxo-1,6-diaza-bicyclo[3.2.1]octane-2-carbimidoyl chloride (1.9 g, 6.2 mmol) in DCM (19 mL) at −5° C., followed by dropwise addition of TEA (1.25 g, 1.24 mmol). The mixture was stirred at −5° C. for 2 hrs and was then quenched with 10% critic acid (20 mL). The organic phase was separated, washed with 10% critic acid, $H_2O$, and saturated sodium chloride, then concentrated. The residue was purified by silica gel column chromatography (gradient elution 15:1 to 4:1 petroleum ether/EtOAc) to afford 3-((2S,5R)-6-(benzyloxy)-7-oxo-1,6-diaza-bicyclo[3.2.1]octan-2-yl)isoxazole-5-carbonitrile (325 mg, 16%) as a white solid. $^1$H-NMR (500 MHz, CDCl$_3$): δ 7.45-7.35 (m, 5H), 7.04 (s, 1H), 5.09 (d, J=11.3 Hz, 1H), 4.94 (d, J=11.3 Hz, 1H), 4.64 (d, J=7.0 Hz, 1H), 3.34 (s, 1H), 2.90 (br d, J=12.0 Hz, 1H), 2.54 (d, J=12.0 Hz, 1H), 2.40-2.35 (m, 1H), 2.31-2.25 (m, 1H), 2.14-2.11 (m, 1H), 1.80-1.74 (m, 1H).

Step 2: Deprotection of O-Bn group using BCl$_3$

BCl$_3$ (1M in DCM, 1.6 mL) was added to a solution of 3-((2S,5R)-6-(benzyloxy)-7-oxo-1,6-diaza-bicyclo[3.2.1]octan-2-yl)isoxazole-5-carbonitrile (104 mg, 0.32 mmol) in dry $CH_2Cl_2$ (9 mL) at −78° C. The mixture was stirred −78° C.

for 2 hrs and quenched carefully with MeOH (2 mL). The solvents were removed in vacuum and the residue was partitioned between EtOAc and water. The organic phase was separated, washed with brine, dried over $Na_2SO_4$, and concentrated to afford 3-((2S,5R)-6-hydroxy-7-oxo-1,6-diazabicyclo[3.2.1]octan-2-yl)isoxazole-5-carbonitrile (45 mg, 60%), which was used directly in the next step. ESI-MS (EI+, m/z): 235.1 [M+H]+.

Step 3: Synthesis of (2S,5R)-2-(5-cyanoisoxcizol-3-yl)-7-oxo-1,6-diazabicyclo[3.2.1]octan-6-yl hydrogen sulfate A mixture of 3-((2S,5R)-6-hydroxy-7-oxo-1,6-diaza-bicyclo[3.2.1]octan-2-yl)isoxazole-5-carbonitrile (45 mg, 0.19 mmol) and $SO_3$.Py complex (260 mg, 1.6 mmol) in dry pyridine (10 mL) was stirred at rt for 3 hrs. The reaction mixture was then concentrated in vacuum and the residue was redissolved in aqueous $NaH_2PO_4$ (1.5 M, 5 mL). Tetrabutylammonium hydrogensulphate (80 mg) was added. The mixture was stirred at rt for 20 minutes, then extracted with EtOAc (4×). The combined organic layer was dried and concentrated. The residue was purified by prep-HPLC using ammonium formate buffer to afford ammonium (2S,5R)-2-(5-cyanoisoxazol-3-yl)-7-oxo-1,6-diazabicyclo[3.2.1]octan-6-yl sulfate (11 mg, 17%) as a white solid. ESI-MS (EI−, m/z): 313.1 [M−H]−. 1H-NMR (500 MHz, $D_2O$): δ 7.32 (s, 1H), 4.69 (m, 1H, overlapped with $D_2O$ peak), 4.14 (br s, 1H), 3.12 (br d, J=12.0 Hz, 1H), 2.89 (d, J=12.5 Hz, 1H), 2.29-2.25 (m, 1H), 2.14-2.07 (m, 2H), 1.88-1.84 (m, 1H).

Example 6

Synthesis of (2S,5R)-2-(5-carbamoylisoxazol-3-yl)-7-oxo-1,6-diazabicyclo[3.2.1]octan-6-yl hydrogen sulfate (Compound 103)

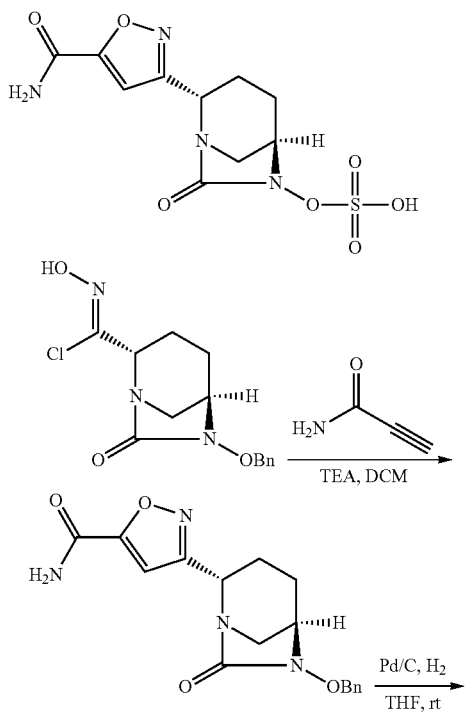

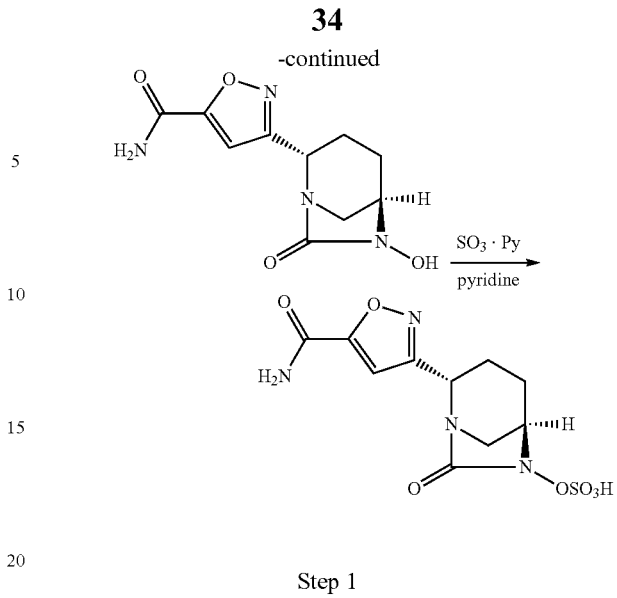

Step 1

Propiolamide (0.30 g, 4.37 mmol) was added to a solution of (2S,5R,Z)-6-(benzyloxy)-N-hydroxy-7-oxo-1,6-diazabicyclo[3.2.1]octane-2-carbimidoyl chloride (3.64 mmol) in dry DCM (10 mL), followed by the addition of TEA (0.56 mL, 4.0 mmol) in DCM (2 mL) over a 30 minute period. The reaction mixture was stirred at rt overnight. Then the mixture was diluted with EtOAc, washed with water and saturated sodium chloride. The combined organic layer was dried over $Na_2SO_4$, concentrated and purified by silica gel column chromatography (gradient elution 5:1 to 1:2, petroleum ether/EtOAc containing 1% TEA) to afford 3-((2S,5R)-6-(benzyloxy)-7-oxo-1,6-diaza-bicyclo[3.2.1]octan-2-yl)isoxazole-5-carboxamide (0.4 g, 32%) as a yellow solid. ESI-MS (EI+, m/z): 343 [M+H]+.

Step 2

A mixture of 3-((2S,5R)-6-(benzyloxy)-7-oxo-1,6-diazabicyclo[3.2.1]octan-2-yl)isoxazole-5-carboxamide (0.25 g, 0.73 mmol) and 10% Pd/C (0.12 g) in THF (8 mL) was stirred at rt under $H_2$ atmosphere for 2 hrs. The reaction mixture was then filtered and concentrated to afford 3-((2S,5R)-6-hydroxy-7-oxo-1,6-diaza-bicyclo[3.2.1]octan-2-yl)isoxazole-5-carboxamide (0.17 g, 90%) as a light yellow solid, which was used directly in the next step. ESI-MS (EI+, m/z): 253 [M+H]+.

Step 3

To a solution of 3-((2S,5R)-6-hydroxy-7-oxo-1,6-diazabicyclo[3.2.1]octan-2-yl)isoxazole-5-carboxamide (0.165 g, 0.65 mmol) in dried pyridine (2 mL) was added $SO_3$.Py (0.73 g, 4.58 mmol). The mixture was stirred at rt for 2 hrs. The pyridine was evaporated under vacuum and the residue was purified by prep-HPLC using ammonium hydroxide buffer to give ammonium (2S,5R)-2-(5-carbamoylisoxazol-3-yl)-7-oxo-1,6-diazabicyclo[3.2.1]octan-6-yl sulfate (70 mg, 33%) as a light yellow solid. ESI-MS (EI−, m/z): 331 [M−H]+.

Step 4: Na Resin Exchange

Ammonium (2S,5R)-2-(5-carbamoylisoxazol-3-yl)-7-oxo-1,6-diazabicyclo[3.2.1]octan-6-yl sulfate (40 mg) was dissolved in a minimum amount of water and acetone (0.5 mL/0.5 mL) and passed through a column of 1 g of DOWEX 50Wx8 Na⁺ resin (the resin was pre-washed with HPLC grade of water to neutral) and eluted with HPLC grade water to afford sodium (2S,5R)-2-(5-carbamoylisoxazol-3-yl)-7-oxo-1,6-diaza-bicyclo[3.2.1]octan-6-yl sulfate (30 mg, 75%) as a white solid after lyophilization. ESI-MS (EI⁻, m/z): 331.0 [M−H]⁻; ¹H-NMR (500 MHz, D$_2$O): δ 7.02 (s, 1H), 4.69 (m, 1H, overlapped with D$_2$O peak), 4.13 (br s, 1H), 3.12 (br d, J=13.5 Hz, 1H), 2.93 (d, J=12.5 Hz, 1H), 2.25-2.23 (m, 1H), 2.12-2.04 (m, 2H), 1.86-1.83 (m, 1H).

Example 7

Synthesis of (2S,5R)-2-(5-methyl-1,3,4-oxadiazol-2-yl)-7-oxo-1,6-diazabicyclo[3.2.1]octan-6-yl hydrogen sulfate (Compound 200)

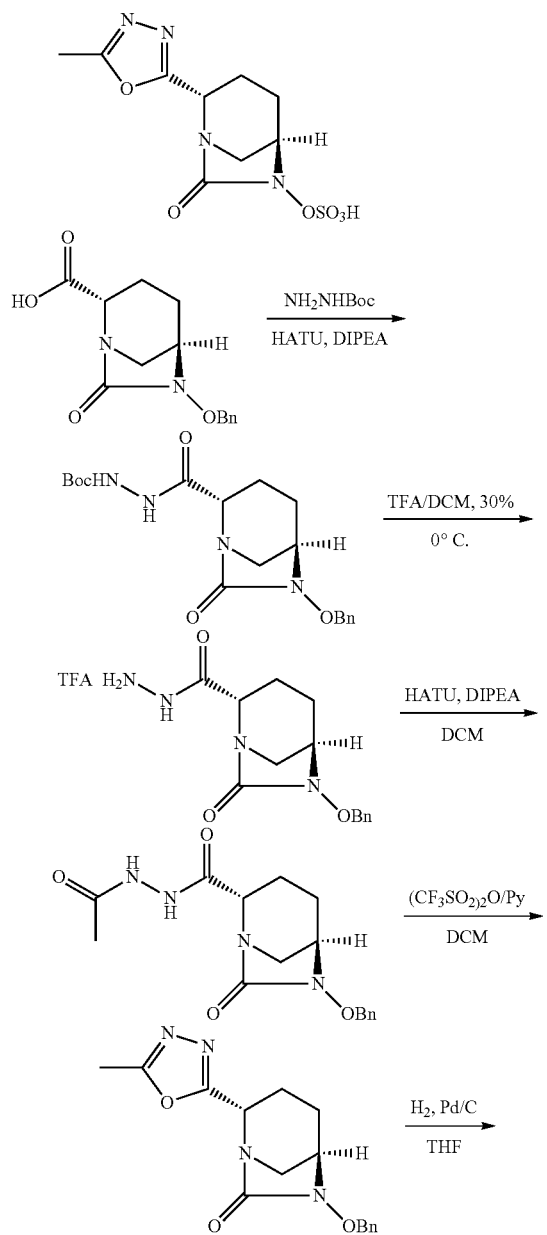

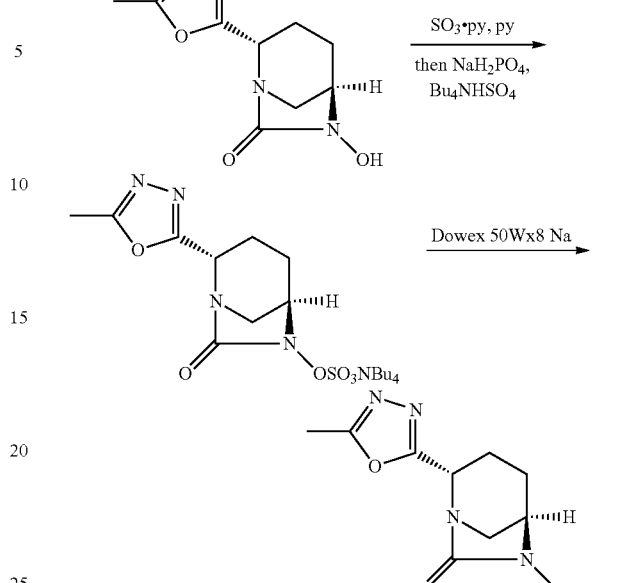

Step 1

HATU (8.3 g, 21.7 mmol) was added to a solution of (2S,5R)-6-(benzyloxy)-7-oxo-1,6-diazabicyclo[3.2.1]octane-2-carboxylic acid (5.0 g, 18.1 mmol) and tert-butyl hydrazinecarboxylate (3.5 g, 27.2 mmol) in DCM (60 mL) at 0° C., followed by the addition of DIPEA (7.0 g, 54.3 mmol). The resulting mixture was stirred at 0° C. for 1 h. The reaction mixture was then diluted with DCM, washed with water (2×), and saturated sodium chloride, then dried over Na$_2$SO$_4$ and concentrated. The residue was purified by silica gel column chromatography (gradient elution 10:1 to 4:1 petroleum ether/EtOAc) to afford tert-butyl 2-((2S,5R)-6-(benzyloxy)-7-oxo-1,6-diazabicyclo[3.2.1]octane-2-carbonyl)hydrazinecarboxylate (6 g, 85%). ESI-MS (EI⁺, m/z): 391 [M+H]⁺.

Step 2

TFA (15 mL) was added dropwise to a solution of tert-butyl 2-((2S,5R)-6-(benzyloxy)-7-oxo-1,6-diazabicyclo[3.2.1]octane-2-carbonyl)hydrazinecarboxylate (3 g, 7.7 mmol) in DCM (30 mL) at 0° C. The resulting mixture was stirred at rt for 1 h, and then concentrated. The residue was further dried under high vacuum and washed with Et$_2$O (3×) to afford (2S,5R)-6-(benzyloxy)-7-oxo-1,6-diazabicyclo[3.2.1]octane-2-carbohydrazide TFA salt (3 g, 93%) as a white solid. ESI-MS (EI⁺, m/z): 291 [M+H]⁺.

Step 3

HATU (0.90 g, 2.48 mmol) was added to a solution of (2S,5R)-6-(benzyloxy)-7-oxo-1,6-diazabicyclo[3.2.1]octane-2-carbohydrazide TFA salt (1.0 g, 2.48 mmol), acetic acid (0.12 g, 2.07 mmol) and DIPEA (1.1 g, 8.3 mmol) in dry DMF (10 mL) at 0° C. The reaction mixture was stirred at 0° C. for 1 h. The mixture was then quenched with saturated sodium chloride (50 mL) and exacted with EtOAc (3×). The combined organic layer was washed with saturated sodium chloride (2×), dried over Na$_2$SO$_4$, and concentrated. The residue was purified by silica gel column chromatography (gradient elution 10:1 to 1:10 petroleum ether/EtOAc) to afford (2S,5R)—N'-acetyl-6-(benzyloxy)-7-oxo-1,6-diazabicyclo[3.2.1]octane-2-carbohydrazide (0.6 g, 73%). ESI-MS (EI$^+$, m/z): 333 [M+H]$^+$.

Step 4

(CF$_3$SO$_2$)$_2$O (0.50 mL) was slowly added to a solution of (2S,5R)—N'-acetyl-6-(benzyloxy)-7-oxo-1,6-diazabicyclo[3.2.1]octane-2-carbohydrazide (0.5 g) and pyridine (0.5 mL) in dry DCM (10 mL) at −10° C. The reaction mixture was stirred at 0° C. for 1 h and then quenched carefully with sat. NaHCO$_3$. The organic layer was separated and the aqueous layer was exacted with EtOAc (3×). The combined organic layer was dried over Na$_2$SO$_4$, concentrated and purified by silica gel column chromatography (gradient elution 10:1 to 1:1 petroleum ether/EtOAc) to afford (2S,5R)-6-(benzyloxy)-2-(5-methyl-1,3,4-oxadiazol-2-yl)-1,6-diaza-bicyclo[3.2.1]octan-7-one (0.3 g, 63%) as a slight yellow solid. ESI-MS (EI$^+$, m/z): 315.0 [M+H]$^+$.

Step 5

A mixture of ((2S,5R)-6-(benzyloxy)-2-(5-methyl-1,3,4-oxadiazol-2-yl)-1,6-diaza-bicyclo[3.2.1]octan-7-one (0.2 g, 0.6 mmol) and 10% Pd/C (0.2 g) in THF (20 mL) was stirred under H$_2$ atmosphere at rt for 3 hrs. The reaction mixture was then filtered and concentrated to afford (2S,5R)-6-hydroxy-2-(5-methyl-1,3,4-oxadiazol-2-yl)-1,6-diazabicyclo[3.2.1]octan-7-one (0.13 g, 92%) as a white solid, which was used directly in the next step. ESI-MS (EI$^+$, m/z): 225 [M+H]$^+$.

Step 6

To a solution of (2S,5R)-6-hydroxy-2-(5-methyl-1,3,4-oxadiazol-2-yl)-1,6-diazabicyclo[3.2.1]octan-7-one (130 mg, 0.5 mmol) in dry pyridine (2 mL) was added SO$_3$.Py (46 mg, 2.9 mmol). The mixture was stirred at rt for 3 h and then concentrated under vacuum. The residue was then redissolved in aqueous NaH$_2$PO$_4$ (1.5 M, 10 mL). Tetra-butylammonium hydrogensulphate (236 mg, 0.69 mmol) was added. The mixture was stirred at rt for 20 minutes, then extracted with EtOAc (4×). The combined organic layer was dried and concentrated and the residue was purified by silica gel column chromatography (gradient elution 10:1 to 5:1 DCM/acetone) to afford tetrabutylammonium (2S,5R)-2-(5-methyl-1,3,4-oxadiazol-2-yl)-7-oxo-1,6-diazabicyclo[3.2.1]octan-6-yl sulfate (120 mg, 38%) as a colorless oil. ESI-MS (EI$^-$, m/z): 303.0 [M−H]$^-$. $^1$H-NMR (500 MHz, CDCl$_3$): δ4.65 (br d, J=7.5 Hz, 1H), 4.39 (br s, 1H), 3.35-3.24 (m, 9H), 2.84 (d, J=12 Hz, 1H), 2.54 (s, 3H), 2.33-2.21 (m, 2H), 2.21-2.16 (m, 1H), 2.03-1.97 (m, 1H), 1.75-1.64 (m, 8H), 1.48-1.43 (m, 8H), 1.02-0.99 (m, 12H).

Step 7: Sodium Resin Exchange

Tetrabutylammonium (2S,5R)-2-(5-methyl-1,3,4-oxadiazol-2-yl)-7-oxo-1,6-diazabicyclo[3.2.1]octan-6-yl sulfate (120 mg) was dissolved in a minimum amount of water and acetone (0.5 mL:0.5 mL) and passed through a column of 10 g of DOWEX 50Wx8 Na$^+$ resin (the resin was pre-washed with HPLC grade of water to neutral) and eluted with HPLC grade water to afford sodium (2S,5R)-2-(5-methyl-1,3,4-oxadiazol-2-yl)-7-oxo-1,6-diazabicyclo[3.2.1]octan-6-yl sulfate (70 mg, 98%) after lyophilization as a white solid. ESI-MS (EI$^-$, m/z): 303.1 [M−H]$^-$. $^1$H-NMR (500 MHz, D$_2$O): δ 5.02-5.00 (br d, J=7.0 Hz, 1H), 4.45 (s, 1H), 3.46-3.43 (br d, J=12.5 Hz, 1H), 3.19 (d, J=12.0 Hz, 1H), 2.76 (s, 3H), 2.55-2.51 (m, 1H), 2.46-2.37 (m, 2H), 2.24-2.17 (m, 1H).

Example 8

Synthesis of (2S,5R)-2-(5-ethyl-1,3,4-oxadiazol-2-yl)-7-oxo-1,6-diazabicyclo[3.2.1]octan-6-yl hydrogen sulfate (Compound 201)

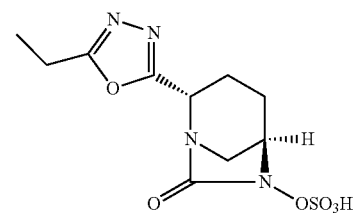

Sodium (2S,5R)-2-(5-ethyl-1,3,4-oxadiazol-2-yl)-7-oxo-1,6-diazabicyclo[3.2.1]octan-6-yl sulfate was obtained by a similar method as Step 3-7 of Example 7, using propionic acid in place of HOAc in Step 3. After lyophilization a white solid was obtained (59 mg, 90%). ESI-MS (EI$^-$, m/z): 317.1 [M−H]$^-$. $^1$H-NMR (500 MHz, D$_2$O): δ 4.84 (d, J=7.0 Hz, 1H), 4.28 (br s, 1H), 3.28-3.26 (br d, J=12.0 Hz, 1H), 3.01 (d, J=12.0 Hz, 1H), 2.95 (q, J=7.8 Hz, 2H), 2.38-2.34 (m, 1H), 2.27-2.21 (m, 2H), 2.06-2.00 (m, 1H), 1.36 (t, J=7.8 Hz, 3H).

Example 9

Synthesis of (2S,5R)-2-(5-(hydroxymethyl)-1,3,4-oxadiazol-2-yl)-7-oxo-1,6-diazabicyclo[3.2.1]octan-6-yl hydrogen sulfate (Compound 202)

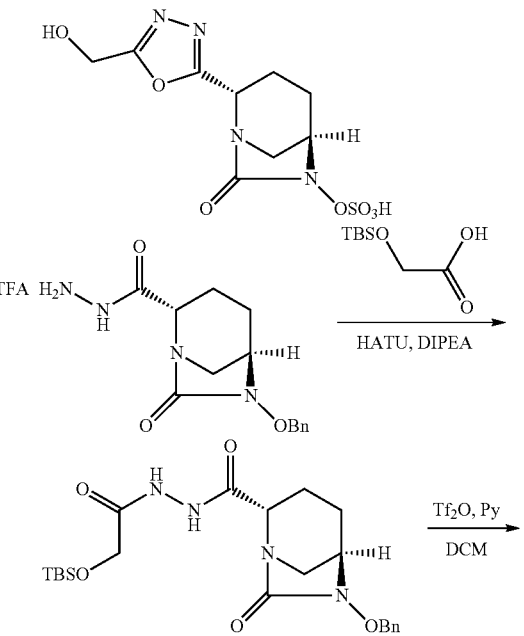

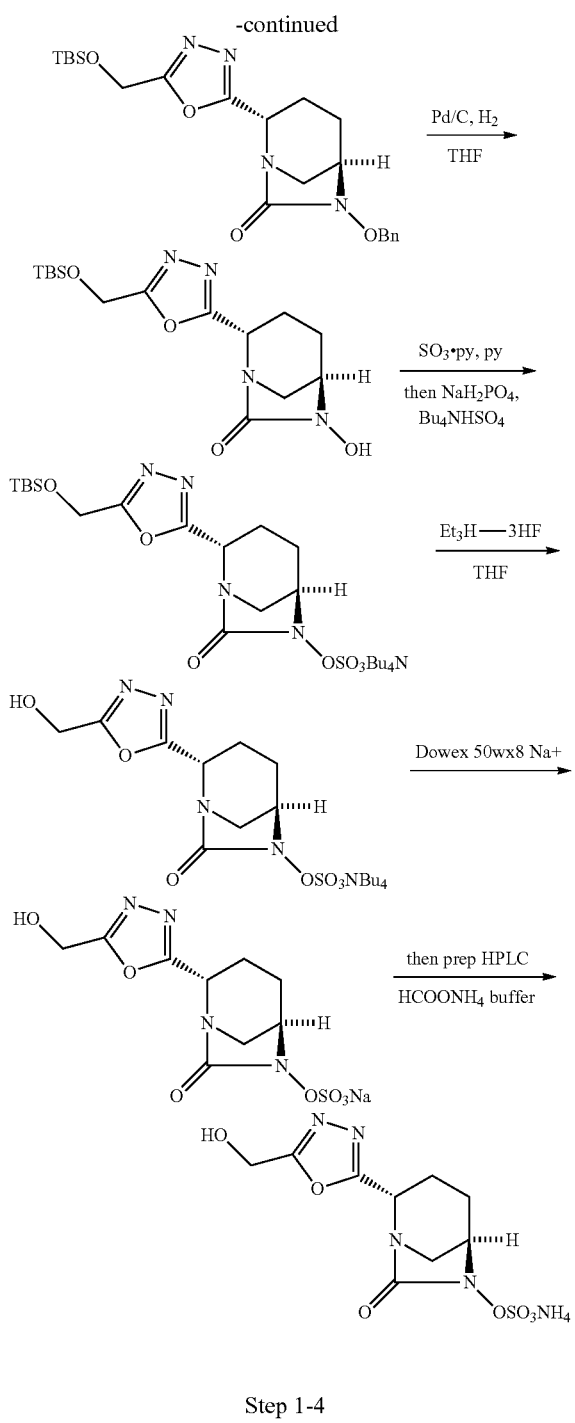

Step 1-4

Tetrabutylammonium (2S,5R)-2-(5-(((tert-butyldimethylsilyl)oxy)methyl)-1,3,4-oxadiazol-2-yl)-7-oxo-1,6-diazabicyclo[3.2.1]octan-6-yl sulfate (450 mg) was obtained by a similar method as Steps 3-6 of Example 7 using 2-((tert-butyldimethylsilyl)oxy)acetic acid in place of HOAc in Step 3. ESI-MS (EI⁻, m/z): 433 [M–H]⁻.

Step 5

To a solution of tetrabutylammonium (2S,5R)-2-(5-(((tert-butyldimethylsilyl)oxy)methyl)-1,3,4-oxadiazol-2-yl)-7-oxo-1,6-diazabicyclo[3.2.1]octan-6-yl sulfate (450 mg, 0.7 mmol) in dry THF (40 mL) was added Et₃N-3HF (340 mg, 2.1 mmol). The resulting mixture was stirred at rt overnight, then concentrated. The residue was purified by silica gel column chromatography (3:1 acetone/ethanol) to afford tetrabutyl ammonium (2S,5R)-2-(5-(hydroxymethyl)-1,3,4-oxadiazol-2-yl)-7-oxo-1,6-diazabicyclo[3.2.1]octan-6-yl sulfate (160 mg, 73%) as a white solid. ESI-MS (EI⁻, m/z): 319 [M–H]⁻.

Step 6

Tetrabutyl ammonium (2S,5R)-2-(5-(hydroxymethyl)-1,3,4-oxadiazol-2-yl)-7-oxo-1,6-diazabicyclo[3.2.1]octan-6-yl sulfate (160 mg) was dissolved in a minimum amount of water and acetone (0.5 mL/0.5 mL) and passed through a column of 10 g of DOWEX 50Wx8 Na⁺ resin (the resin was pre-washed with HPLC grade of water to neutral) and eluted with HPLC grade water to provide sodium (2S,5R)-2-(5-(hydroxymethyl)-1,3,4-oxadiazol-2-yl)-7-oxo-1,6-diazabicyclo[3.2.1]octan-6-yl sulfate (130 mg) after lyophilization. The sample was then purified by prep-HPLC using ammonium formate buffer to afford ammonium (2S,5R)-2-(5-(hydroxymethyl)-1,3,4-oxadiazol-2-yl)-7-oxo-1,6-diazabicyclo[3.2.1]octan-6-yl sulfate (30 mg, 27%) as a white solid. ESI-MS (EI⁻, m/z): 319 [M–H]⁻. ¹H-NMR (500M, D₂O): δ 4.79 (s, 2H), 4.80-4.75 (m, 1H), 4.20 (br s, 1H), 3.20 (br d, J=12 Hz, 1H), 2.93 (d, J=12.5 Hz, 1H), 2.29-2.20 (m, 1H), 2.19-2.13 (m, 2H), 1.97-1.95 (m, 1H).

Example 10

Synthesis of (2S,5R)-2-(5-(methylamino)-1,3,4-oxadiazol-2-yl)-7-oxo-1,6-diazabicyclo[3.2.1]octan-6-yl hydrogen sulfate (Compound 203)

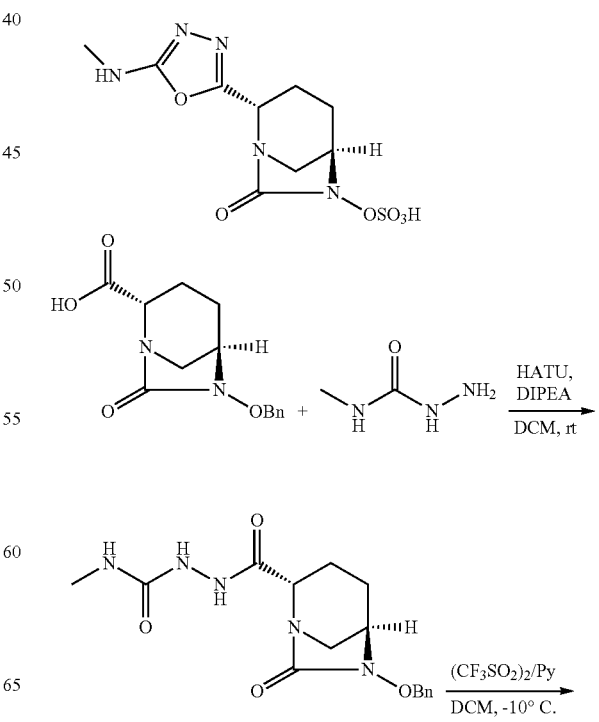

-continued

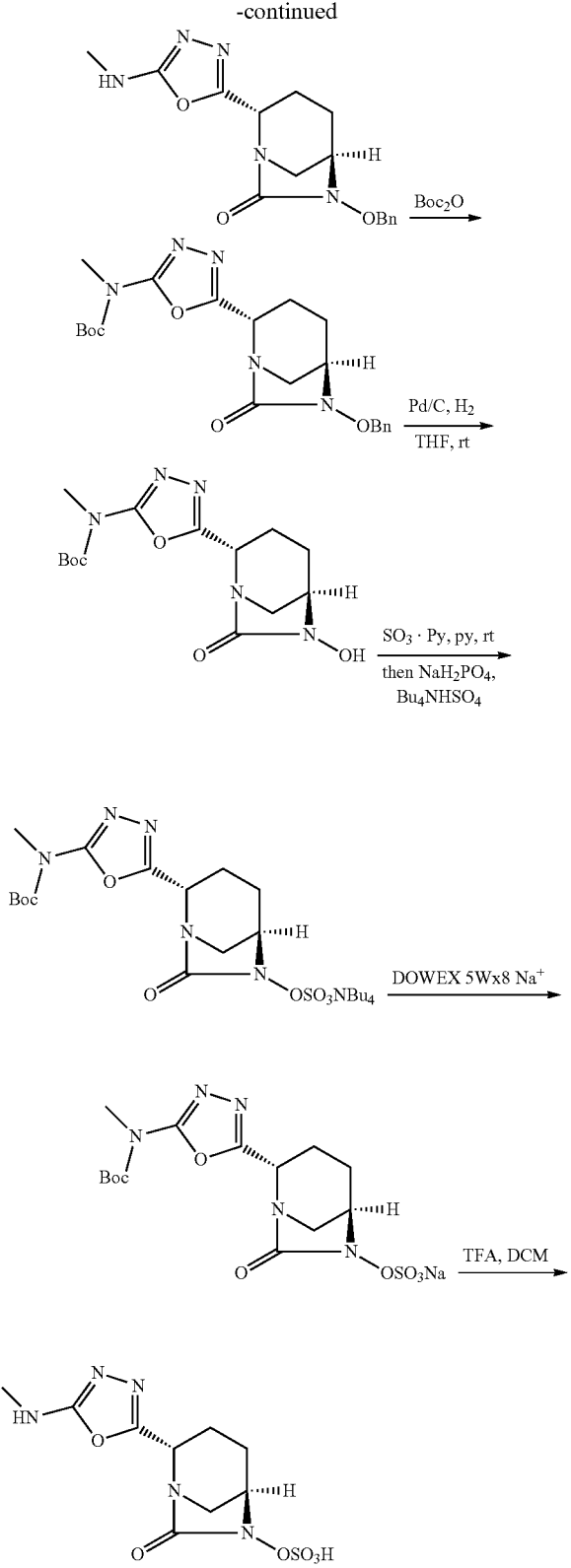

Following the above synthetic scheme and procedures described for similar transformations in other examples, (2S,5R)-2-(5-(methylamino)-1,3,4-oxadiazol-2-yl)-7-oxo-1,6-diazabicyclo[3.2.1]octan-6-yl hydrogen sulfate (23 mg) was obtained as TFA salt. ESI-MS (EI+, m/z): 320.2. $^1$H NMR (300 MHz, D$_2$O) δ 4.64 (d, J=6.3 Hz, 1H), 4.19 (br s, 1H), 3.22-3.18 (m, 1H), 3.03-2.99 (m, 1H), 2.93 (s, 3H), 2.31-1.79 (m, 4H).

Example 11

Synthesis of (2S,5R)-2-(5-(1-methylpiperidin-4-yl)-1,3,4-oxadiazol-2-yl)-7-oxo-1,6-diazabicyclo[3.2.1]octan-6-yl hydrogen sulfate (Compound 204)

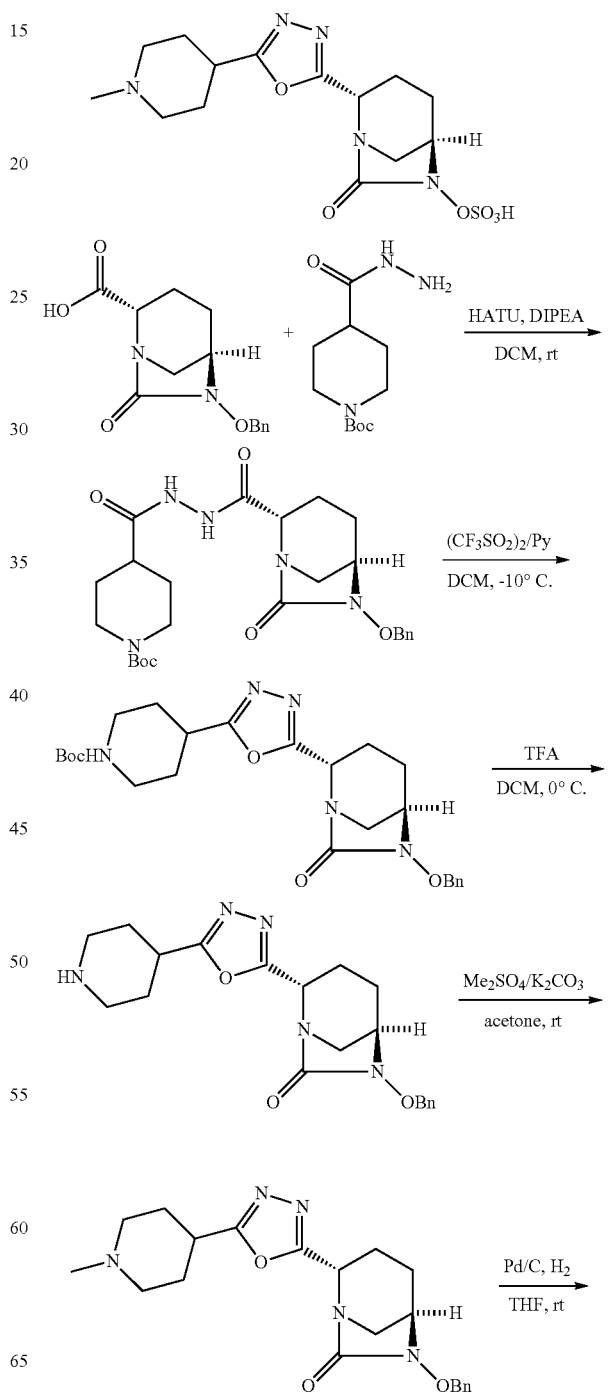

-continued

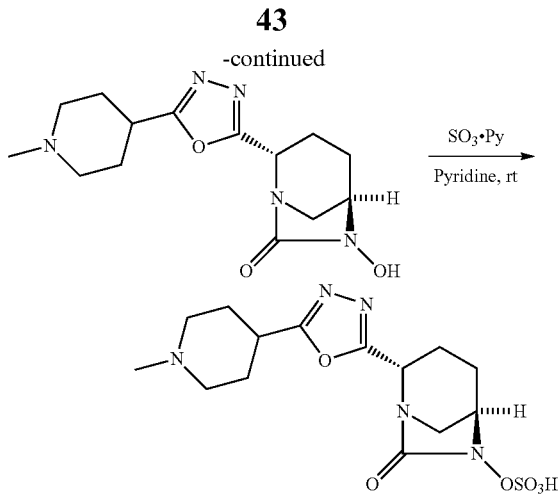

Step 1: Synthesis of tert-butyl 4-(2-((2S,5R)-6-(benzyloxy)-7-oxo-1,6-diaza-bicyclo[3.2.1]octane-2-carbonyl)hydrazinecarbonyl)piperidine-1-carboxylate HATU (3.3 g, 8.7 mmol) and tert-butyl 4-(hydrazinecarbonyl)piperidine-1-carboxylate (2.29 g, 9.42 mmol) were added to a solution of (2S,5R)-6-(benzyloxy)-7-oxo-1,6-diaza-bicyclo[3.2.1]octane-2-carboxylic acid (2.0 g, 7.25 mmol) in CH$_2$Cl$_2$ (50 mL) at 0° C. DIPEA (2.8 g, 21.8 mmol) was then added and the reaction mixture was stirred at 0° C. for 12 hrs. The reaction mixture was then washed with water and saturated sodium chloride and dried over Na$_2$SO$_4$ and concentrated. The residue was purified by silica gel column chromatography (10:1 DCM/MeOH) to give tert-butyl 4-(2-((2S,5R)-6-(benzyloxy)-7-oxo-1,6-diaza-bicyclo[3.2.1]octane-2-carbonyl)hydrazinecarbonyl)piperidine-1-carboxylate (2.2 g, 62%) as a white solid. ESI-MS (EI$^+$, m/z): 502.2 [M+H]$^+$.

Step 2: Synthesis of tert-butyl-4-(5-((2S,5R)-6-(benzyloxy)-7-oxo-1,6-diaza-bicyclo[3.2.1]octan-2-yl)-1,3,4-oxadiazol-2-yl)piperidine-1-carboxylate Pyridine (2.6 mL, 35.0 mmol) was added to a solution of tert-butyl-4-(2-((2S,5R)-6-(benzyloxy)-7-oxo-1,6-diaza-bicyclo[3.2.1]octane-2-carbonyl)hydrazinecarbonyl)piperidine-1-carboxylate (901 mg, 1.8 mmol) in DCM (200 mL). Then, (CF$_3$SO$_2$)$_2$O (2.6 mL, 9.0 mmol) was added slowly at −10° C. The reaction mixture was stirred at rt for 3 hrs then saturated NaHCO$_3$ was added very slowly at −10° C. The organic layer was separated and the aqueous layer was exacted with EtOAc (3×). The combined organic layer was dried over Na$_2$SO$_4$, and concentrated. The crude product was purified by silica gel column chromatography (2:1 EtOAc/hexanes) to give tert-butyl 4-(5-((2S,5R)-6-(benzyloxy)-7-oxo-1,6-diaza-bicyclo[3.2.1]octan-2-yl)-1,3,4-oxadiazol-2-yl)piperidine-1-carboxylate (719 mg, 82%) as a slight yellow solid. ESI-MS (EI$^+$, m/z): 484.2 [M+H]$^+$.

Step 3: Synthesis of (2S,5R)-6-(benzyloxy)-2-(5-(piperidin-4-yl)-1,3,4-oxadiazol-2-yl)-1,6-diaza-bicyclo[3.2.1]octan-7-one CF$_3$COOH (5 mL) was slowly added to a solution of tert-butyl 4-(5-((2S,5R)-6-(benzyloxy)-7-oxo-1,6-diaza-bicyclo[3.2.1]octan-2-yl)-1,3,4-oxadiazol-2-yl)piperidine-1-carboxylate (719 mg, 1.5 mmol) in DCM (20 mL) at 0° C. The mixture was stirred at 0° C. for 3 hrs then, the solvent was concentrated in vacuum to afford (2S,5R)-6-(benzyloxy)-2-(5-(piperidin-4-yl)-1,3,4-oxadiazol-2-yl)-1,6-diaza-bicyclo[3.2.1]octan-7-one (988 mg) as a brown oil, which was used directly in the next step. ESI-MS (EI$^+$, m/z): 384.1 [M+H]$^+$.

Step 4: Synthesis of (2S,5R)-6-(benzyloxy)-2-(5-(1-methylpiperidin-4-yl)-1,3,4-oxadiazol-2-yl)-1,6-diaza-bicyclo[3.2.1]octan-7-one K$_2$CO$_3$ (621 mg, 4.5 mmol) was added to a solution of crude (2S,5R)-6-(benzyloxy)-2-(5-(piperidin-4-yl)-1,3,4-oxadiazol-2-yl)-1,6-diaza-bicyclo[3.2.1]octan-7-one (988 mg) in acetone (30 mL). Me$_2$SO$_4$ (105 μl, 1.6 mmol) was slowly added at 0° C. The mixture was stirred at rt for 6 h, then concentrated and purified by reverse phase column chromatography (gradient elution 0-80% of acetonitrile in water) to give (2S,5R)-6-(benzyloxy)-2-(5-(1-methylpiperidin-4-yl)-1,3,4-oxadiazol-2-yl)-1,6-diaza-bicyclo[3.2.1]octan-7-one (198 mg, 33% for two steps) as a yellow solid. ESI-MS (EI$^+$, m/z): 398.3 [M+H]$^+$.

Step 5: Synthesis of (2S,5R)-6-hydroxy-2-(5-(1-methylpiperidin-4-yl)-1,3,4-oxadiazol-2-yl)-1,6-diaza-bicyclo[3.2.1]octan-7-one To a solution of (2S,5R)-6-(benzyloxy)-2-(5-(1-methylpiperidin-4-yl)-1,3,4-oxadiazol-2-yl)-1,6-diaza-bicyclo[3.2.1]octan-7-one (198 mg, 0.50 mmol) in THF (20 mL) was added 10% Pd/C (200 mg). The mixture was stirred under H$_2$ atmosphere at rt for 3 hrs. The reaction mixture was filtered and concentrated to afford (2S,5R)-6-hydroxy-2-(5-(1-methylpiperidin-4-yl)-1,3,4-oxadiazol-2-yl)-1,6-diaza-bicyclo[3.2.1]octan-7-one (151 mg, 97%), which was used directly in the next step. ESI-MS (EI$^+$, m/z): 308.1 [M+H]$^+$.

Step 6: Synthesis of (2S,5R)-2-(5-(1-methylpiperidin-4-yl)-1,3,4-oxadiazol-2-yl)-7-oxo-1,6-diaza-bicyclo[3.2.1]octane-6-sulfonic acid To a solution of (2S,5R)-6-hydroxy-2-(5-(1-methylpiperidin-4-yl)-1,3,4-oxadiazol-2-yl)-1,6-diaza-bicyclo[3.2.1]octan-7-one (151 mg, 0.5 mmol) in dry pyridine (10 ml) was added SO$_3$.Py (400 mg, 2.5 mmol). The mixture was stirred under N$_2$ atmosphere at rt for 8 hrs. The pyridine was evaporated under vacuum and the residue was purified by prep-HPLC using ammonium formate buffer to give (2S,5R)-2-(5-(1-methylpiperidin-4-yl)-1,3,4-oxadiazol-2-yl)-7-oxo-1,6-diaza-bicyclo[3.2.1]octane-6-sulfonic acid (40 mg, 20%). ESI-MS (EI$^-$, m/z): 386.1 [M−H]$^-$. $^1$H-NMR (500 MHz, D$_2$O): δ 4.76 (d, J=7.0 Hz, 1H), 4.23 (t, J=6.5 Hz, 1H), 4.19 (s, 1H), 4.07 (t, J=6.0 Hz, 1H), 3.61-3.46 (m, 1H), 3.26-3.06 (m, 3H), 2.93-2.90 (m, 1H), 2.82 (s, 3H), 2.36-2.26 (m, 3H), 2.19-2.13 (m, 2H), 2.01-1.91 (m, 3H).

Example 12

Synthesis of (2S,5R)-2-(5-(4-methylpiperazin-1-yl)-1,3,4-oxadiazol-2-yl)-7-oxo-1,6-diazabicyclo[3.2.1]octan-6-yl hydrogen sulfate (Compound 205)

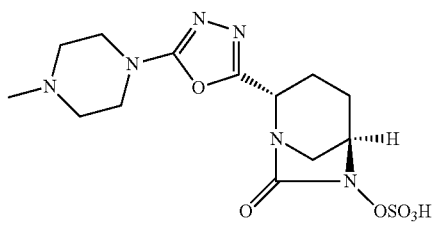

45
-continued

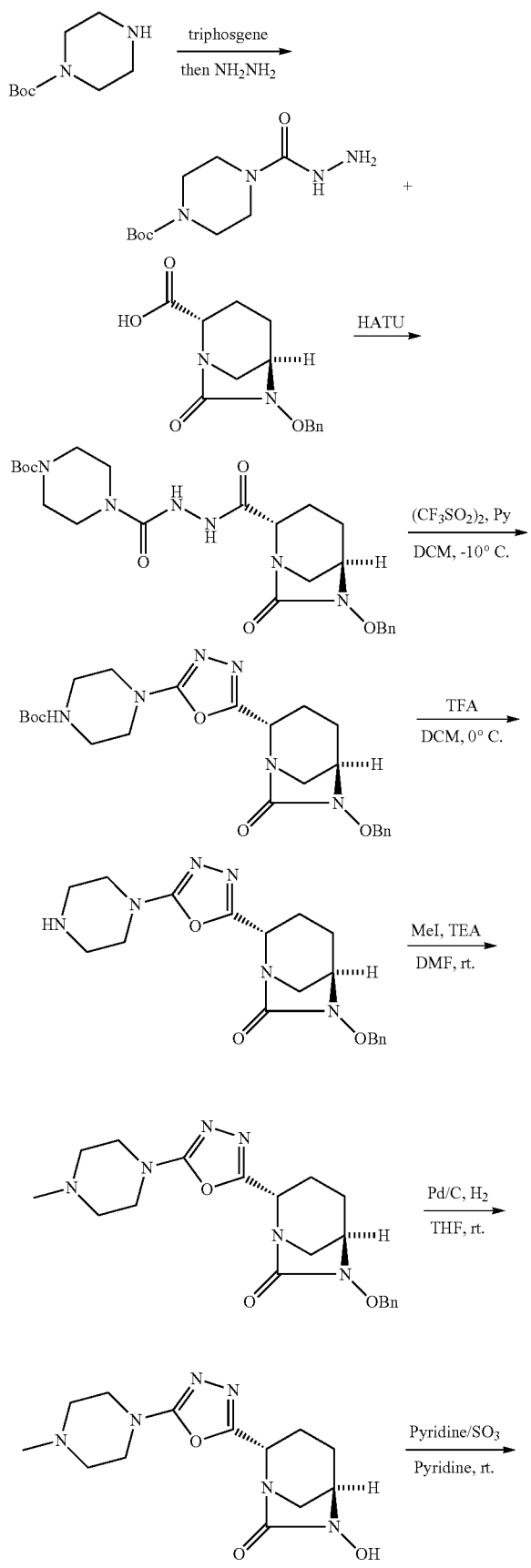

46
-continued

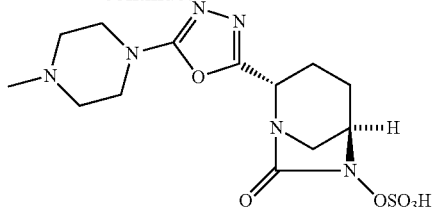

Step 1

DIPEA (105 g, 0.81 mol) was added to a solution of tert-butyl piperazine-1-carboxylate (25.0 g, 0.134 mol) in DCM (250 mL) at 0° C., followed by the addition of triphosgene (92 g, 0.27 mol) in portions over a 40 min time period. The reaction mixture was stirred for at rt for 3 hrs, filtered and concentrated to afford 1-tert-butyl 4-trichloromethyl piperazine-1,4-dicarboxylate (50 g) as an oil. A solution of 1-tert-butyl 4-trichloromethyl piperazine-1,4-dicarboxylate (50 g, 0.145 mol) in THF (50 mL) was added dropwise over a 30 minute period to a solution of hydrazine hydrate (18 mL, 0.434 mol) in THF (150 mL). The reaction mixture was stirred at rt for 2 hrs, diluted with saturated sodium chloride (50 mL) and exacted with EtOAc (3×). The combined organic layer was washed with saturated sodium chloride (2×), dried with $Na_2SO_4$, and concentrated. The residue was purified by crystallization (3:1 petroleum ether/EtOAc) to obtain of tert-butyl 4-(hydrazinecarbonyl)piperazine-1-carboxylate, (13 g, 40% for two steps). ESI-MS (EI$^+$, m/z): 245 [M+H]$^+$. $^1$H-NMR (500 MHz, CDCl$_3$): δ5.92 (s, 1H), 3.45-3.35 (m, 8H), 1.41 (s, 9H).

Step 2

DIPEA (3.7 g, 10 mmol) was added to a solution of (2S,5R)-6-(benzyloxy)-7-oxo-1,6-diaza-bicyclo[3.2.1]octane-2-carboxylic acid (1.45 g, 5.3 mmol) and tert-butyl 4-(hydrazinecarbonyl)piperazine-1-carboxylate, (1.6 g, 6.6 mmol) in dry DMF (50 mL) at 0° C., followed by the addition of HATU (1.45 g, 5.3 mmol). The reaction mixture was stirred at rt overnight. The mixture was diluted with water (200 mL), and the resulting precipitation was collected by filtration, rinsed with water, and then recrystallized (3:1 petroleum ether/EtOAc) to afford tert-butyl 4-(2-((2S,5R)-6-(benzyloxy)-7-oxo-1,6-diazabicyclo[3.2.1]octane-2-carbonyl)hydrazinecarbonyl)piperazine-1-carboxylate (1.4 g, 54%), ESI-MS (EI$^+$, m/z): 503 [M+H]$^+$.

Step 3

Pyridine (2.8 mL, 36.0 mmol was added to a solution of tert-butyl 4-(2-((2S,5R)-6-(benzyloxy)-7-oxo-1,6-diaza-bicyclo[3.2.1]octane-2-carbonyl)hydrazine-carbonyl)piperazine-1-carboxylate (903 mg, 1.8 mmol) in DCM (200 mL). $(CF_3SO_2)_2O$ (2.8 ml, 9.0 mmol) was then added slowly at −10° C. The reaction mixture was stirred at rt for 3 hrs. Saturated NaHCO$_3$ was added at −10° C. very slowly. The combined organic layer was separated and the aqueous layer was exacted with EtOAc (3×). The combined organic layer was dried over Na$_2$SO$_4$, and concentrated. The crude product was purified by silica gel column chromatography (2:1 EtOAc/hexanes) to give tert-butyl 4-(5-((2S,5R)-6-(benzyloxy)-7-oxo-1,6-diaza-bicyclo[3.2.1]octan-2-yl)-1,3,4-oxadiazol-2-yl)piperazine-1-carboxylate (723 mg, 83%) as a slight yellow solid. ESI-MS (EI$^+$, m/z): 485.2 [M+H]$^+$.

Step 4: Synthesis of (2S,5R)-6-(benzyloxy)-2-(5-(piperazin-1-yl)-1,3,4-oxadiazol-2-yl)-1,6-diaza-bicyclo[3.2.1]octan-7-one CF$_3$COOH (5 mL) was slowly added at 0° C. to a solution of tert-butyl 4-(5-((2S,5R)-6-(benzyl-oxy)-7-oxo-1,6-diazabicyclo[3.2.1]octan-2-yl)-1,3,4-oxadiazol-2-yl)piperazine-1 carboxylate (723 mg, 1.5 mmol) in DCM (20 mL). The mixture was stirred at 0° C. for 3 hrs, then, the solvent was concentrated to afford (2S,5R)-6-(benzyloxy)-2-(5-(piperazin-1-yl)-1,3,4-oxadiazol-2-yl)-1,6-diaza-bicyclo[3.2.1]octan-7-one (997 mg) as a brown oil, which was used directly in the next step. ESI-MS (EI$^+$, m/z): 385.1 [M+H]$^+$.

Step 5: Synthesis of (2S,5R)-6-(benzyloxy)-2-(5-(4-methylpiperazin-1-yl)-1,3,4-oxadiazol-2-yl)-1,6-diaza-bicyclo[3.2.1]octan-7-one Et$_3$N (631 µL, 4.5 mmol) was added to a solution of crude (2S,5R)-6-(benzyloxy)-2-(5-(piperazin-1-yl)-1,3,4-oxadiazol-2-yl)-1,6-diazabicyclo[3.2.1]octan-7-one (997 mg) in DMF (15 mL). Then, MeI (106 µL, 1.6 mmol) was slowly added at 0° C. The mixture was stirred at rt for 6 hrs then, the mixture was concentrated and purified by reverse phase column chromatography (gradient elution, 0 to 80% of acetonitrile in water) to give (2S,5R)-6-(benzyloxy)-2-(5-(4-methylpiperazin-1-yl)-1,3,4-oxadiazol-2-yl)-1,6-diaza-bicyclo[3.2.1]octan-7-one (202 mg, 34% for two steps) as a yellow solid. ESI-MS (EI$^+$, m/z): 399.3 [M+H]$^+$.

Step 6: Synthesis of (2S,5R)-6-hydroxy-2-(5-(4-methylpiperazin-1-yl)-1,3,4-oxadiazol-2-yl)-1,6diaza-bicyclo[3.2.1]octan-7-one To a solution of (2S,5R)-6-(benzyloxy)-2-(5-(4-methylpiperazin-1-yl)-1,3,4-oxadiazol-2-yl)-1,6-diaza-bicyclo[3.2.1]octan-7-one (202 mg, 0.51 mmol) in THF (150 mL) was added 10% Pd/C (300 mg). The mixture was stirred under H$_2$ atmosphere at rt for 3 hrs then filtered and concentrated to afford (2S,5R)-6-hydroxy-2-(5-(4-methylpiperazin-1-yl)-1,3,4-oxadiazol-2-yl)-1,3,4-oxadiazol-2-yl)-1,6-diaza-bicyclo[3.2.1]octan-7-one (154 mg, 98%), which was used directly in the next step. ESI-MS (EI$^+$, m/z): 309.1 [M+H]$^+$.

Step 5: Synthesis of (2S,5R)-2-(5-(4-methylpiperazin-1-yl)-1,3,4-oxadiazol-2-yl)-7-oxo-1,6-diazabicyclo[3.2.1]octan-6-yl hydrogen sulfate To a solution of (2S,5R)-6-hydroxy-2-(5-(4-methylpiperazin-1-yl)-1,3,4-oxadiazol-2-yl)-1,6-diaza-bicyclo[3.2.1]octan-7-one (154 mg, 0.5 mmol) in dried pyridine (10 mL) was added SO$_3$.Py (400 mg, 2.5 mmol). The mixture was stirred under N$_2$ atmosphere at rt for 8 hrs. The pyridine was evaporated under vacuum at 40° C., then, the mixture was concentrated and purified by pre-HPLC using ammonium formate buffer to give (2S,5R)-2-(5-(4-methylpiperazin-1-yl)-1,3,4-oxadiazol-2-yl)-7-oxo-1,6-diazabicyclo[3.2.1]octan-6-yl hydrogen sulfate (45 mg, 23%). ESI-MS (EI$^-$, m/z): 387.1 [M−H]$^-$. $^1$H-NMR (500 MHz, D$_2$O): δ 4.62 (d, J=7.0 Hz, 1H), 4.16 (br s, 1H), 3.89 (br s, 4H), 3.31 (br s, 4H), 3.16 (br d, J=12.0 Hz, 1H), 2.95 (d, J=12.0 Hz, 1H), 2.82 (s, 3H), 2.20-2.17 (m, 1H), 2.12-2.05 (m, 2H), 1.94-1.87 (m, 1H).

Example 13

Synthesis of (2S,5R)-2-(5-(morpholin-2-yl)-1,3,4-oxadiazol-2-yl)-7-oxo-1,6-diazabicyclo[3.2.1]octan-6-yl hydrogen sulfate (Compound 206)

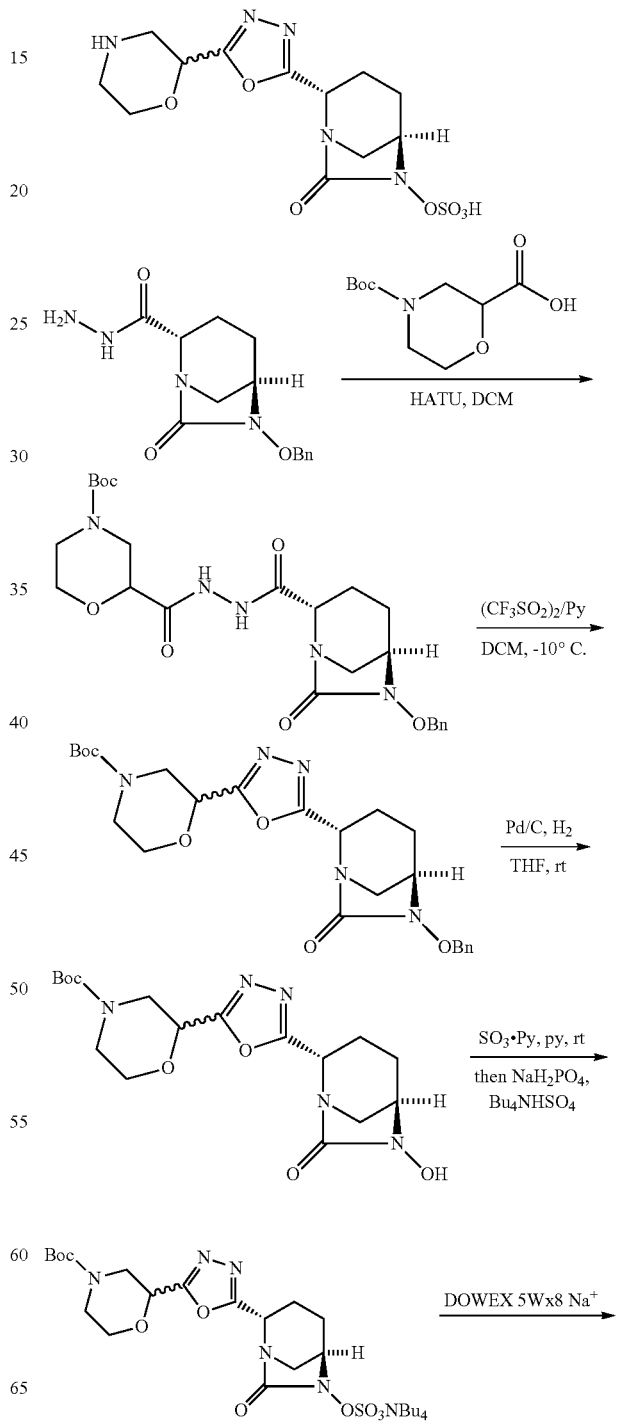

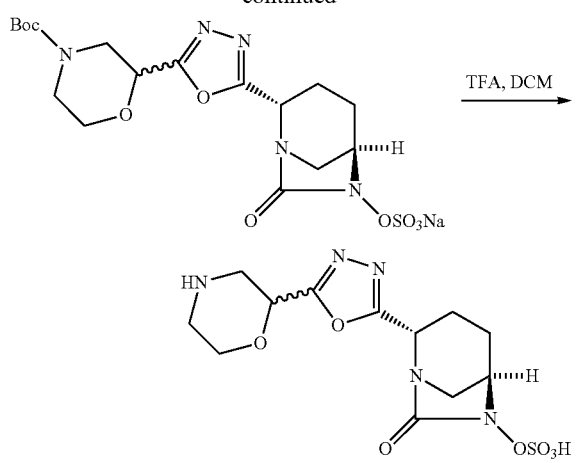

Following the above synthetic scheme and procedures described for similar transformations in other examples, (2S, 5R)-2-(5-(morpholin-2-yl)-1,3,4-oxadiazol-2-yl)-7-oxo-1,6-diazabicyclo[3.2.1]octan-6-yl hydrogen sulfate (22 mg) was obtained as TFA salt. ESI-MS (EI+, m/z): 376.15. $^1$H NMR (300 MHz, D$_2$O) δ 5.32 (dd, J=9.7, 3.1 Hz, 1H), 4.82 (d, J=5.7 Hz, 1H), 4.24-4.12 (m, 2H), 4.07-3.98 (m, 1H), 3.78-3.73 (m, 1H), 3.61-3.54 (m, 1H), 3.44-3.28 (m, 2H), 3.25-3.19 (m, 1H), 2.95 (d, J=12.4 Hz, 1H), 2.36-2.07 (m, 3H), 1.99-1.92 (m, 1H).

Example 14

Synthesis of (2S,5R)-2-(5-morpholino-1,3,4-oxadiazol-2-yl)-7-oxo-1,6-diazabicyclo[3.2.1]octan-6-yl hydrogen sulfate (Compound 207)

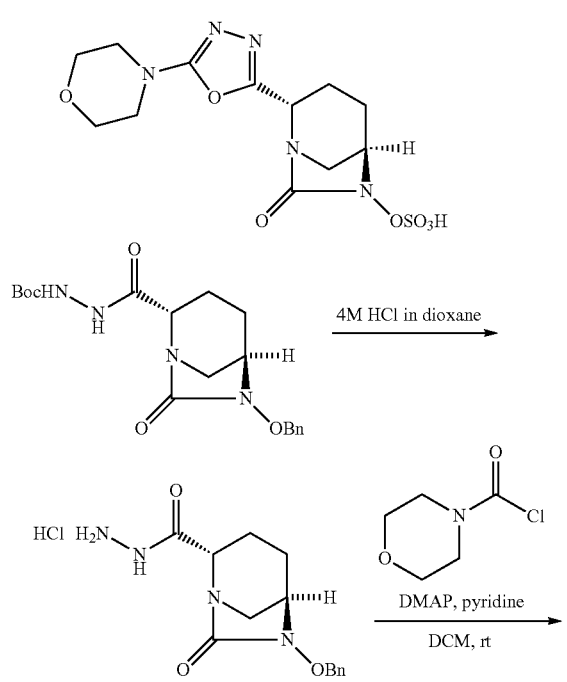

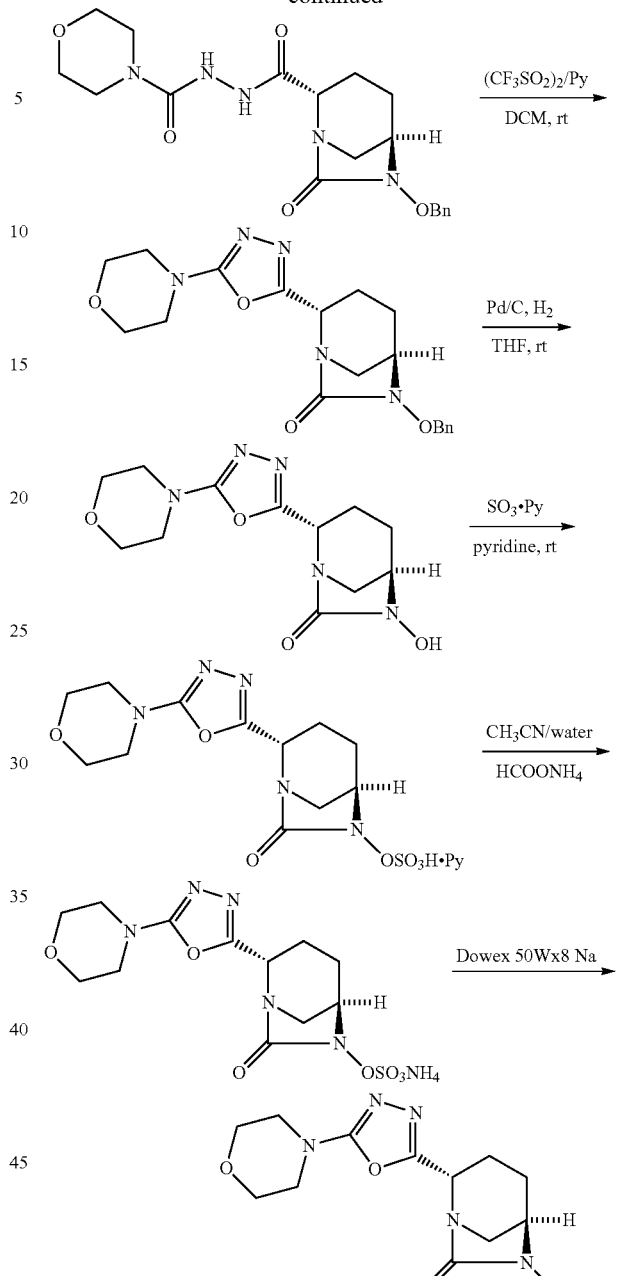

Step 1

To a solution of tert-butyl 2-((2S,5R)-6-(benzyloxy)-7-oxo-1,6-diaza-bicyclo[3.2.1]octane-2-carbonyl)hydrazinecarboxylate (0.78 g, 2.0 mmol) in dioxane (10 mL) was added 4M HCl in dioxane (5 mL) at 0° C. The reaction mixture was stirred at rt for 1 h, then, Et$_2$O (10 mL) was added. The solid precipitation was collected by filtration, washed with Et$_2$O (2×), and dried under vacuum to provide (2S,5R)-6-(benzyloxy)-7-oxo-1,6-diaza-bicyclo[3.2.1]octane-2-carbohydrazide hydrochloride (0.65 g, 99%), which was used directly in the next step. ESI-MS (EI+, m/z): 291.19 [M+H]+.

Step 2

Morpholine-4-carbonyl chloride (297 mg, 1.99 mmol) was added dropwise over a period of 10 minutes to a solution of DMAP (24 mg, 0.199 mmol) and pyridine (0.16 mL, 1.99 mmol) in dry DCM (5 mL). The mixture was stirred at 0° C. for 20 minutes then, a solution of (2S,5R)-6-(benzyloxy)-7-oxo-1,6-diaza-bicyclo[3.2.1]octane-2-carbohydrazide hydrochloride (0.65 g, 1.99 mmol) in dry DCM (2.0 mL) was added over a period of 10 minutes. The mixture was stirred at 0° C. for 15 min and was then allowed to warm to rt and was stirred overnight. The reaction mixture was diluted with DCM (10 mL), and washed with 1N HCl (10 mL), and saturated sodium chloride (10 mL), then was dried over $Na_2SO_4$ and concentrated. The crude product was purified by silica gel column chromatography (0 to 1:100 MeOH/DCM, containing 1% TEA) to give N'-((2S,5R)-6-(benzyloxy)-7-oxo-1,6-diaza-bicyclo[3.2.1]octane-2-carbonyl)morpholine-4-carbohydrazide (0.38 g, 47%) as a white solid. ESI-MS (EI+, m/z): 404.19 [M+H]+.

Step 3

Pyridine (2.0 mL) was added to a solution of N'-(2S,5R)-6-(benzyloxy)-7-oxo-1,6-diaza-bicyclo[3.2.1]octane-2-carbonyl)morpholine-4-carbohydrazide (0.38 g, 0.94 mmol) in dry DCM (10 mL). $(CF_3SO_2)_2O$ (2.0 mL) was then added slowly at −10° C. The reaction mixture was stirred at rt for 0.5 h then saturated $NaHCO_3$ was added at −10° C. very slowly. The organic layer was separated and the aqueous layer was exacted with EtOAc (3×). The combined organic layer was dried with $Na_2SO_4$, concentrated, and purified by silica gel column chromatography (0 to 1:50 MeOH/DCM) to give (2S,5R)-6-(benzyloxy)-2-(5-morpholino-1,3,4-oxadiazol-2-yl)-1,6-diaza-bicyclo[3.2.1]octan-7-one (0.12 g, 33%). ESI-MS (EI+, m/z): 386 [M+H]+.

Step 4

A mixture of (2S,5R)-6-(benzyloxy)-2-(5-morpholino-1,3,4-oxadiazol-2-yl)-1,6-diaza-bicyclo[3.2.1]octan-7-one (0.12 g) and 10% Pd/C (70 mg) in THF (5 mL) was stirred at rt under $H_2$ atmosphere for 1-2 hrs. The reaction mixture was then filtered and concentrated to afford (2S,5R)-6-hydroxy-2-(5-morpholino-1,3,4-oxadiazol-2-yl)-1,6-diaza-bicyclo[3.2.1]octan-7-one (83 mg, 90%), which was used directly in the next step. ESI-MS (EI+, m/z): 296 [M+H]+.

Step 5

To a solution of (2S,5R)-6-hydroxy-2-(5-morpholino-1,3,4-oxadiazol-2-yl)-1,6-diaza-bicyclo[3.2.1]octan-7-one (83 mg, 0.28 mmol) in dried pyridine (2 mL) was added $SO_3$·Py (224 mg, 1.41 mmol). The mixture was stirred at rt for 3 hrs. then the pyridine was evaporated under vacuum. The residue was purified by prep-HPLC using ammonium formate buffer to give ammonium (2S,5R)-2-(5-morpholino-1,3,4-oxadiazol-2-yl)-7-oxo-1,6-diazabicyclo[3.2.1]octan-6-yl sulfate (70 mg) as a white solid. ESI-MS (EI−, m/z): 374.0 [M−H]−; 1H-NMR (500 MHz, $D_2O$): δ 4.63-4.61 (m, 1H), 4.17 (m, 1H), 3.77-3.75 (m, 4H), 3.47-3.45 (m, 4H), 3.16 (d, J=12.0 Hz, 1H), 2.95 (d, J=12.5 Hz, 1H), 2.21-2.17 (m, 1H), 2.09 (m, 2H), 1.95-1.90 (m, 1H).

Step 6: Resin Exchange

Ammonium (2S,5R)-2-(5-morpholino-1,3,4-oxadiazol-2-yl)-7-oxo-1,6-diazabicyclo[3.2.1]octan-6-yl sulfate (70 mg) was dissolved in a minimum amount of water and passed through a column of 2 g of DOWEX 50Wx8 Na+ resin (the resin was pre-washed with HPLC grade of water to neutral) and eluted with HPLC grade water to afford sodium (2S,5R)-2-(5-morpholino-1,3,4-oxadiazol-2-yl)-7-oxo-1,6-diazabicyclo[3.2.1]octan-6-yl sulfate (65 mg) as a white solid after lyophilization. ESI-MS (EI−, m/z): 374.0 [M−H]−; 1H-NMR (500 MHz, $D_2O$): δ 4.71 (d, J=7.0 Hz, 1H), 4.27 (m, 1H), 3.87-3.85 (-m, 4H), 3.56-3.54 (m, 4H), 3.27-3.25 (m, 1H), 3.05 (d, J=12.0 Hz, 1H), 2.31-2.29 (m, 1H), 2.20-2.17 (m, 2H), 2.03-2.00 (m, 1H).

Example 15

Synthesis of (2S,5R)-7-oxo-2-(1,3,4-thiadiazol-2-yl)-1,6-diazabicyclo[3.2.1]octan-6-yl hydrogen sulfate (Compound 300)

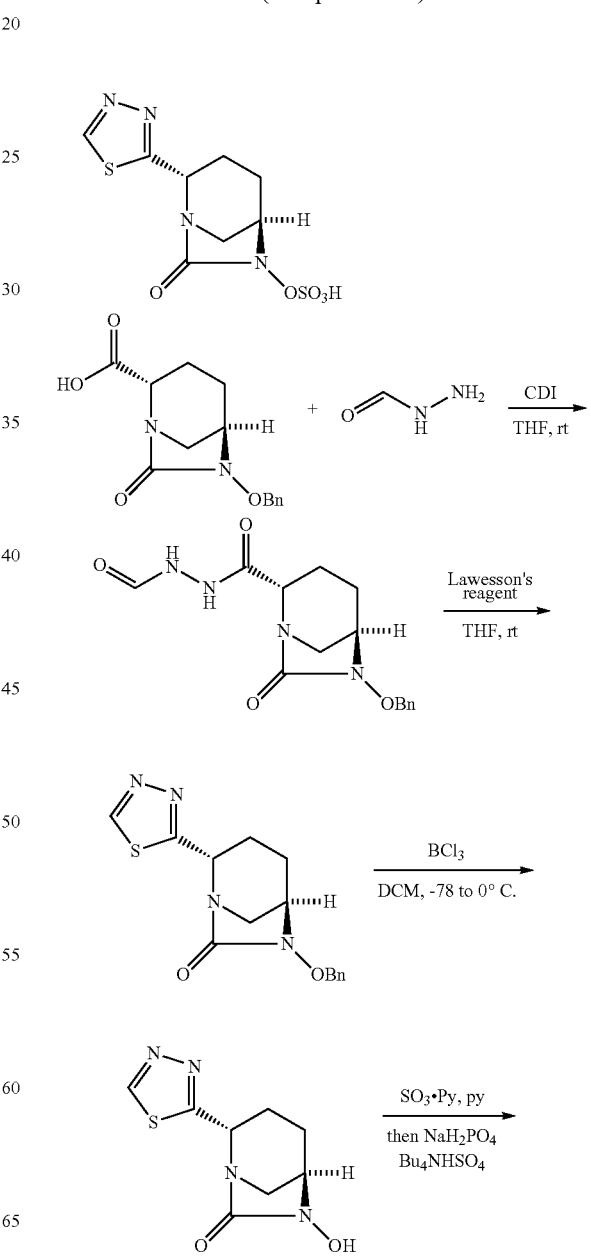

-continued

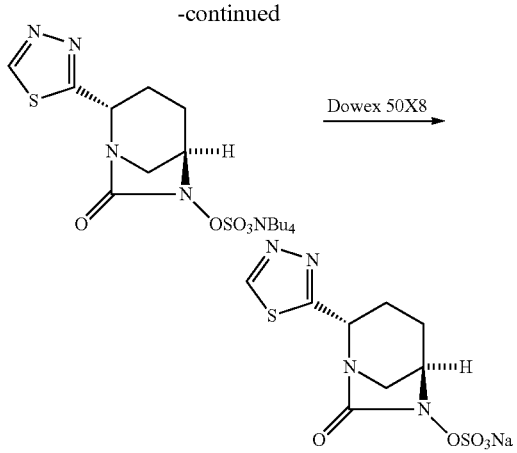

Step 1: Synthesis of (2S,5R)-6-(Benzyloxy)-N'-formyl-7-oxo-1,6-diaza-bicyclo[3.2.1]octane-2-carbohydrazide To a solution of (2S,5R)-6-(benzyloxy)-7-oxo-1,6-diazabicyclo[3.2.1]octane-2-carboxylic acid (1.0 g, 6.0 mmol) in THF (30 mL) was added 1,1'-carbonyldiimidazole (1.6 g, 7.2 mmol) at 0° C. The reaction mixture was stirred at rt for 1 h, then, formohydrazide (1.1 g, 18.1 mmol) was added rapidly at rt. The reaction mixture was stirred at rt for 3 hrs and then diluted with EtOAc (100 mL). The combined organic layer was washed with saturated sodium chloride (10 mL), dried over $Na_2SO_4$, and concentrated to afford (2S,5R)-6-(benzyloxy)-N'-formyl-7-oxo-1,6-diaza-bicyclo[3.2.1]octane-2-carbohydrazide (1.6 g), which was used directly in the next step. ESI-MS (EI$^+$, m/z): 319.1 [M+H]$^+$.

Step 2: Synthesis of (2S,5R)-6-(benzyloxy)-2-(1,3,4-thiadiazol-2-yl)-1,6-diaza-bicyclo[3.2.1]octan-7-one Lawesson's reagent (2.40 g, 6.0 mmol) was added to a solution of (2S,5R)-6-(benzyloxy)-N'-formyl-7-oxo-1,6-diaza-bicyclo[3.2.1]octane-2-carbohydrazide (1.6 g, 6.0 mmol) in THF (30 mL) at rt. The mixture was stirred at rt for 8 hrs., then the solvent was concentrated and the residue was purified by silica gel column chromatography (1:6 to 1:1 EtOAc/hexanes) to give (2S,5R)-6-(benzyloxy)-2-(1,3,4-thiadiazol-2-yl)-1,6-diaza-bicyclo[3.2.1]octan-7-one (568 mg, 30%) as a yellow solid. ESI-MS (EI$^+$, m/z): 317.1 [M+H]$^+$. $^1$H-NMR (400 MHz, CDCl$_3$): δ 9.12 (s, 1H), 7.38-7.29 (m, 5H), 5.02 (d, J=8.8 Hz, 1H), 4.89-4.83 (m, 2H), 3.28 (m, 1H), 2.86-2.83 (m, 1H), 2.70-2.54 (m, J=2H), 2.29-2.24 (m, 1H), 2.17-2.13 (m, 1H), 2.07-1.79 (m, 1H).

Step 3: Synthesis of (2S,5R)-6-hydroxy-2-(1,3,4-thiadiazol-2-yl)-1,6-diaza-bicyclo[3.2.1]octan-7-one BCl$_3$ (1 M in CH$_2$Cl$_2$, 9.0 mL, 9.0 mmol) was added dropwise to a solution of (2S,5R)-6-(benzyloxy)-2-(1,3,4-thiadiazol-2-yl)-1,6-diaza-bicyclo[3.2.1]octan-7-one (560 mg, 1.8 mmol) in dry CH$_2$Cl$_2$ (20 mL) at −78° C. The mixture was stirred under a N$_2$ atmosphere at 0° C. for 6 hrs., then, MeOH (9 mL) was slowly added dropwise at −78° C. The solvents were evaporated under vacuum at 0° C. to give (2S,5R)-6-hydroxy-2-(1,3,4-thiadiazol-2-yl)-1,6-diaza-bicyclo[3.2.1]octan-7-one (329 mg, 81%) as a yellow solid, which was used directly in the next step. ESI-MS (EI$^−$, m/z): 227.1 [M+H]$^−$.

Step 4: Synthesis of tetrabutylammonium (2S,5R)-7-oxo-2-(1,3,4-thiadiazol-2-yl)-1,6-diaza-bicyclo[3.2.1]octan-6-yl sulfate To a solution of crude (2S,5R)-6-hydroxy-2-(1,3,4-thiadiazol-2-yl)-1,6-diaza-bicyclo[3.2.1]octan-7-one (329 mg) in dried pyridine (15 mL) was added SO$_3$.Py (1.2 g, 7.0 mmol). The mixture was stirred under N$_2$ atmosphere at rt for 6 hrs., then the pyridine was evaporated under vacuum at 40° C. The residue was redissolved in aqueous NaH$_2$PO$_4$ (1.5 M, 50 mL) and tetra-butylammonium hydrogensulphate (609 mg, 1.9 mmol) was added. The mixture was stirred at rt for 20 min, and extracted with EtOAc (4×). The combined organic layer was dried and concentrated and the residue was purified by silica gel column chromatography (10:1 to 2:1 DCM/acetone) to give tetrabutylammonium (2S,5R)-7-oxo-2-(1,3,4-thiadiazol-2-yl)-1,6-diaza-bicyclo[3.2.1]octan-6-yl sulfate (313 mg, 41% for two steps) as a yellow solid. ESI-MS (EI$^−$, m/z): 305.0 [M−H]$^−$. $^1$H-NMR (400 MHz, CDCl$_3$): δ 9.19 (s, 1H), 4.85 (d, J=5.6 Hz, 1H), 4.38 (s, 1H), 3.32-3.24 (m, 9H), 2.75-2.64 (m, 2H), 2.31-1.29 (m, 3H), 1.83-1.91 (m, 1H), 1.71-1.65 (m, 8H), 1.50-1.43 (m, 8H), 1.02 (t, J=5.6 Hz, 12H).

Step 6: Resin Exchange

Tetrabutylammonium (2S,5R)-7-oxo-2-(1,3,4-thiadiazol-2-yl)-1,6-diaza-bicyclo[3.2.1]octan-6-yl sulfate (140 mg) was dissolved in a minimum amount of HPLC grade water (~10 mL) and passed through a column of 10 g of DOWEX 50WX 8 Na$^+$ resin (the resin was pre-washed with >0.5 L of HPLC grade water to neutral) and eluted with HPLC grade water to afford sodium (2S,5R)-7-oxo-2-(1,3,4-thiadiazol-2-yl)-1,6-diaza-bicyclo[3.2.1]octan-6-yl sulfate after lyophilization as a white solid (68 mg). ESI-MS (EI$^−$, m/z): 305.0 [M−H]$^−$. $^1$H-NMR (400 MHz, CDCl$_3$): δ 9.49 (s, 1H), 5.00 (d, J=5.6 Hz, 1H), 4.20 (br s, 1H), 3.19 (br d, J=9.6 Hz, 1H), 2.92 (d, J=12.0 Hz, 1H), 2.55-2.51 (m, 1H), 1.26-1.15 (m, 2H), 1.97-1.90 (m, 1H).

Example 16

Synthesis of (2S,5R)-2-(5-(aminomethyl)-1,3,4-thiadiazol-2-yl)-7-oxo-1,6-diazabicyclo[3.2.1]octan-6-yl hydrogen sulfate (Compound 301)

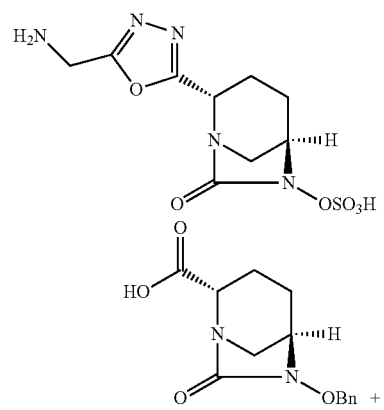

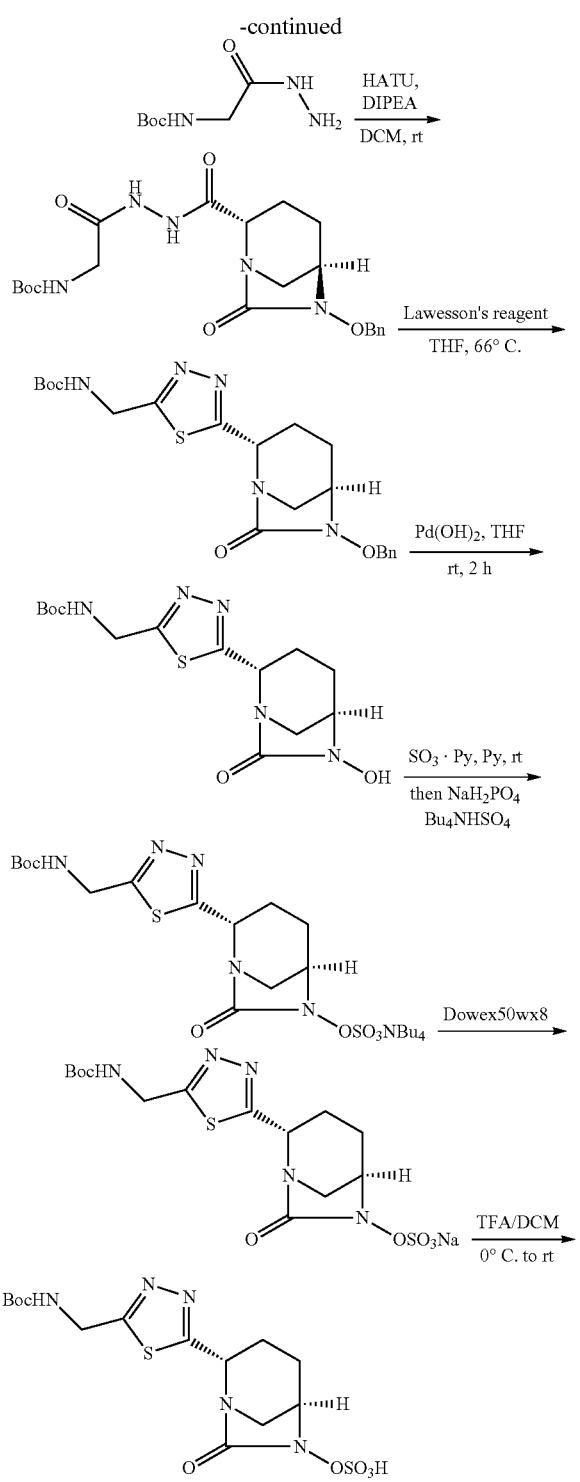

Step 1

HATU (4.9 g, 12.9 mmol) and tert-butyl 2-hydrazinyl-2-oxoethylcarbamate (2.2 g, 11.4 mmol) were added to a solution of (2S,5R)-6-(benzyloxy)-7-oxo-1,6-diaza-bicyclo[3.2.1]octane-2-carboxylic acid (3 g, 10.8 mmol) in $CH_2Cl_2$ (50 mL) at 0° C. DIPEA (4.2 g, 32.6 mmol) was then added and the reaction mixture was stirred at 0° C. for 12 hrs. The reaction mixture was then washed with water, and saturated sodium chloride, dried over $Na_2SO_4$, and concentrated. The crude sample was purified by silica gel column chromatography (1 to 10% MeOH/DCM) to give tert-butyl (2-(2-((2S,5R)-6-(benzyloxy)-7-oxo-1,6-diazabicyclo[3.2.1]octane-2-carbonyl)hydrazinyl)-2-oxoethyl)carbamate (3.5 g, 62%) as a white solid. ESI-MS (EI$^+$, m/z): 448.2 [M+H]$^+$.

Step 2

Lawesson's reagent (0.68 g, 1.68 mol) was added to a solution of tert-butyl 2-(2-((2S,5R)-6-(benzyloxy)-7-oxo-1,6-diaza-bicyclo[3.2.1]octane-2-carbonyl)hydrazinyl)-2-oxoethylcarbamate (0.50 g, 1.12 mmol) in THF (30 mL). The reaction mixture was heated at 70° C. for 0.5 h. The solution was cooled down to rt and saturated $NaHCO_3$ was added. The organic layer was separated and the aqueous layer was exacted with EtOAc (2×). The combined organic layer was dried over $Na_2SO_4$, and concentrated. The crude sample was dissolved in THF (100 mL), and $Hg(OAc)_2$ (1.68 g) was added. The mixture was stirred at rt overnight, filtered and concentrated. The residue was dissolved in EtOAc (100 mL), stirred for 30 min, filtered and concentrated. The crude material was purified by silica gel column chromatography (20% to 50% EtOAc/petroleum ether) to give tert-butyl ((5-((2S,5R)-6-(benzyloxy)-7-oxo-1,6-diazabicyclo[3.2.1]octan-2-yl)-1,3,4-thiadiazol-2-yl)methyl)carbamate (230 mg, 45%) as a white solid. ESI-MS (EI$^+$, m/z): 446.2 [M+H]$^+$.

Step 3

To a solution of tert-butyl ((5-((2S,5R)-6-(benzyloxy)-7-oxo-1,6-diazabicyclo[3.2.1]octan-2-yl)-1,3,4-thiadiazol-2-yl)methyl)carbamate (400 mg, 0.89 mmol) in THF (60 mL) was added 10% $Pd(OH)_2C$ (3 g). The mixture was stirred under $H_2$ atmosphere at rt for 3 hrs. The reaction mixture was filtered and concentrated to afford tert-butyl ((5-((2S,5R)-6-hydroxy-7-oxo-1,6-diazabicyclo[3.2.1]octan-2-yl)-1,3,4-thiadiazol-2-yl)methyl)carbamate as a yellow solid, which was directly used in the next step. ESI-MS (EI$^+$, m/z): 356.1 [M+H]$^+$.

Step 4

To a solution of tert-butyl ((5-((2S,5R)-6-hydroxy-7-oxo-1,6-diazabicyclo[3.2.1]octan-2-yl)-1,3,4-thiadiazol-2-yl)methyl)carbamate in dry pyridine (3 mL) was added $SO_3 \cdot Py$ (990 mg, 6.23 mmol). The mixture was stirred at rt for 3 hrs., then the pyridine was evaporated under vacuum at 25° C. The residue was redissolved in aqueous $NaH_2PO_4$ (1.5 M, 20 mL), then tetrabutylammonium hydrogensulphate (150 mg) was added. The mixture was stirred at rt for 20 minutes then extracted with EtOAc (4×). The combined organic layer was dried and concentrated and the residue was purified by silica gel column chromatography (10:1 to 1:1 DCM/acetone) to give tetrabutylammonium (2S,5R)-2-(5-(((tert-butoxycarbonyl)amino)methyl)-1,3,4-thiadiazol-2-yl)-7-oxo-1,6-diazabicyclo[3.2.1]octan-6-yl sulfate (100 mg, 20% in 3 steps) as a light yellow solid. ESI-MS (EI$^-$, m/z): 434.1 [M−H]$^-$.

Step 5

Tetrabutylammonium (2S,5R)-2-(5-(((tert-butoxycarbonyl)amino)methyl)-1,3,4-thiadiazol-2-yl)-7-oxo-1,6-diazabicyclo[3.2.1]octan-6-yl sulfate (95 mg, 0.14 mmol) was dissolved in a minimum amount of HPLC grade water (~10 mL) and passed through a column of 16 g of DOWEX 50WX 8 Na$^+$ resin (the resin was pre-washed with >0.5 L of HPLC grade water) and eluted with HPLC grade water. Sodium (2S,5R)-2-(5-(((tert-butoxycarbonyl)amino)methyl)-1,3,4-thiadiazol-2-yl)-7-oxo-1,6-diazabicyclo[3.2.1]octan-6-yl sulfate (53 mg, 80%) was obtained after lyophilization as a white solid. ESI-MS (EI⁻, m/z): 434.0 [M−H]⁻. ¹H-NMR (500 MHz, D₂O) δ 4.86 (d, J=6.5 Hz, 1H), 4.55 (s, 2H), 4.12 (s, 1H), 3.10-3.13 (m, 1H), 2.87-2.89 (m, 1H), 2.39-2.43 (m, 1H), 2.07-2.12 (m, 2H), 1.84-1.86 (m, 1H), 1.31 (s, 9H).

Step 6

TFA (0.30 mL) was added to a mixture of sodium (2S,5R)-2-(5-(((tert-butoxycarbonyl)amino)methyl)-1,3,4-thiadiazol-2-yl)-7-oxo-1,6-diazabicyclo[3.2.1]octan-6-yl sulfate (50 mg) in dry DCM (0.80 mL) at 0° C. The reaction mixture was stirred at 0° C. for 2-3 hrs and then diluted with ether (~15 mL). The precipitate was collected via centrifugation, washed with ether (3×) and dried under high vacuum to afford (2S,5R)-2-(5-(aminomethyl)-1,3,4-thiadiazol-2-yl)-7-oxo-1,6-diazabicyclo[3.2.1]octan-6-yl hydrogen sulfate (30 mg) as TFA salt. ESI-MS (EI⁺, m/z): 336.1. ¹H NMR (300 MHz, D₂O) δ 4.97 (br d, J=6.2 Hz, 1H), 4.68 (s, 2H), 4.19 (br s, 1H), 3.21 (br d, J=13.5 Hz, 1H), 2.94 (d, J=12.2 Hz, 1H), 2.54-2.49 (m, 1H), 2.30-2.07 (m, 2H), 1.98-1.87 (m, 1H).

Example 17

Synthesis of (2S,5R)-7-oxo-2-(5-(piperazin-1-yl)-1,3,4-thiadiazol-2-yl)-1,6-diazabicyclo[3.2.1]octan-6-yl hydrogen sulfate (Compound 302)

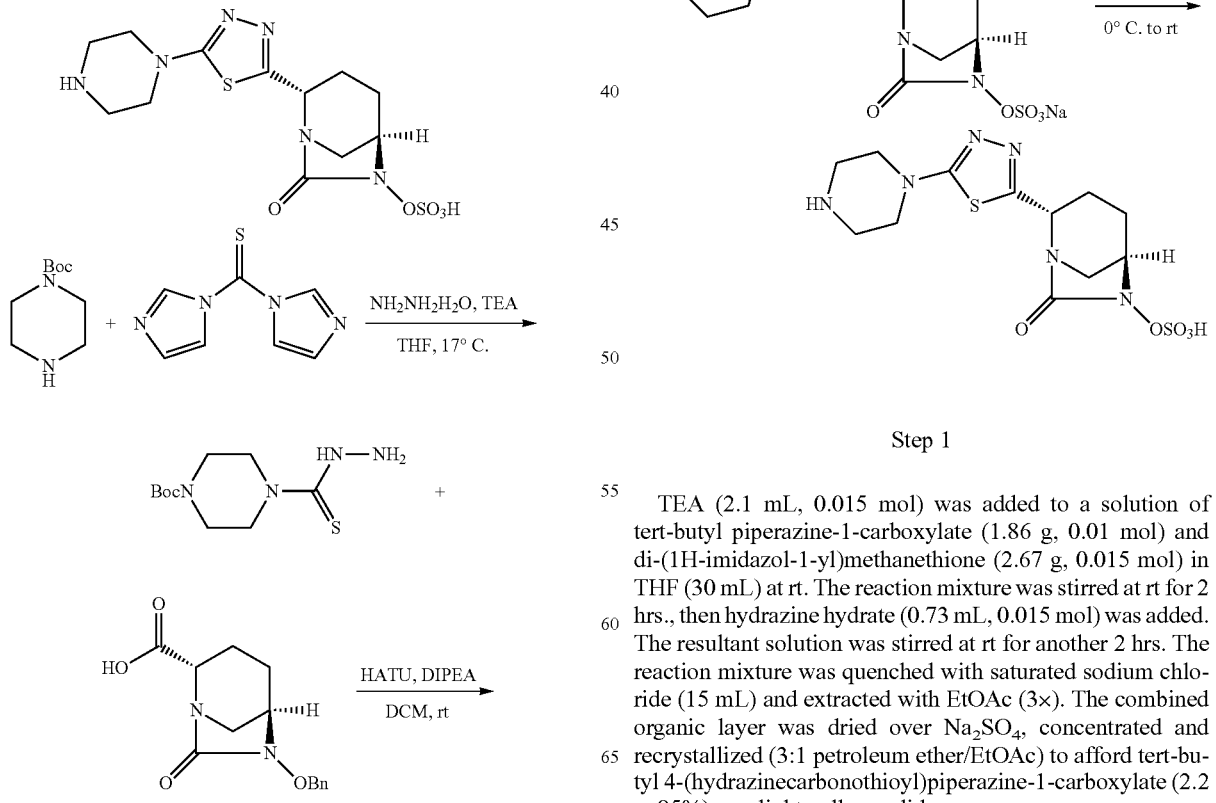

Step 1

TEA (2.1 mL, 0.015 mol) was added to a solution of tert-butyl piperazine-1-carboxylate (1.86 g, 0.01 mol) and di-(1H-imidazol-1-yl)methanethione (2.67 g, 0.015 mol) in THF (30 mL) at rt. The reaction mixture was stirred at rt for 2 hrs., then hydrazine hydrate (0.73 mL, 0.015 mol) was added. The resultant solution was stirred at rt for another 2 hrs. The reaction mixture was quenched with saturated sodium chloride (15 mL) and extracted with EtOAc (3×). The combined organic layer was dried over Na₂SO₄, concentrated and recrystallized (3:1 petroleum ether/EtOAc) to afford tert-butyl 4-(hydrazinecarbonothioyl)piperazine-1-carboxylate (2.2 g, 85%) as a light yellow solid.

Step 2

DIPEA (1.75 mL, 10.8 mmol) was added to a solution of tert-butyl 4-(hydrazinecarbonothioyl)piperazine-1-carboxylate (0.95 g, 3.6 mmol), (2S,5R)-6-(benzyloxy)-7-oxo-1,6-diaza-bicyclo[3.2.1]octane-2-carboxylic acid (1.0 g, 3.6 mmol) and HATU (1.51 g, 3.98 mmol) in dry DMF (15 mL) and the resulting reaction mixture was stirred at rt for 1 h. The reaction mixture was quenched with water (10 mL), and extracted with EtOAc (3×). The combined organic layer was dried over $Na_2SO_4$, then concentrated and purified by silica gel column chromatography (1:50 MeOH/DCM) to afford tert-butyl 4-(2-((2S,5R)-6-(benzyloxy)-7-oxo-1,6-diaza-bicyclo[3.2.1]octane-2-carbonyl)hydrazinecarbonothioyl)piperazine-1-carboxylate (0.92 g, 49%) as a light yellow solid. ESI-MS (EI+, m/z): 519.2 [M+H]+.

Step 3

A solution of tert-butyl 4-(2-((2S,5R)-6-(benzyloxy)-7-oxo-1,6-diaza-bicyclo[3.2.1]octane-2-carbonyl)hydrazinecarbonothioyl)piperazine-1-carboxylate (0.66 g, 1.27 mmol) and Lawesson's reagent (0.36 g, 0.89 mmol) in THF (15 mL) was heated at 66° C. for 1 h, then cooled down to rt Hg(OAc)$_2$ (0.4 g) was added and the mixture was stirred at rt overnight. The solution was then concentrated and the residue was purified by silica gel column chromatography (1:2 EtOAc/petroleum ether) to give tert-butyl 4-(5-((2S,5R)-6-(benzyloxy)-7-oxo-1,6-diaza-bicyclo[3.2.1]octan-2-yl)-1,3,4-thiadiazol-2-yl)piperazine-1-carboxylate (0.15 g, 24%) as a light yellow solid. ESI-MS (EI+, m/z): 501 [M+H]+.

Step 4

A mixture of tert-butyl 4-(5-((2S,5R)-6-(benzyloxy)-7-oxo-1,6-diaza-bicyclo[3.2.1]octan-2-yl)-1,3,4-thiadiazol-2-yl)piperazine-1-carboxylate (180 mg, 0.36 mmol) and 10% Pd(OH)$_2$ (1.8 g) in THF (10 mL) was stirred under $H_2$ at rt for 8.5 hrs. The reaction mixture was then filtered and concentrated to give tert-butyl 4-(5-((2S,5R)-6-hydroxy-7-oxo-1,6-diaza-bicyclo[3.2.1]octan-2-yl)-1,3,4-thiadiazol-2-yl)piperazine-1-carboxylate (133 mg, 90%) as a white solid. ESI-MS (EI+, m/z): 411.17 [M+H]+.

Step 5

A mixture of tert-butyl 4-(5-((2S,5R)-6-hydroxy-7-oxo-1,6-diaza-bicyclo[3.2.1]octan-2-yl)-1,3,4-thiadiazol-2-yl)piperazine-1-carboxylate (133 mg, 0.324 mmol) and SO$_3$.Py (0.258 g, 1.62 mmol) in dry pyridine (1 mL) was stirred at rt for 2 hrs, and then concentrated under vacuum. The residue was redissolved in aqueous NaH$_2$PO$_4$ (1.5 M, 20 mL) and tetrabutylammonium hydrogensulphate (130 mg, 0.38 mmol) was added. The mixture was stirred at rt for 20 min, and extracted with EtOAc (4×). The combined organic layer was dried and concentrated and the residue was purified by silica gel column chromatography (5:1 DCM/acetone) to give tetrabutylammonium (2S,5R)-2-(5-(4-(tert-butoxycarbonyl)piperazin-1-yl)-1,3,4-thiadiazol-2-yl)-7-oxo-1,6-diazabicyclo[3.2.1]octan-6-yl sulfate (100 mg, 42%) as a white solid. ESI-MS (EI−, m/z): 489.0 [M−H]−.

Step 6: Resin Exchange: sodium (2S,5R)-2-(5-(4-(tert-butoxycarbonyl)piperazin-1-yl)-1,3,4-thiadiazol-2-yl)-7-oxo-1,6-diaza-bicyclo[3.2.1]octan-6-yl sulfate Tetrabutylammonium (2S,5R)-2-(5-(4-(tert-butoxycarbonyl)piperazin-1-yl)-1,3,4-thiadiazol-2-yl)-7-oxo-1,6-diazabicyclo[3.2.1]octan-6-yl sulfate (100 mg) was dissolved in a minimum amount of HPLC grade water and acetone (1 mL/1 mL) and passed through a column of 5 g of DOWEX 50WX 8 Na+ resin (the resin was pre-washed with HPLC grade water) and eluted with HPLC grade water to give sodium (2S,5R)-2-(5-(4-(tert-butoxycarbonyl)piperazin-1-yl)-1,3,4-thiadiazol-2-yl)-7-oxo-1,6-diaza-bicyclo[3.2.1]octan-6-yl sulfate (60 mg, 90%) as a white solid after lyophilization. ESI-MS (EI−, m/z): 489.0 [M−H]−. 1H-NMR (500 MHz, D$_2$O): δ 4.24 (s, 1H), 3.62 (m, 4H), 3.56-3.54 (m, 4H), 3.22 (d, J=12.5 Hz, 1H), 3.03 (d, J=12.0 Hz, 1H), 2.46-2.42 (m, 1H), 2.18-2.11 (m, 2H), 1.98-1.93 (m, 1H), 1.47 (s, 9H).

Step 6

TFA (0.20 mL) was added to a mixture of sodium (2S,5R)-2-(5-(4-(tert-butoxycarbonyl)piperazin-1-yl)-1,3,4-thiadiazol-2-yl)-7-oxo-1,6-diaza-bicyclo[3.2.1]octan-6-yl sulfate after lyophilization (33 mg, 0.064 mmol) in dry DCM (0.60 mL) at 0° C. The reaction mixture was stirred at 0° C. for 2-3 hrs and then diluted with ether (~10 mL). The precipitate was collected via centrifugation, washed with ether (3×) and dried under high vacuum to afford (2S,5R)-7-oxo-2-(5-(piperazin-1-yl)-1,3,4-thiadiazol-2-yl)-1,6-diazabicyclo[3.2.1]octan-6-yl hydrogen sulfate (10 mg) as a TFA salt. ESI-MS (EI+, m/z): 391.1.

Example 18

Synthesis of (2S,5R)-2-(3-methyl-1,2,4-oxadiazol-5-yl)-7-oxo-1,6-diazabicyclo[3.2.1]octan-6-yl hydrogen sulfate (Compound 400)

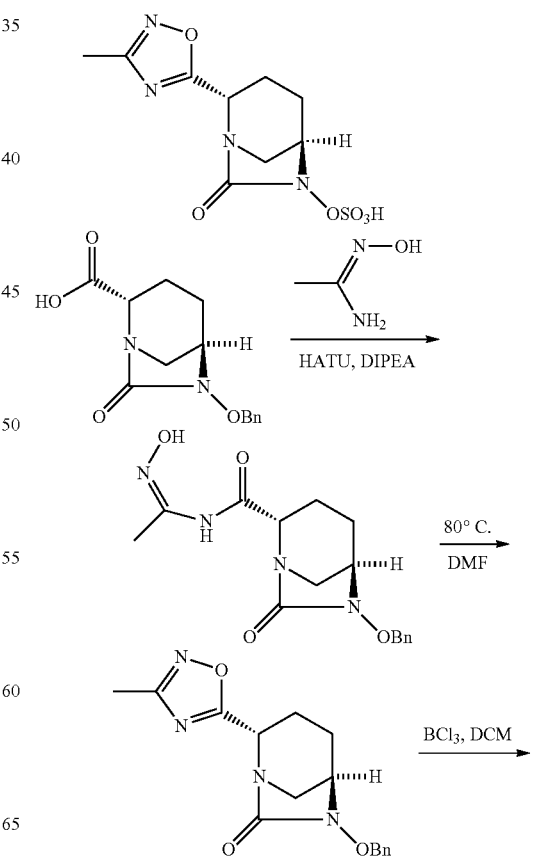

-continued

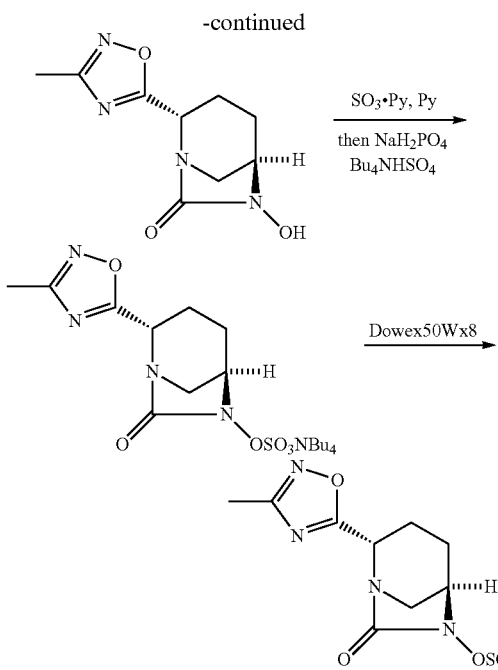

Step 1

DIPEA (0.137 mL, 0.787 mmol) was added to a solution of ethyl 5-((2S,5R)-6-(benzyloxy)-7-oxo-1,6-diazabicyclo[3.2.1]octan-2-yl)-1,2,4-oxadiazole-3-carboxylate (145 mg, 0.525 mmol) and (Z)—N'-hydroxyacetimidamide (38.9 mg, 0.525 mmol) in DCM (2.6 mL), followed by addition of HATU (239 mg, 0.630 mmol). The reaction mixture was stirred at rt for 45 minutes and then concentrated to provide (2S,5R)-6-(benzyloxy)-N—((Z)-1-(hydroxyimino)ethyl)-7-oxo-1,6-diazabicyclo[3.2.1]octane-2-carboxamide (174 mg, 100%), which was used directly in the next step. ESI-MS (EI⁺, m/z): 333.5.

Step 2

A solution of (2S,5R)-6-(benzyloxy)-N—((Z)-1-(hydroxyimino)ethyl)-7-oxo-1,6-diazabicyclo[3.2.1]octane-2-carboxamide (174 mg, 0.524 mmol) in DMF (2 mL) was heated at 80° C. for 2-3 hrs. The solvent was then concentrated in vacuum and the residue was purified by silica gel column chromatography (0 to 5% MeOH/DCM) to provide (2S,5R)-6-(benzyloxy)-2-(3-methyl-1,2,4-oxadiazol-5-yl)-1,6-diazabicyclo[3.2.1]octan-7-one (130 mg, 79%) as a white solid.

Step 3

BCl₃ (1M DCM solution, 2.5 mL, 2.5 mmol) was added dropwise to a solution of (2S,5R)-6-(benzyloxy)-2-(3-methyl-1,2,4-oxadiazol-5-yl)-1,6-diazabicyclo[3.2.1]octan-7-one (130 mg, 0.414 mmol) in dry DCM (12 mL) at −78° C. The mixture was stirred at −78° C. to 0° C. for 4 hrs. The reaction mixture was then quenched with MeOH (2 mL). The solvent was removed and the residue was purified by silica gel column chromatography (0 to 10% MeOH/DCM) to afford (2S,5R)-6-hydroxy-2-(3-methyl-1,2,4-oxadiazol-5-yl)-1,6-diazabicyclo[3.2.1]octan-7-one (30 mg, 32%).

Step 4

To a solution of (2S,5R)-6-hydroxy-2-(3-methyl-1,2,4-oxadiazol-5-yl)-1,6-diazabicyclo[3.2.1]octan-7-one (30 mg, 0.13 mmol) in dry pyridine (3 mL) was added SO₃.Py (85 mg, 0.54 mmol). The mixture was stirred at rt overnight and then concentrated under vacuum. The residue was redissolved in aqueous NaH₂PO₄ (1.5 M, 15 mL) and tetrabutylammonium hydrogensulphate (200 mg, 0.58 mmol) was added. The mixture was stirred at rt for 20 min, and extracted with 10% MeOH/DCM (3×). The combined organic layer was dried and concentrated and the residue was purified by silica gel column chromatography (gradient elution 10:1 to 1:1 DCM/acetone, containing 0.25% of NEt₃) to afford tetrabutylammonium (2S,5R)-2-(3-methyl-1,2,4-oxadiazol-5-yl)-7-oxo-1,6-diazabicyclo[3.2.1]octan-6-yl sulfate (25 mg, 34%).

Step 5

Tetrabutylammonium (2S,5R)-2-(3-methyl-1,2,4-oxadiazol-5-yl)-7-oxo-1,6-diazabicyclo[3.2.1]octan-6-yl sulfate (25 mg) was dissolved in a minimum amount of water and acetone (0.5 mL/0.5 mL) and passed through a column of 20 g of DOWEX 50Wx8 Na⁺ resin (the resin was pre-washed with HPLC grade of water to neutral) and eluted with HPLC grade water to afford sodium (2S,5R)-2-(3-methyl-1,2,4-oxadiazol-5-yl)-7-oxo-1,6-diazabicyclo[3.2.1]octan-6-yl sulfate (14 mg, 93%) after lyophilization as a white solid.

ESI-MS (EI⁺, m/z): 305.1. ¹H NMR (300 MHz, D₂O) δ 4.80 (d, J=6.8 Hz, 1H), 4.18 (br s, 1H), 3.25-3.21 (m, 1H), 2.95-2.89 (m, 1H), 2.36 (s, 3H), 2.32-2.03 (m, 3H), 1.99-1.77 (m, 1H).

Example 19

Synthesis of ethyl 5-((2S,5R)-7-oxo-6-(sulfooxy)-1,6-diazabicyclo[3.2.1]octan-2-yl)-1,2,4-oxadiazole-3-carboxylate (Compound 402)

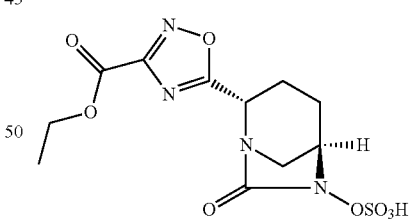

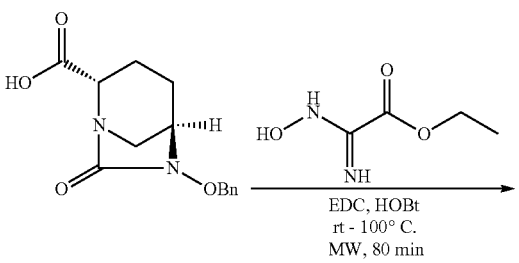

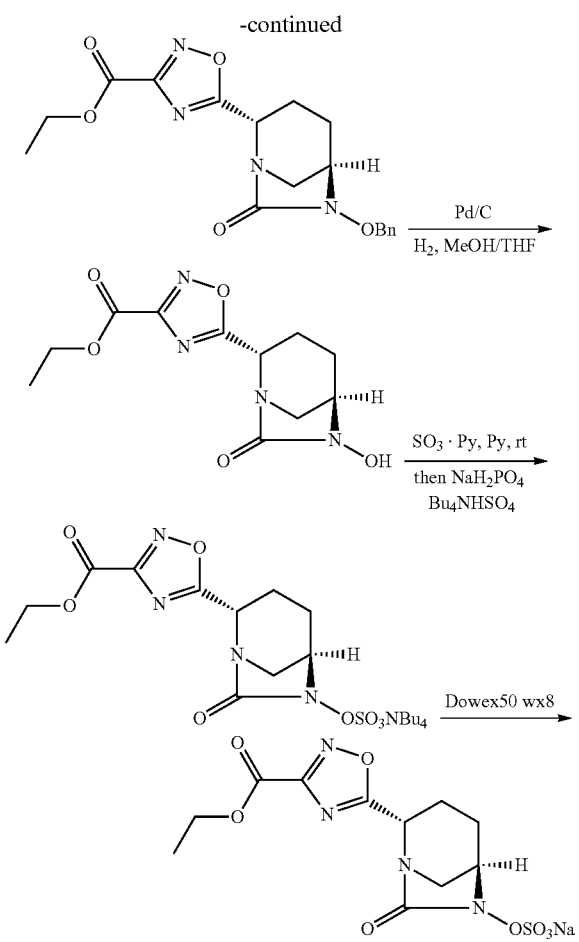

Step 1

EDC (0.916 g, 4.78 mmol) was added to a solution of (2S,5R)-6-(benzyloxy)-7-oxo-1,6-diazabicyclo[3.2.1]octane-2-carboxylic acid (1.2 g, 4.34 mmol) and HOBt (0.732 g, 4.78 mmol) in DMF (12 mL) at rt. The mixture was stirred at rt for 0.5 h, then ethyl 2-(hydroxyamino)-2-iminoacetate (0.689 g, 5.21 mmol) was added and the mixture was stirred for another 0.5 h at rt. The reaction mixture was then heated to 100° C. under microwave for 80 minutes. The solvent was removed under vacuum and the residue was purified by silica gel column chromatography (0 to 5% MeOH/DCM) to afford ethyl 5-((2S,5R)-6-(benzyloxy)-7-oxo-1,6-diazabicyclo[3.2.1]octan-2-yl)-1,2,4-oxadiazole-3-carboxylate (0.85 g, 53%). ESI-MS (EI+, m/z): 373.4.

Step 2

To a solution of ethyl 5-((2S,5R)-6-(benzyloxy)-7-oxo-1,6-diazabicyclo[3.2.1]octan-2-yl)-1,2,4-oxadiazole-3-carboxylate (323 mg, 0.867 mmol) in MeOH (6.0 mL) and THF (3.0 mL) was added 10% Pd/C (18.46 mg, 0.017 mmol). The reaction mixture was stirred under hydrogen balloon at rt for 1 h. The reaction mixture was then filtered and concentrated. The residue was purified by silica gel column chromatography (0 to 5% MeOH/DCM) to afford ethyl 5-((2S,5R)-6-hydroxy-7-oxo-1,6-diazabicyclo[3.2.1]octan-2-yl)-1,2,4-oxadiazole-3-carboxylate (85 mg, 35%).

Step 3

To a solution of ethyl 5-((2S,5R)-6-hydroxy-7-oxo-1,6-diazabicyclo[3.2.1]octan-2-yl)-1,2,4-oxadiazole-3-carboxylate (85 mg, 0.301 mmol) in dry pyridine (5 mL) was added SO$_3$.Py (240 mg, 1.506 mmol). The mixture was stirred at rt overnight and then concentrated under vacuum. The residue was redissolved in aqueous NaH$_2$PO$_4$ (1.5 M, 15 mL). and tetra-butylammonium hydrogensulphate (200 mg, 0.58 mmol) was added. The mixture was stirred at rt for 20 minutes, then was extracted with 10% MeOH/DCM (3×). The combined organic layer was dried and concentrated and the residue was purified by silica gel column chromatography (10:1 to 1:1 DCM/acetone, containing 0.25% of NEt$_3$) to afford tetrabutylammonium (2S,5R)-2-(3-(ethoxycarbonyl)-1,2,4-oxadiazol-5-yl)-7-oxo-1,6-diazabicyclo[3.2.1]octan-6-yl sulfate (94 mg, 51%).

Step 4

Tetrabutylammonium (2S,5R)-2-(3-(ethoxycarbonyl)-1,2,4-oxadiazol-5-yl)-7-oxo-1,6-diazabicyclo[3.2.1]octan-6-yl sulfate (94 mg) was dissolved in a minimum amount of water and acetone (1.0 mL/1.0 mL) and passed through a column of 20 g of DOWEX 50Wx8 Na$^+$ resin (the resin was pre-washed with HPLC grade of water to neutral) and eluted with HPLC grade water to afford sodium (2S,5R)-2-β-(ethoxycarbonyl)-1,2,4-oxadiazol-5-yl)-7-oxo-1,6-diazabicyclo[3.2.1]octan-6-yl sulfate (58 mg, 94%) after lyophilization as a white solid. ESI-MS (EI+, m/z): 363.2. $^1$H NMR (300 MHz, D$_2$O) δ 4.93 (d, J=6.9 Hz, 1H), 4.46 (q, J=7.2 Hz, 2H), 4.21 (br s, 1H), 3.34-3.19 (m, 1H), 3.07-2.97 (m, 1H), 2.45-2.07 (m, 1H), 2.05-1.86 (m, 3H), 1.34 (t, J=7.2 Hz, 3H).

Example 20

Synthesis of (2S,5R)-2-(3-carbamoyl-1,2,4-oxadiazol-5-yl)-7-oxo-1,6-diazabicyclo[3.2.1]octan-6-yl hydrogen sulfate (Compound 401)

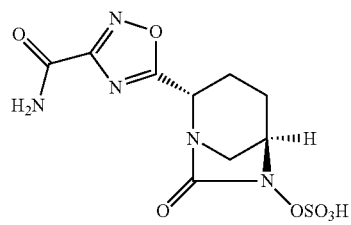

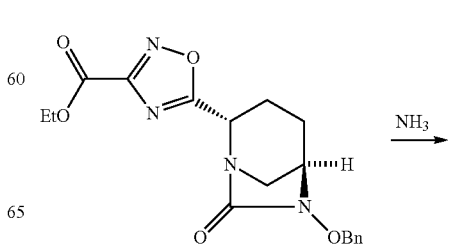

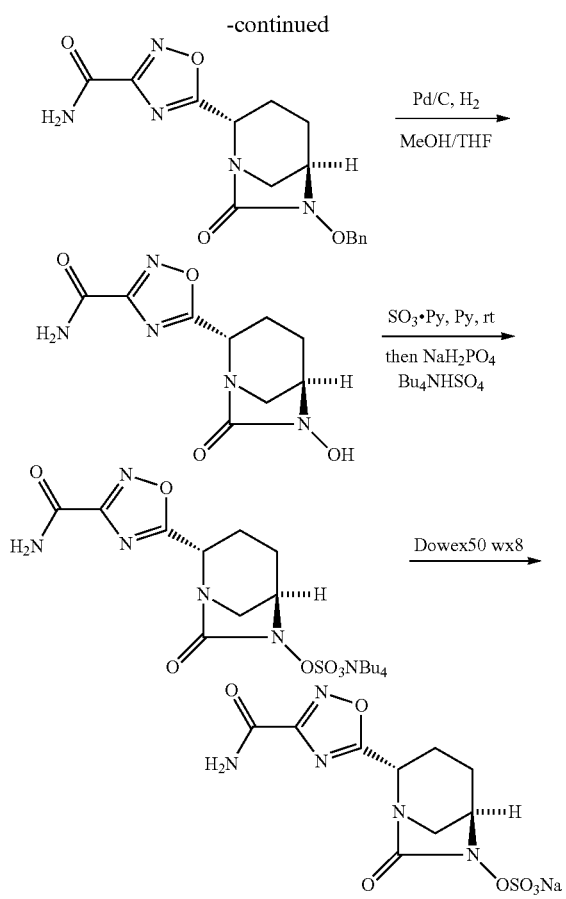

Step 1

Ammonia in MeOH solution (2.3 mL, 16.11 mmol) was added to a solution of ethyl 5-((2S,5R)-6-(benzyloxy)-7-oxo-1,6-diazabicyclo[3.2.1]octan-2-yl)-1,2,4-oxadiazole-3-carboxylate (600 mg, 1.61 mmol) in isopropanol (8 mL) and the reaction mixture was heated at 40° C. for 1 h. The solvent was removed under vacuum and the residue was purified by silica gel column chromatography (0 to 10% MeOH/DCM) to afford 5-((2S,5R)-6-(benzyloxy)-7-oxo-1,6-diazabicyclo[3.2.1]octan-2-yl)-1,2,4-oxadiazole-3-carboxamide (220 mg, 40%). ESI-MS (EI+, m/z): 344.3.

Step 2

To a solution of 5-((2S,5R)-6-(benzyloxy)-7-oxo-1,6-diazabicyclo[3.2.1]octan-2-yl)-1,2,4-oxadiazole-3-carboxamide (220 mg, 0.641 mmol) in MeOH (4.0 mL) and THF (12.0 mL) was added 10% Pd/C (13.6 mg, 0.013 mmol). The reaction mixture was stirred under hydrogen balloon for 1 h at rt, then filtered and concentrated to afford 5-((2S,5R)-6-hydroxy-7-oxo-1,6-diazabicyclo[3.2.1]octan-2-yl)-1,2,4-oxadiazole-3-carboxamide (~150 mg, 93%), which was used directly in the next step.

Step 3

To a solution of 5-((2S,5R)-6-hydroxy-7-oxo-1,6-diazabicyclo[3.2.1]octan-2-yl)-1,2,4-oxadiazole-3-carboxamide (~150 mg, 0.5 mmol) in dry pyridine (5 mL) was added SO$_3$.Py (510 mg, 3.20 mmol). The mixture was stirred at rt overnight and then concentrated under vacuum. The residue was redissolved in aqueous NaH$_2$PO$_4$ (1.5 M, 15 mL) and tetrabutylammonium hydrogensulphate (400 mg, 2.38 mmol) was added. The mixture was stirred at rt for 20 min, and extracted with 10% MeOH/DCM (3×). The combined organic layer was dried and concentrated and the residue was purified by silica gel column chromatography (10:1 to 1:1 DCM/acetone, containing 0.25% of NEt$_3$) to afford tetrabutylammonium (2S,5R)-2-(3-carbamoyl-1,2,4-oxadiazol-5-yl)-7-oxo-1,6-diazabicyclo[3.2.1]octan-6-yl sulfate (22 mg, 8%).

Step 4

Tetrabutylammonium (2S,5R)-2-(3-carbamoyl-1,2,4-oxadiazol-5-yl)-7-oxo-1,6-diazabicyclo[3.2.1]octan-6-yl sulfate (22 mg, 0.038 mmol) was dissolved in a minimum amount of water and acetone (0.5 mL/0.5 mL) and passed through a column of 20 g of DOWEX 50Wx8 Na+ resin (the resin was pre-washed with HPLC grade of water to neutral) and eluted with HPLC grade water to afford sodium (2S,5R)-2-β-carbamoyl-1,2,4-oxadiazol-5-yl)-7-oxo-1,6-diazabicyclo[3.2.1]octan-6-yl sulfate (12 mg, 89%) after lyophilization as a white solid. ESI-MS (EI+, m/z): 334.1. $^1$H NMR (300 MHz, D$_2$O) δ 4.90 (d, J=7.0 Hz, 1H), 4.20 (br s, 1H), 3.-3.23 (m, 1H), 3.00-2.93 (m, 1H), 2.45-2.07 (m, 3H), 2.03-1.95 (m, 1H).

Example 21

Synthesis of (2S,5R)-7-oxo-2-(1,2,4-thiadiazol-5-yl)-1,6-diazabicyclo[3.2.1]octan-6-yl hydrogen sulfate (Compound 500)

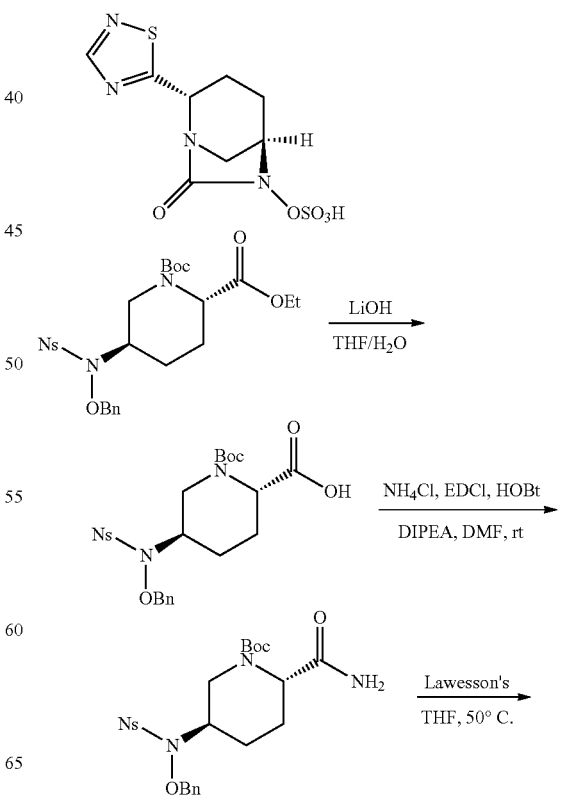

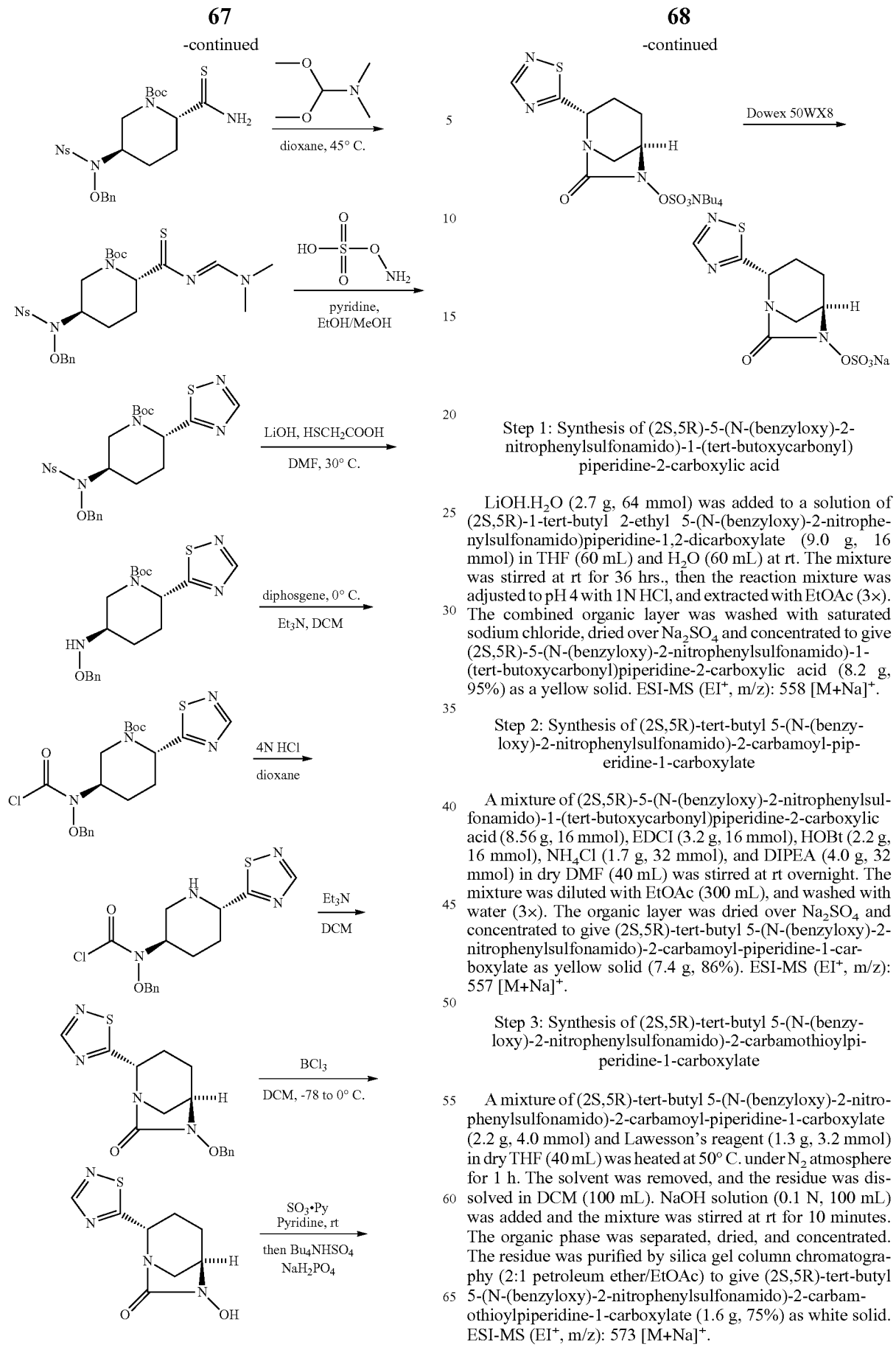

Step 1: Synthesis of (2S,5R)-5-(N-(benzyloxy)-2-nitrophenylsulfonamido)-1-(tert-butoxycarbonyl)piperidine-2-carboxylic acid LiOH.H$_2$O (2.7 g, 64 mmol) was added to a solution of (2S,5R)-1-tert-butyl 2-ethyl 5-(N-(benzyloxy)-2-nitrophenylsulfonamido)piperidine-1,2-dicarboxylate (9.0 g, 16 mmol) in THF (60 mL) and H$_2$O (60 mL) at rt. The mixture was stirred at rt for 36 hrs., then the reaction mixture was adjusted to pH 4 with 1N HCl, and extracted with EtOAc (3×). The combined organic layer was washed with saturated sodium chloride, dried over Na$_2$SO$_4$ and concentrated to give (2S,5R)-5-(N-(benzyloxy)-2-nitrophenylsulfonamido)-1-(tert-butoxycarbonyl)piperidine-2-carboxylic acid (8.2 g, 95%) as a yellow solid. ESI-MS (EI$^+$, m/z): 558 [M+Na]$^+$.

Step 2: Synthesis of (2S,5R)-tert-butyl 5-(N-(benzyloxy)-2-nitrophenylsulfonamido)-2-carbamoyl-piperidine-1-carboxylate A mixture of (2S,5R)-5-(N-(benzyloxy)-2-nitrophenylsulfonamido)-1-(tert-butoxycarbonyl)piperidine-2-carboxylic acid (8.56 g, 16 mmol), EDCI (3.2 g, 16 mmol), HOBt (2.2 g, 16 mmol), NH$_4$Cl (1.7 g, 32 mmol), and DIPEA (4.0 g, 32 mmol) in dry DMF (40 mL) was stirred at rt overnight. The mixture was diluted with EtOAc (300 mL), and washed with water (3×). The organic layer was dried over Na$_2$SO$_4$ and concentrated to give (2S,5R)-tert-butyl 5-(N-(benzyloxy)-2-nitrophenylsulfonamido)-2-carbamoyl-piperidine-1-carboxylate as yellow solid (7.4 g, 86%). ESI-MS (EI$^+$, m/z): 557 [M+Na]$^+$.

Step 3: Synthesis of (2S,5R)-tert-butyl 5-(N-(benzyloxy)-2-nitrophenylsulfonamido)-2-carbamothioylpiperidine-1-carboxylate A mixture of (2S,5R)-tert-butyl 5-(N-(benzyloxy)-2-nitrophenylsulfonamido)-2-carbamoyl-piperidine-1-carboxylate (2.2 g, 4.0 mmol) and Lawesson's reagent (1.3 g, 3.2 mmol) in dry THF (40 mL) was heated at 50° C. under N$_2$ atmosphere for 1 h. The solvent was removed, and the residue was dissolved in DCM (100 mL). NaOH solution (0.1 N, 100 mL) was added and the mixture was stirred at rt for 10 minutes. The organic phase was separated, dried, and concentrated. The residue was purified by silica gel column chromatography (2:1 petroleum ether/EtOAc) to give (2S,5R)-tert-butyl 5-(N-(benzyloxy)-2-nitrophenylsulfonamido)-2-carbamothioylpiperidine-1-carboxylate (1.6 g, 75%) as white solid. ESI-MS (EI$^+$, m/z): 573 [M+Na]$^+$.

Step 4: Synthesis of (2S,5R)-tert-butyl 5-(N-(benzyloxy)-2-nitrophenylsulfonamido)-2-((E)-(dimethylamino)methylenecarbamothioyl)piperidine-1-carboxylate A mixture of (2S,5R)-tert-butyl 5-(N-(benzyloxy)-2-nitrophenylsulfonamido)-2-carbamothioylpiperidine-1-carboxylate (1.65 g, 3 mmol) and 1,1-dimethoxy-N,N-dimethylmethanamine (1.08 g, 9.0 mmol) in dry dioxane (20 mL) was stirred at 45° C. overnight. The reaction mixture was concentrated under vacuum and the residue was purified by silica gel column chromatography (1:1 petroleum ether/EtOAc) to give (2S,5R)-tert-butyl 5-(N-(benzyloxy)-2-nitrophenylsulfonamido)-2-((E)-(dimethylamino)methylenecarbamothioyl)piperidine-1-carboxylate (1.3 g, 72%) as a yellow solid. ESI-MS (EI$^+$, m/z): 606 [M+H]$^+$.

Step 5: Synthesis of (2S,5R)-tert-butyl 5-(N-(benzyloxy)-2-nitrophenylsulfonamido)-2-(1,2,4-thiadiazol-5-yl)piperidine-1-carboxylate A solution of pyridine (320 mg, 4.0 mmol) in CH$_3$OH (10 mL) was added to a mixture of (2S,5R)-tert-butyl 5-(N-(benzyloxy)-2-nitrophenylsulfonamido)-2-((E)-(dimethylamino)methylenecarbamothioyl)piperidine-1-carboxylate (1.2 g, 2.0 mmol) in EtOH (20 mL), followed by addition of (aminooxy)sulfonic acid (270 mg, 2.4 mmol). The mixture was stirred at rt for 2 hrs. The solvent was removed, and the residue was purified by silica gel column chromatography (3:1 petroleum ether/EtOAc) to (2S,5R)-tert-butyl 5-(N-(benzyloxy)-2-nitrophenylsulfonamido)-2-(1,2,4-thiadiazol-5-yl)piperidine-1-carboxylate (520 mg, 48%) as a yellow solid. ESI-MS (EI$^+$, m/z): 598 [M+Na]$^+$.

Step 6: Synthesis of (2S,5R)-tert-butyl 5-(benzyloxyamino)-2-(1,2,4-thiadiazol-5-yl)piperidine-1-carboxylate To a mixture of (2S,5R)-tert-butyl 5-(N-(benzyloxy)-2-nitrophenylsulfonamido)-2-(1,2,4-thiadiazol-5-yl)piperidine-1-carboxylate (1.17 g, 2.0 mmol) in dry DMF (30 mL) at rt was added LiOH.H$_2$O (640 mg, 16.0 mmol), followed by addition of 2-mercaptoacetic acid (920 mg, 10.0 mmol). The mixture was stirred at 30° C. for 24 hrs., then the mixture was diluted with EtOAc (200 mL), washed with water (4×), dried over Na$_2$SO$_4$ and concentrated. The residue was purified by silica gel column chromatography (3:1 petroleum ether/EtOAc) to give (2S,5R)-tert-butyl 5-(benzyloxyamino)-2-(1,2,4-thiadiazol-5-yl)piperidine-1-carboxylate (560 mg, 75%) as an oil. ESI-MS (EI$^+$, m/z): 413 [M+Na]$^+$.

Step 7: Synthesis of (2S,5R)-tert-butyl 5-(benzyloxy(chlorocarbonyl)amino)-2-(1,2,4-thiadiazol-5-yl)piperidine-1-carboxylate Diphosgene (360 mg, 1.8 mmol) was added to a solution of (2S,5R)-tert-butyl 5-(benzyloxyamino)-2-(1,2,4-thiadiazol-5-yl)piperidine-1-carboxylate (468 mg, 1.2 mmol) in dry DCM (20 mL) at 0° C. followed by addition of TEA (360 mg, 3.6 mmol). The mixture was stirred at 0° C. for 2 hrs and then quenched with saturated NaHCO$_3$ (20 mL). The reaction mixture was then extracted with DCM (3×) and the combined organic layer was dried over Na$_2$SO$_4$ and concentrated to afford (2S,5R)-tert-butyl 5-(benzyloxy(chlorocarbonyl)amino)-2-(1,2,4-thiadiazol-5-yl)piperidine-1-carboxylate, which was directly used in the next step. ESI-MS (EI$^+$, m/z): 445 [M+H]$^+$.

Step 8: Synthesis of (3R,6S)-6-(1,2,4-thiadiazol-5-yl)piperidin-3-yl(benzyloxy)carbamic chloride (2S,5R)-tert-butyl 5-(benzyloxy(chlorocarbonyl)amino)-2-(1,2,4-thiadiazol-5-yl)piperidine-1-carboxylate was dissolved in 4 N HCl in dioxane (10 mL). The mixture was stirred at rt for 0.5 h and then concentrated to provide the crude ((3R,6S)-6-(1,2,4-thiadiazol-5-yl)piperidin-3-yl)(benzyloxy)carbamic chloride HCl salt, which was directly used in the next step. ESI-MS (EI$^+$, m/z): 445 [M+H]$^+$.

Step 9: (2S,5R)-6-(benzyloxy)-2-(1,2,4-thiadiazol-5-yl)-1,6-diazabicyclo[3.2.1]octan-7-one To a mixture of ((3R,6S)-6-(1,2,4-thiadiazol-5-yl)piperidin-3-yl)(benzyloxy)carbamic chloride HCl salt in dry DCM (15 mL) at 0° C. was added TEA (606 mg, 6.0 mmol). The mixture was stirred at rt for 2 hrs and then concentrated. The residue was purified by silica gel column chromatography (3:1 petroleum ether/EtOAc) to give (2S,5R)-6-(benzyloxy)-2-(1,2,4-thiadiazol-5-yl)-1,6-diazabicyclo[3.2.1]octan-7-one (190 mg, 51%) as a yellow solid. ESI-MS (EI$^+$, m/z): 317 [M+H]$^+$, $^1$HNMR (500 M, CDCl$_3$): δ 8.62 (s, 1H), 7.46-7.37 (m, 5H), 5.09 (d, J=11.2 Hz, 1H), 4.92 (d, J=11.2 Hz, 1H), 4.90 (br d, J=5.5 Hz, 1H), 3.35 (m, 1H), 2.88 (br d, J=6.0 Hz, 1H), 2.79 (d, J=12.0 Hz, 1H), 2.31-2.28 (m, 2H), 2.21-2.11 (m, 1H), 1.98-1.90 (m, 1H).

Step 10: Synthesis of (2S,5R)-6-hydroxy-2-(1,2,4-thiadiazol-5-yl)-1,6-diaza-bicyclo[3.2.1]octan-7-one BCl$_3$ (1 M in DCM, 3.0 mL, 3.0 mmol) was added dropwise to a solution of (2S,5R)-6-(benzyloxy)-2-(1,2,4-thiadiazol-5-yl)-1,6-diazabicyclo[3.2.1]octan-7-one (190 mg, 0.60 mmol) in dry DCM (20 mL) at −78° C. The mixture was stirred at 0° C. for 6 hrs., then, MeOH (3 mL) was added slowly at −78° C. The solvents were evaporated under vacuum to give (2S,5R)-6-hydroxy-2-(1,2,4-thiadiazol-5-yl)-1,6-diaza-bicyclo[3.2.1]octan-7-one (110 mg, 80%) as a yellow solid, which was directly used in the next step. ESI-MS (EI$^-$, m/z): 227.1 [M−H]$^-$.

Step 11: Synthesis of tetrabutylammonium (2S,5R)-7-oxo-2-(1,2,4-thiadiazol-5-yl)-1,6-diaza-bicyclo[3.2.1]octan-6-yl sulfate To a solution of crude (2S,5R)-6-hydroxy-2-(1,2,4-thiadiazol-5-yl)-1,6-diazabicyclo[3.2.1]octan-7-one (110 mg) in dry pyridine (5 mL) was added SO$_3$.Py (0.40 g, 2.3 mmol). The mixture was stirred at rt for 6 hrs and then concentrated under vacuum.

The residue was redissolved in aqueous NaH$_2$PO$_4$ (1.5 M, 10 mL).

Tetrabutylammonium hydrogensulphate (203 mg, 0.6 mmol) was added. The mixture was stirred at rt for 20 min, and extracted with EtOAc (4×). The combined organic layer was dried and concentrated and the residue was purified by silica gel column chromatography (gradient elution 10:1 to 2:1 DCM/acetone) to give tetrabutylammonium (2S,5R)-7-oxo-2-(1,2,4-thiadiazol-5-yl)-1,6-diaza-bicyclo[3.2.1]octan-6-yl sulfate as a yellow solid (104 mg, 40% for two steps). ESI-MS (EI$^-$, m/z): 305.0 [M−H]$^-$.

Step 13: Resin Exchange, synthesis of sodium (2S, 5R)-7-oxo-2-(1,2,4-thiadiazol-5-yl)-1,6-diaza-bicyclo[3.2.1]octan-6-yl sulfate Tetrabutylammonium (2S,5R)-7-oxo-2-(1,2,4-thiadiazol-5-yl)-1,6-diaza-bicyclo[3.2.1]octan-6-yl sulfate (104 mg) was dissolved in a minimum amount of HPLC grade water (~5 mL) and passed through a column of 10 g of DOWEX 50WX 8 Na+ resin (the resin was pre-washed with >0.5 L of HPLC grade water) and eluted with HPLC grade water to provide sodium (2S,5R)-7-oxo-2-(1,2,4-thiadiazol-5-yl)-1, 6-diaza-bicyclo[3.2.1]octan-6-yl sulfate (56 mg, 90%) was obtained after lyophilization as a white solid. ESI-MS (EI−, m/z): 305.0 [M−H]−. $^1$H-NMR (500 MHz, CDCl$_3$): δ 8.68 (s, 1H), 4.96 (d, J=6.0 Hz, 1H), 4.16 (s, 1H), 3.23 (br d, J=12.0 Hz, 1H), 3.02 (d, J=12.0 Hz, 1H), 2.39-2.35 (m, 1H), 1.30-2.22 (m, 1H), 2.15-2.09 (m, 1H), 1.88-1.81 (m, 1H).

Example 22

Construction of Isogenic β-Lactamase Strains

A set of β-lactamase expressing isogenic *E. coli* strains was constructed by cloning a β-lactamase gene into a customized derivative of pBR322 (GenBank Accession Number J01749) and transforming the engineered plasmids into *E. coli*. The NdeI restriction site within the plasmid backbone of pBR322 was removed to generate pBR322 ΔNdeI. The pBR322 ΔNdeI vector itself, minus the blaTEM-1 gene, was amplified using two primers: (1) pBR-Pbla 5'-cg catatgactettectttttcaatattattg-3, SEQ ID 1, a primer with an engineered NdeI restriction site at the 3' end of the blaTEM-1 promoter and (2) pBR-vec-1 5'-gc ggatccctgtcagaccaagtttactc-3', SEQ ID 2, a primer with an engineered BamHI restriction site at the 3' end of the blaTEM-1 open reading frame. The chloramphenicol resistance gene, cat, was generated by PCR amplification from pKD3 (GenBank Accession Number AY048742) using primers with an engineered NdeI restriction site at the 5' end (Pbla-cat 5'-gccatatgatggagaaaaaaatcactgg-3', SEQ ID 3) and an engineered BamHI restriction site at the 3' end (Vec-1-cat 5'-cgggatcctagagaataggaacttcgg-3', SEQ ID 4) of the resistance gene. The two PCR products, pBR322 ΔNdeI and cat were ligated together generating pBR-CBST (pBR322 ΔNdeI ΔTEM-1::cat Seq. ID 5) which retains both the pBR322 tetracycline resistance cassette, tetA, and the plasmid origin of replication but the blaTEM-1 gene was replaced by the cat gene.

Using this engineering strategy a number of plasmids producing β-lactamase genes from different classes (see below) were generated using synthetic genes with an engineered NdeI restriction site at the 5' end and BamHI restriction site at the 3' end of each gene (GenScript). Both the synthetic β-lactamase genes and cat gene were ligated into the NdeI/BamHI sites of the pBR322 ΔNdeI PCR product and transformed into electrocompetent *E. coli* ElectroMax DH10B (Invitrogen/Life Technologies). *E. coli* DH10B harboring the recombinant plasmids were selected on LB agar (supplemented with 25 μg/mL tetracycline) and single isolated colonies were then inoculated into 5 mL LB media (supplemented with 25 μg/mL tetracycline), and incubated at 37° C. with aeration (250 rpm) for 18 hrs. The cultures were frozen back at −80° C. in 20% glycerol. The DNA sequence of the cloned β-lactamase genes was confirmed. The β-lactamase gene expression in the recombinant *E. coli* strains was driven by the blaTEM-1 promoter in the pBR-CBST plasmid and was characterized by MIC profiling of the *E. coli* recombinant strains against comparator β-lactam/BLI combinations in broth microdilution assay.

TABLE X

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQ ID 6 | A | *K. pneumoniae* | EU784136 |
| CTX-M-15 | pBR-CBST-CTX-M-15 SEQ ID 7 | A | *K. pneumoniae* | JF775516 |
| SHV-12 | pBR-CBST-SHV-12 SEQ ID 8 | A | *K. pneumoniae* | AY008838 |
| P99 AmpC | pBR-CBST-P99 AMPC SEQ ID 9 | C | *E. cloacea* | XO7274 |
| OXA-15 | pBR-CBST-OXA-15 SEQ ID 10 | D | *P. aeruginosa* | PAU63835 |

Nucleotide Sequences of pBR-CBST Plasmids (Containing β-Lactamase or cat Genes) Used in the *E. coli* Isogenic Strains (relevant restriction sites are underlined; β-lactamase sequences in all caps, tetA sequence is in italics)

```
pBR-CBST-cat
                                         SEQ ID 5
ttcttgaagacgaaagggcctcgtgatacgcctattttatataggttaa tgtcatgataataatggtttacttagacgtcaggtggcacttttcgggga aatgtgcgcggaacccctatttgtttattttctaaatacattcaaatat gtatccgctcatgagacaataaccctgataaatgcttcaataatattgaa aaaggaagagtcatATGGAGAAAAAAATCACTGGATATACCACCGTTGAT

ATATCCCAATGGCATCGTAAAGAACATTTTGAGGCATTTCAGTCAGTTGC

TCAATGTACCTATAACCAGACCGTTCAGCTGGATATTACGGCCTTTTTAA

AGACCGTAAAGAAAAATAAGCACAAGTTTTATCCGGCCTTTATTCACATT

CTTGCCCGCCTGATGAATGCTCATACGGAATTTCGTATGGCAATGAAAGA

CGGTGAGCTGGTGATATGGGATAGTGTTCACCCTTGTTACACCGTTTTCC

ATGAGCAAACTGAAACGTTTTCATCGCTCTGGAGTGAATACCACGACGAT
```

-continued

```
TTCCGGCAGTTTCTACACATATATTCGCAAGATGTGGCGTGTTACGGTGA
AAACCTGGCCTATTTCCCTAAAGGGTTTATTGAGAATATGTTTTTCGTCT
CAGCCAATCCCTGGGTGAGTTTCACCAGTTTTGATTTAAACGTGGCCAAT
ATGGACAACTTCTTCGCCCCCGTTTTCACTATGGGCAAATATTATACGCA
AGGCGACAAGGTGCTGATGCCGCTGGCGATTCAGGTTCATCATGCCGTCT
GTGATGGCTTCCATGTCGGCAGAATGCTTAATGAATTACAACAGTACTGC
GATGAGTGGCAGGGCGGGGCGTAAGTGGCAGGGCGGGGCGTAAGGCGCGC
CATTTAAATGAAGTTCCTATTCCGAAGTTCCTATTCTCTAGggatccctg
tcagaccaagtttactcatatatactttagattgatttaaaacttcattt
ttaatttaaaaggatctaggtgaagatcctttttgataatctcatgacca
aaatcccttaacgtgagttttcgttccactgagcgtcagaccccgtagaa
aagatcaaaggatcttcttgagatccttttttctgcgcgtaatctgctg
cttgcaaacaaaaaaaccaccgctaccagcggtggtttgtttgccggatc
aagagctaccaactctttttccgaaggtaactggcttcagcagagcgcag
ataccaaatactgtccttctagtgtagccgtagttaggccaccacttcaa
gaactctgtagcaccgcctacatacctcgctctgctaatcctgttaccag
tggctgctgccagtggcgataagtcgtgtcttaccgggttggactcaaga
cgatagttaccggataaggcgcagcggtcgggctgaacggggggttcgtg
cacacagcccagcttggagcgaacgacctacaccgaactgagatacctac
agcgtgagctatgagaaagcgccacgcttcccgaagggagaaaggcggac
aggtatccggtaagcggcagggtcggaacaggagagcgcacgagggagct
tccaggggaaacgcctggtatctttatagtcctgtcgggtttcgccacc
tctgacttgagcgtcgatttttgtgatgctcgtcaggggggcggagccta
tggaaaaacgccagcaacgcggcctttttacggttcctggccttttgctg
gccttttgctcacatgttctttcctgcgttatcccctgattctgtggata
accgtattaccgcctttgagtgagctgataccgctcgccgcagccgaacg
accgagcgcagcgagtcagtgagcgaggaagcggaagagcgcctgatgcg
gtattttctccttacgcatctgtgcggtatttcacaccgcatttggtgca
ctctcagtacaatctgctctgatgccgcatagttaagccagtatacactc
cgctatcgctacgtgactgggtcatggctgcgccccgacacccgccaaca
cccgctgacgcgccctgacgggcttgtctgctcccggcatccgcttacag
acaagctgtgaccgtctccgggagctgcatgtgtcagaggttttcaccgt
catcaccgaaacgcgcgaggcagctgcggtaaagctcatcagcgtggtcg
tgaagcgattcacagatgtctgcctgttcatccgcgtccagctcgttgag
tttctccagaagcgttaatgtctggcttctgataaagcgggccatgttaa
gggcggttttttcctgtttggtcactgatgcctccgtgtaaggggggattt
ctgttcatgggggtaatgataccgatgaaacgagagaggatgctcacgat
acgggttactgatgatgaacatgcccggttactgaacgttgtgagggta
aacaactggcggtatggatgcggcgggaccagagaaaaatcactcagggt
caatgccagcgcttcgttaatacagatgtaggtgttccacagggtagcca
gcagcatcctgcgatgcagatccggaacataatggtgcagggcgctgact
``` tccgcgtttccagactttacgaaacacggaaaccgaagaccattcatgtt
gttgctcaggtcgcagacgttttgcagcagcagtcgcttcacgttcgctc
gcgtatcggtgattcattctgctaaccagtaaggcaaccccgccagccta
gccgggtcctcaacgacaggagcacgatcatgcgcaccgtggccaggac
ccaacgctgcccgagatgcgccgcgtgcggctgctggagatggcggacgc
gatggatatgttctgccaagggttggtttgcgcattcacagttctccgca
agaattgattggctccaattcttggagtggtgaatccgttagcgaggtgc
cgccggcttccatt*caggtcgaggtggcccggctccatgcaccgcgacgc*
*aacgcggggaggcagacaaggtatagggcggcgcctacaatccatgccaa*
*cccgttccatgtgctcgccgaggcggcataaatcgccgtgacgatcagcg*
*gtccagtgatcgaagttaggctggtaagagccgcgagcgatccttgaagc*
*tgtccctgatggtcgtcatctacctgcctggacagcatggcctgcaacgc*
*gggcatcccgatgccgccgaagcgagaagaatcataatggggaaggcca*
*tccagcctcgcgtcgcgaacgccagcaagacgtagcccagcgcgtcggcc*
gccatgccggcgataatggcctgcttctcgccgaaacgtttggtggcggg
accagtgacgaaggcttgagcgagggcgtgcaagattccgaataccgcaa
gcgacaggccgatcatcgtcgcgctccagcgaaagcggtcctcgccgaaa
atgaccagagcgctgccggcacctgtcctacgagttgcatgataaagaa
gacagtcataagtgcggcgacgatagtcatgccccgcgcccaccggaagg
agctgactgggttgaaggctctcaagggcatcggtcgacgctctccctta
*tgcgactcctgcattaggaagcagccagtagtaggttgaggccgttgag*
*caccgccgccgcaaggaatggtgcatgcaaggagatggcgcccaacagtc*
*ccccggccacggggcctgccaccatacccacgccgaaacaagcgctcatg*
*agcccgaagtggcgagcccgatcttccccatcggtgatgtcggcgatata*
*ggcgccagcaaccgcacctgtggcgccggtgatgccggccacgatgcgtc*
*cggcgtagaggattcacaggacgggtgtggtcgccatgatcgcgtagtcg*
*atagtggctccaagtagcgaagcgagcaggactgggcggcggccaaagcg*
*gtcggacagtgctccgagaacgggtgcgcatagaaattgcatcaacgcat*
*atagcgctagcagcacgccatagtgactggcgatgctgtcggaatggacg*
*atatcccgcaagaggcccggcagtaccggcataaccaagcctatgcctac*
*agcatccagggtgacggtgccgaggatgacgatgagcgcattgttagatt*
*tcat*acacggtgcctgactgcgttagcaatttaactgtgataaactaccg
cattaaagcttatcgatgataagctgtcaaacatgagaa
pBR-CBST-KPC-2
                              SEQ ID 6
ttcttgaagacgaaagggcctcgtgatacgcctatttttataggttaatg
tcatgataataatggtttcttagacgtcaggtggcacttttcggggaaat
gtgcgcggaacccctatttgtttatttttctaaatacattcaaatatgta
tccgctcatgagacaataaccctgataaatgcttcaataatattgaaaaa
ggaagagt<u>catATGTCACTGTATCGCCGTCTAGTTCTGCTGTCTTGTCTC</u>
TCATGGCCGCTGGCTGGCTTTTCTGCCACCGCGCTGACCAACCTCGTCGC -continued GGAACCATTCGCTAAACTCGAACAGGACTTTGGCGGCTCCATCGGTGTGT
ACGCGATGGATACCGGCTCAGGCGCAACTGTAAGTTACCGCGCTGAGGAG
CGCTTCCCACTGTGCAGCTCATTCAAGGGCTTTCTTGCTGCCGCTGTGCT
GGCTCGCAGCCAGCAGCAGGCCGGCTTGCTGGACACACCCATCCGTTACG
GCAAAAATGCGCTGGTTCCGTGGTCACCCATCTCGGAAAAATATCTGACA
ACAGGCATGACGGTGGCGGAGCTGTCCGCGGCCGCCGTGCAATACAGTGA
TAACGCCGCCGCCAATTTGTTGCTGAAGGAGTTGGGCGGCCCGGCCGGGC
TGACGGCCTTCATGCGCTCTATCGGCGATACCACGTTCCGTCTGGACCGC
TGGGAGCTGGAGCTGAACTCCGCCATCCCAGGCGATGCGCGCGATACCTC
ATCGCCGCGCGCCGTGACGGAAAAGCTTACAAAAACTGACACTGGGCTCTG
CACTGGCTGCGCCGCAGCGGCAGCAGTTTGTTGATTGGCTAAAGGGAAAC
ACGACCGGCAACCACCGCATCCGCGCGGCGGTGCCGGCAGACTGGGCAGT
CGGAGACAAAACCGGAACCTGCGGAGTGTATGGCACGGCAAATGACTATG
CCGTCGTCTGGCCCACTGGGCGCGCACCTATTGTGTTGGCCGTCTACACC
CGGGCGCCTAACAAGGATGACAAGCACAGCGAGGCCGTCATCGCCGCTGC
GGCTAGACTCGCGCTCGAGGGATTGGGCGTCAACGGGCAGTAAggatccc
tgtcagaccaagtttactcatatatactttagattgatttaaaacttcat
ttttaatttaaaaggatctaggtgaagatcctttttgataatctcatgac
caaaatcccttaacgtgagttttcgttccactgagcgtcagaccccgtag
aaagatcaaaggatcttcttgagatcctttttttctgcgcgtaatctgc
tgcttgcaaacaaaaaaaccaccgctaccagcggtggtttgtttgccgga
tcaagagctaccaactctttttccgaaggtaactggcttcagcagagcgc
agataccaaatactgtccttctagtgtagccgtagttaggccaccacttc
aagaactctgtagcaccgcctacatacctcgctctgctaatcctgttacc
agtggctgctgccagtggcgataagtcgtgtcttaccgggttggactcaa
gacgatagttaccggataaggcgcagcggtcgggctgaacggggggttcg
tgcacacagcccagcttggagcgaacgacctacaccgaactgagatacct
acagcgtgagctatgagaaagcgccacgcttcccgaagggagaaaggcgg
acaggtatccggtaagcggcagggtcggaacaggagagcgcacgagggag
cttccaggggaaacgcctggtatctttatagtcctgtcgggtttcgcca
cctctgacttgagcgtcgatttttgtgatgctcgtcaggggggcggagcc
tatggaaaaacgccagcaacgcggcctttttacggttcctggccttttgc
tggccttttgctcacatgttctttcctgcgttatcccctgattctgtgga
taaccgtattaccgcctttgagtgagctgataccgctcgccgcagccgaa
cgaccgagcgcagcgagtcagtgagcgaggaagcggaagagcgcctgatg
cggtattttctccttacgcatctgttgcggtatttcacaccgcatttggt
gcactctcagtacaatctgctctgatgccgcatagttaagccagtataca
ctccgctatcgctacgtgactgggtcatggctgcgccccgacacccgcca
acacccgctgacgcgccctgacgggcttgtctgctcccggcatccgctta
cagacaagctgtgaccgtctccgggagctgcatgtgtcagaggttttcac
cgtcatcaccgaaacgcgcgaggcagctgcggtaaagctcatcagcgtgg -continued tcgtgaagcgattcacagatgtctgcctgttcatccgcgtccagctcgtt
gagtttctccagaagcgttaatgtctggcttctgataaagcgggccatgt
taagggcggttttttcctgtttggtcactgatgcctccgtgtaagggga
tttctgttcatgggggtaatgataccgatgaaacgagagaggatgctcac
gatacgggttactgatgatgaacatgcccggttactggaacgttgtgagg
gtaaacaactggcggtatggatgcggcgggaccagagaaaaatcactcag
ggtcaatgccagcgcttcgttaatacagatgtaggtgttccacagggtag
ccagcagcatcctgcgatgcagatccggaacataatggtgcagggcgctg
acttccgcgtttccagactttacgaaacacggaaaccgaagaccattcat
gttgttgctcaggtcgcagacgttttgcagcagcagtcgcttcacgttcg
ctcgcgtatcggtgattcattctgctaaccagtaaggcaaccccgccagc
ctagccgggtcctcaacgacaggagcacgatcatgcgcacccgtggccag
gacccaacgctgcccgagatgcgccgcgtgcggctgctggagatggcgga
cgcgatggatatgttctgccaaggggtggtttgcgcattcacagttctcc
gcaagaattgattggctccaattcttggagtggtgaatccgttagcgagg
tgccgccggcttccattcaggtcgaggtggcccggctccatgcaccgcga
cgcaacgcggggaggcagacaaggtatagggcggcgcctacaatccatgc
caacccgttccatgtgctcgccgaggcggcataaatcgccgtgacgatca
gcggtccagtgatcgaagttaggctggtaagagccgcgagcgatccttga
agctgtccctgatggtcgtcatctacctgcctggacagcatggcctgcaa
cgcgggcatcccgatgccgccggaagcgagaagaatcataatggggaagg
ccatccagcctcgcgtcgcgaacgccagcaagacgtagcccagcgcgtcg
gccgccatgccggcgataatggcctgcttctcgccgaaacgtttggtggc
gggaccagtgacgaaggcttgagcgagggcgtgcaagattccgaataccg
caagcgacaggccgatcatcgtcgcgctccagcgaaagcggtcctcgccg
aaaatgacccagagcgctgccggcacctgtcctacgagttgcatgataaa
gaagacagtcataagtgcggcgacgatagtcatgccccgcgcccaccgga
aggagctgactgggttgaaggctctcaagggcatcggtcgacgctctccc
ttatgcgactcctgcattaggaagcagcccagtagtaggttgaggccgtt
gagcaccgccgccgcaaggaatggtgcatgcaaggagatggcgcccaaca
gtcccccggccacggggcctgccaccatacccacgccgaaacaagcgctc
atgagcccgaagtggcgagcccgatcttccccatcggtgatgtcggcgat
ataggcgccagcaaccgcacctgtggcgccggtgatgccggccacgatgc
gtccggcgtagaggattcacaggacgggtgtggtcgccatgatcgcgtag
tcgatagtggctccaagtagcgaagcgagcaggactgggcggcggccaaa
gcggtcggacagtgctccgagaacgggtgcgcatagaaattgcatcaacg
catatagcgctagcagcacgccatagtgactggcgatgctgtcggaatgg
acgatatcccgcaagaggcccggcagtaccggcataaccaagcctatgcc -continued tacagcatccagggtgacggtgccgaggatgacgatgagcgcattgttag atttcatacacggtgcctgactgcgttagcaaatttaactgtgataaacta ccgcattaaagcttatcgatgataagctgtcaaacatgagaa pBR-CBST-CTX-M-15

SEQ ID 7 ttcttgaagacgaaagggcctcgtgatacgcctatttttataggttaatg tcatgataataatggtttcttagacgtcaggtggcacttttcggggaaat gtgcgcggaaccccctatttgtttatttttctaaatacattcaaatatgta tccgctcatgagacaataaccctgataaatgcttcaataatattgaaaaa ggaagagtcatATGGAATCTGTTAAATCAGCGAGTTGAGATCAAAAAATC

TGACCTTGTTAACTATAATCCGATTGCGGAAAAGCACGTCAATGGGACGA

TGTCACTGGCTGAGCTTAGCGCGGCCGCGCTACAGTACAGCGATAACGTG

GCGATGAATAAGCTGATTGCTCACGTTGGCGGCCCGGCTAGCGTCACCGC

GTTCGCCCGACAGCTGGGAGACGAAACGTTCCGTCTCGACCGTACCGAGC

CGACGTTAAACACCGCCATTCCGGGCGATCCGCGTGATACCACTTCACCT

CGGGCAATGGCGCAAACTCTGCGGAATCTGACGCTGGGTAAAGCATTGGG

CGACAGCCAACGGGCGCAGCTGGTGACATGGATGAAAGGCAATACCACCG

GTGCAGCGAGCATTCAGGCTGGACTGCCTGCTTCCTGGGTTGTGGGGGAT

AAAACCGGCAGCGTGGCTATGGCACCACCAACGATATCGCGGTGATCTG

GCCAAAAGATCGTGCGCCGCTGATTCTGGTCACTTACTTCACCCAGCCTC

AACCTAAGGCAGAAAGCCGTCGCGATGTATTAGCGTCGGCGGCTAAAATC

GTCACCGACGGTTTGTAAggatccctgtcagaccaagtttactcatatat actttagattgatttaaaacttcatttttaatttaaaaggatctaggtga agatcctttttgataatctcatgaccaaaatcccttaacgtgagttttcg ttccactgagcgtcagaccccgtagaaaagatcaaaggatcttcttgaga tccttttttttctgcgcgtaatctgctgcttgcaaacaaaaaaaccaccgc taccagcggtggtttgtttgccggatcaagagctaccaactcttttttccg aaggtaactggcttcagcagagcgcagataccaaatactgtccttctagt gtagccgtagttaggccaccacttcaagaactctgtagcaccgcctacat acctcgctctgctaatcctgttaccagtggctgctgccagtggcgataag tcgtgtcttaccgggttggactcaagacgatagttaccggataaggcgca gcggtcgggctgaacggggggttcgtgcacacagcccagcttggagcgaa cgacctacaccgaactgagatacctacagcgtgagctatgagaaagcgcc acgcttcccgaagggagaaaggcggacaggtatccggtaagcggcagggt cggaacaggagagcgcacgagggagcttccaggggaaacgcctggtatc tttatagtcctgtcgggtttcgccacctctgacttgagcgtcgatttttg tgatgctcgtcaggggggcggagcctatgaaaaacgccagcaacgcggc cttttttacggttcctggccttttgctggccttttgctcacatgttcttc ctgcgttatcccctgattctgtggataaccgtattaccgcctttgagtga gctgataccgctcgccgcagccgaacgaccgagcgcagcgagtcagtgag cgaggaagcggaagagcgcctgatgcggtattttctccttacgcatctgt gcggtatttcacaccgcatttggtgcactctcagtacaatctgctctgat gccgcatagttaagccagtatacactccgctatcgctacgtgactgggtc atggctgcgccccgacacccgccaacacccgctgacgcgccctgacgggc ttgtctgctcccggcatccgcttacagacaagctgtgaccgtctccggga gctgcatgtgtcagaggttttcaccgtcatcaccgaaacgcgcgaggcag ctgcggtaaagctcatcagcgtggtcgtgaagcgattcacagatgtctgc ctgttcatccgcgtccagctcgttgagtttctccagaagcgttaatgtct ggcttctgataaagcgggccatgttaagggcggttttttcctgtttggtc actgatgcctccgtgtaagggggatttctgttcatgggggtaatgatacc gatgaaacgagagaggatgctcacgatacgggttactgatgatgaacatg cccggttactggaacgttgtgagggtaaacaactggcggtatggatgcgg cgggaccagagaaaaatcactcagggtcaatgccagcgcttcgttaatac agatgtaggtgttccacagggtagccagcagcatcctgcgatgcagatcc ggaacataatggtgcagggcgctgacttccgcgtttccagactttacgaa acacggaaaccgaagaccattcatgttgttgctcaggtcgcagacgtttt gcagcagtcgcttcacgttcgctcgcgtatcggtgattcattctgctaac cagtaaggcaaccccgccagcctagccgggtcctcaacgacaggagcacg atcatgcgcacccgtggccaggacccaacgctgcccgagatgcgccgcgt gcggctgctggagatggcggacgcgatggatatgttctgccaagggttgg tttgcgcattcacagttctccgcaagaattgattggctccaattcttgga gtggtgaatccgttagcgaggtgccgccggcttccattcaggtcgaggtg gcccggctccatgcaccgcgacgcaacgcggggaggcagacaaggtatag ggcggcgcctacaatccatgccaacccgttccatgtgctcgccgaggcgg cataaatcgccgtgacgatcagcggtccagtgatcgaagttaggctggta agagccgcgagcgatccttgaagctgtccctgatggtcgtcatctacctg cctggacagcatggcctgcaacgcgggcatcccgatgccgccggaagcga gaagaatcataatggggaaggccatccagcctcgcgtcgcgaacgccagc aagacgtagcccagcgcgtcggccgccatgccgcgataatggcctgctt ctcgccgaaacgtttggtggcgggaccagtgacgaaggcttgagcgaggg cgtgcaagattccgaataccgcaagcgacaggccgatcatcgtcgcgctc cagcgaaagcggtcctcgccgaaaatgacccagagcgctgccggcacctg tcctacgagttgcatgataaagaagacagtcataagtgcggcgacgatag tcatgccccgcgcccaccggaaggagctgactgggttgaaggctctcaag ggcatcggtcgacgctctcccttatgcgactcctgcattaggaagcagcc cagtagtaggttgaggccgttgagcaccgccgccgcaaggaatggtgcat gcaaggagatggcgcccaacagtcccccggccacggggcctgccaccata cccacgccgaaacaagcgctcatgagcccgaagtggcgagcccgatcttc cccatcggtgatgtcggcgatataggcgccagcaaccgcacctgtggcgc cggtgatgccggccacgatgcgtccggcgtagaggatcacaggacgggt gtggtcgccatgatcgcgtagtcgatagtggctccaagtagcgaagcgag caggactgggcggcggccaaagcggtcggacagtgctccgagaacgggtg -continued cgcatagaaattgcatcaacgcatatagcgctagcagcacgccatagtga
ctggcgatgctgtcggaatggacgatatcccgcaagaggcccggcagtac
cggcataaccaagcctatgcctacagcatccagggtgacggtgccgagga
tgacgatgagcgcattgttagatttcatacacggtgcctgactgcgttag
caatttaactgtgataaactaccgcattaaagcttatcgatgataagctg
tcaaacatgagaa pBR-CBST-SHV-12

SEQ ID 8
ttcttgaagacgaaagggcctcgtgatacgcctatttttataggttaatg
tcatgataataatggtttcttagacgtcaggtggcacttttcggggaaat
gtgcgcggaaccccatttgtttatttttctaaatacattcaaatatgta
tccgctcatgagacaataaccctgataaatgcttcaataatattgaaaaa
ggaagagtcatATGCGTTATATTCGCCTGTGTATTATCTCCCTGTTAGCC
ACCCTGCCGCTGGCGGTACACGCCAGCCCGCAGCCGCTTGAGCAAATTAA
ACAAAGCGAAAGCCAGCTGTCGGGCCGCGTAGGCATGATAGAAATGGATC
TGGCCAGCGGCCGCACGCTGACCGCCTGGCGCGCCGATGAACGCTTTCCC
ATGATGAGCACCTTTAAAGTAGTGCTCTGCGGCGCAGTGCTGGCGCGGGT
GGATGCCGGTGACGAACAGCTGGAGCGAAAGATCCACTATCGCCAGCAGG
ATCTGGTGGACTACTCGCCGGTCAGCGAAAAACACCTTGCCGACGGCATG
ACGGTCGGCGAACTCTGCGCCGCCGCCATTACCATGAGCGATAACAGCGC
CGCCAATCTGCTGCTGGCCACCGTCGGCGGCCCCGCAGGATTGACTGCCT
TTTTGCGCCAGATCGGCGACAACGTCACCCGCCTTGACCGCTGGGAAACG
GAACTGAATGAGGCGCTTCCCGGCGACGCCCGCGACACCACTACCCCGGC
CAGCATGGCCGCGACCCTGCGCAAGCTGCTGACCAGCCAGCGTCTGAGCG
CCCGTTCGCAACGGCAGCTGCTGCAGTGGATGGTGGACGATCGGGTCGCC
GGACCGTTGATCCGCTCCGTGCTGCCGGCGGGCTGGTTTATCGCCGATAA
GACCGGAGCTAGCAAGCGGGGTGCGCGCGGGATTGTCGCCCTGCTTGGCC
CGAATAACAAAGCAGAGCGCATTGTGGTGATTTATCTGCGGGATACCCCG
GCGAGCATGGCCGAGCGAAATCAGCAAATCGCCGGGATCGGCGCGGCGCT
GATCGAGCACTGGCAACGCTAAggatccctgtcagaccaagtttactcat
atatactttagattgatttaaaacttcattttttaatttaaaaggatctag
gtgaagatcctttttgataatctcatgaccaaaatcccttaacgtgagtt
ttcgttccactgagcgtcagaccccgtagaaaagatcaaaggatcttctt
gagatcctttttttctgcgcgtaatctgctgcttgcaaacaaaaaaacca
ccgctaccagcggtggtttgtttgccggatcaagagctaccaactttttta
ccgaaggtaactggcttcagcagagcgcagataccaaatactgtccttct
agtgtagccgtagttaggccaccacttcaagaactctgtagcaccgccta
catacctcgctctgctaatcctgttaccagtggctgctgccagtggcgat
aagtcgtgtcttaccgggttggactcaagacgatagttaccggataaggc
gcagcggtcgggctgaacggggggttcgtgcacacagcccagcttggagc
gaacgacctacaccgaactgagatacctacagcgtgagctatgagaaagc
gccacgcttcccgaagggagaaaggcggacaggtatccggtaagcggcag ggtcggaacaggagagcgcacgagggagcttccaggggaaacgcctggt
atctttatagtcctgtcgggtttcgccacctctgacttgagcgtcgattt
ttgtgatgctcgtcaggggggcggagcctatggaaaaacgccagcaacgc
ggcctttttacggttcctggccttttgctggccttttgctcacatgttct
ttcctgcgttatcccctgattctgtggataaccgtattaccgcctttgag
tgagctgataccgctcgccgcagccgaacgaccgagcgcagcgagtcagt
gagcgaggaagcggaagagcgcctgatgcggtattttctccttacgcatc
tgtgcggtatttcacaccgcatttggtgcactctcagtacaatctgctct
gatgccgcatagttaagccagtatacactccgctatcgctacgtgactgg
gtcatggctgcgccccgacacccgccaacacccgctgacgcgccctgacg
ggcttgtctgctcccggcatccgcttacagacaagctgtgaccgtctccg
ggagctgcatgtgtcagaggttttcaccgtcatcaccgaaacgcgcgagg
cagctgcggtaaagctcatcagcgtggtcgtgaagcgattcacagatgtc
tgcctgttcatccgcgtccagctcgttgagtttctccagaagcgttaatg
tctggcttctgataaagcgggccatgttaagggcggttttttcctgtttg
gtcactgatgcctccgtgtaaggggggatttctgttcatgggggtaatgat
accgatgaaacgagagaggatgctcacgatacgggttactgatgatgaac
atgcccggttactggaacgttgtgagggtaaacaactggcggtatggatg
cggcgggaccagagaaaaatcactcagggtcaatgccagcgcttcgttaa
tacagatgtaggtgttccacagggtagccagcagcatcctgcgatgcaga
tccggaacataatggtgcagggcgctgacttccgcgtttccagactttac
gaaacacggaaaccgaagaccattcatgttgttgctcaggtcgcagacgt
tttgcagcagcagtcgcttcacgttcgctcgcgtatcggtgattcattct
gctaaccagtaaggcaacccggccagcctagccgggtcctcaacgacagg
agcacgatcatgcgcacccgtggccaggacccaacgctgcccgagatgcg
ccgcgtgcggctggagatggcggacgcgatggatatgttctgccaagggt
tggtttgcgcattcacagttctccgcaagaattgattggctccaattctt
ggagtggtgaatccgttagcgaggtgccgccggcttccattcaggtcgag
gtggcccggctccatgcaccgcgacgcaacgcggggaggcagacaaggta
tagggcggcgcctacaatccatgccaacccgttccatgtgctcgccgagg
cggcataaatcgccgtgacgatcagcggtccagtgatcgaagttaggctg
gtaagagccgcgagcgatccttgaagctgtccctgatggtcgtcatctac
ctgcctggacagcatggcctgcaacgcgggcatcccgatgccgccgaag
cgagaagaatcataatggggaaggccatccagcctcgcgtcgcgaacgcc
agcaagacgtagcccagcgcgtcggccgccatgccggcgataatggcctg
cttctcgccgaaacgtttggtggcgggaccagtgacgaaggcttgagcga
gggcgtgcaagattccgaataccgcaagcgacaggcgatcatcgtcgcg
ctccagcgaaagcggtcctcgcctgaaaatgacccagagcgctgccggcac
ctgtcctacgagttgcatgataaagaagacagtcataagtgcggcgacga
tagtcatgccccgcgcccaccggaaggagctgactgggttgaaggctctc -continued

```
aagggcatcggtcgacgctctcccttatgcgactcctgcattaggaagca
gcccagtagtaggttgaggccgttgagcaccgccgccgcaaggaatggtg
catgcaaggagatggcgcccaacagtccccggccacggggcctgccacc
atcccacgccgaaacaagcgctcatgagcccgaagtggcgagcccgatc
ttccccatcggtgatgtcggcgatataggcgcagcaaccgcacctgtgg
cgccggtgatgccggccacgatgcgtccggcgtagaggattcacaggacg
ggtgtggtcgccatgatcgcgtagtcgatagtggctccaagtagcgaagc
gagcaggactgggcggcggccaaagcggtcggacagtgctccgagaacgg
gtgcgcatagaaattgcatcaacgcaatatagcgctagcagcacgccata
gtgactggcgatgctgtcggaatggacgatatcccgcaagaggcccggca
gtaccggcataaccaagcctatgcctacagcatccagggtgacggtgccg
aggatgacgatgagcgcattgttagatttcatacacggtgcctgactgcg
ttagcaatttaactgtgataaactaccgcattaaagcttatcgatgataa
gctgtcaaacatgagaa
``` pBR-CBST-P99

SEQ ID 9

```
ttcttgaagacgaaagggcctcgtgatacgcctatttttataggttaatg
tcatgataataatggtttcttagacgtcaggtggcacttttcggggaaat
gtgcgcggaaccccctatttgtttatttttctaaatacattcaaatatgta
tccgctcatgagacaataaccctgataaatgcttcaataatattgaaaaag
gaagagtcatATGATGAGAAAATCCCTTTGCTGCGCCCTGCTGCTCGGCA
TCTCTTGCTCTGCTCTCGCCACGCCAGTGTCAGAAAAACAGCTGGCGGAG
GTGGTCGCGAATACGATTACCCCGCTGATGAAAGCCCAGTCTGTTCCAGG
CATGGCGGTGGCCGTTATTTATCAGGGAAAACCGCACTATTACACATTTG
GCAAGGCCGATATCGCGGCGAATAAACCCGTTACGCCTCAGACCCTGTTC
GAGCTGGGTTCTATAAGTAAAACCTTCACCGGCGTTTTAGGTGGGGATGC
CATTGCTCGCGGTGAAATTTCGCTGGACGATGCGGTGACCAGATACTGGC
CACAGCTGACGGGCAAGCAGTGGCAGGGTATTCGTATGCTGGATCTCGCC
ACCTACACCGCTGGCGGCCTGCCGCTACAGGTACCGGATGAGGTCACGGA
TAACGCCTCCCTGCTGCGCTTTTATCAAAACTGGCAGCCGCAGTGGAAGC
CTGGCACAACGCGTCTTTACGCCAACGCCAGCATCGGTCTTTTTGGTGCG
CTGGCGGTCAAACCTTCTGGCATGCCCTATGAGCAGGCCATGACGACGCG
GGTCCTTAAGCCGCTCAAGCTGGACCATACCTGGATTAACGTGCCGAAAG
CGGAAGAGGCGCATTACGCCTGGGGCTATCGTGACGGTAAAGCGGTGCGC
GTTTCGCCGGGTATGCTGGATGCACAAGCCTATGGCGTGAAAACCAACGT
GCAGGATATGGCGAACTGGGTCATGGCAAACATGGCGCCGGAGAACGTTG
CTGATGCCTCACTTAAGCAGGGCATCGCGCTGGCGCAGTCGCGCTACTGG
CGTATCGGGTCAATGTATCAGGGTCTGGGCTGGGAGATGCTCAACTGGCC
CGTGGAGGCCAACACGGTGGTCGAGGGCAGCGACAGTAAGGTAGCACTGG
CGCCGTTGCCCGTGGCAGAAGTGAATCCACCGGCTCCCCCGGTCAAAGCG
TCCTGGGTCCATAAAACGGGCTCTACTGGCGGGTTTGGCAGCTACGTGGC
CTTTATTCCTGAAAAGCAGATCGGTATTGTGATGCTCGCGAATACAAGCT
```

-continued

```
ATCCGAACCCGGCACGCGTTGAGGCGGCATACCATATCCTCGAGGCGCTA
CAGTAAggatccCTGTCAGACCAAGTTTACTCATATATACTTTAGATTGA
TTTAAAACTTCATTTTTAATTTAAAAGGATCTAGGTGAAGATCCTTTTTG
ATAATCTCATGACCAAAATCCCTTAACGTGAGTTTTCGTTCCACTGAGCG
TCAGACCCCGTAGAAAAGATCAAAGGATCTTCTTGAGATCCTTTTTTTCT
GCGCGTAATCTGCTGCTTGCAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCC
TGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAA
GAGCGCCTGATGCGGTATTTTCTCCTTACGCATCTGTGCGGTATTTCACA
CCGCATTTGGTGCACTCTCAGTACAATCTGCTCTGATGCCGCATAGTTAA
GCCAGTATACACTCCGCTATCGCTACGTGACTGGGTCATGGCTGCGCCCC
GACACCCGCCAACACCCGCTGACGCGCCCTGACGGGCTTGTCTGCTCCCG
GCATCCGCTTACAGACAAGCTGTGACCGTCTCCGGGAGCTGCATGTGTCA
GAGGTTTTCACCGTCATCACCGAAACGCGCGAGGCAGCTGCGGTAAAGCT
CATCAGCGTGGTCGTGAAGCGATTCACAGATGTCTGCCTGTTCATCCGCG
TCCAGCTCGTTGAGTTTCTCCAGAAGCGTTAATGTCTGGCTTCTGATAAA
GCGGGCCATGTTAAGGGCGGTTTTTTCCTGTTTGGTCACTGATGCCTCCG
TGTAAGGGGGATTTTCTGTTCATGGGGGTAATGATACCGATGAAACGAGA
GAGGATGCTCACGATACGGGTTACTGATGATGAACATGCCCGGTTACTGG
AACGTTGTGAGGGTAAACAACTGGCGGTATGGATGCGGCGGGACCAGAGA
AAAATCACTCAGGGTCAATGCCAGCGCTTCGTTAATACAGATGTAGGTGT
TCCACAGGGTAGCCAGCAGCATCCTGCGATGCAGATCCGGAACATAATGG
TGCAGGGCGCTGACTTCCGCGTTTCCAGACTTTACGAAACACGGAAACCG
AAGACCATTCATGTTGTTGCTCAGGTCGCAGACGTTTTGCAGCAGCAGTC
GCTTCACGTTCGCTCGCGTATCGGTGATTCATTCTGCTAACCAGTAAGGC
AACCCCGCCAGCCTAGCCGGGTCCTCAACGACAGGAGCACGATCATGCGC
ACCCGTGGCCAGGACCCAACGCTGCCCGAGATGCGCCGCGTGCGGCTGCT
GGAGATGGCGGACGCGATGGATATGTTCTGCCAAGGGTTGGTTTGCGCAT
```

-continued tcacagttctccgcaagaattgattggctccaattcttggagtggtgaat
ccgttagcgaggtgccgccggcttccattcaggtcgaggtggccggctc
catgcaccgcgacgcaacgcggggaggcagacaaggtatagggcggcgcc
tacaatccatgccaacccgttccatgtgctcgccgaggcggcataaatcg
ccgtgacgatcagcggtccagtgatcgaagttaggctggtaagagccgcg
agcgatccttgaagctgtccctgatggtcgtcatctacctgcctggacag
catggcctgcaacgcgggcatcccgatgccgccggaagcgagaagaatca
taatggggaaggccatccagcctcgcgtcgcgaacgccagcaagacgtag
cccagcgcgtcggccgccatgccggcgataatggcctgcttctcgccgaa
acgtttggtggcgggaccagtgacgaaggcttgagcgagggcgtgcaaga
ttccgaataccgcaagcgacaggccgatcatcgtcgcgctccagcgaaag
cggtcctcgccgaaaatgacccagagcgctgccggcacctgtcctacgag
ttgcatgataaagaagacagtcataagtgcggcgacgatagtcatgcccc
gcgcccaccggaaggagctgactgggttgaaggctctcaagggcatcggt
cgacgctctcccttatgcgactcctgcattaggaagcagcccagtagtag
gttgaggccgttgagcaccgccgccgcaaggaatggtgcatgcaaggaga
tggcgcccaacagtcccccggccacggggcctgccaccataccacgccga
aacaagcgctcatgagcccgaagtggcgagcccgatcttccccatcggtg
atgtcggcgatataggcgccagcaaccgcacctgtggcgccggtgatgcc
ggccacgatgcgtccggcgtagaggattcacaggacgggtgtggtcgcca
tgatcgcgtagtcgatagtggctccaagtagcgaagcgagcaggactggg
cggcggccaaagcggtcggacagtgctccgagaacgggtgcgcatagaaa
ttgcatcaacgcatatagcgctagcagcacgccatagtgactggcgatgc
tgtcggaatggacgatatcccgccgaggcccggcagtaccggcataacca
agcctatgcctacagcatccagggtgacggtgccgaggatgacgatgagc
gcattgttagatttcatacacggtgcctgactgcgttagcaatttaactg
tgataaactaccgcattaaagcttatcgatgataagctgtcaaacatgag
aa
pBR-CBST-OXA-15

SEQ ID 10
ttcttgaagacgaaagggcctcgtgatacgcctatttttataggttaatg
tcatgataataatggtttcttagacgtcaggtggcacttttcggggaaat
gtgcgcggaacccctatttgtttatttttctaaatacattcaaatatgta
tccgctcatgagacaataaccctgataaatgcttcaataatattgaaaaa
ggaagagtcatATGGCAATCCGAATCTTCGCGATACTTTTCTCCATTTTT
TCTCTTGCCACTTTCGCGCATGCGCAAGAAGGCACGCTAGAACGTTCTGA
CTGGAGGAAGTTTTTCAGCGAATTTCAAGCCAAAGGCACGATAGTTGTGG
CAGACGAACGCCAAGCGGATCGTGCCATGTTGGTTTTTGATCCTGTGCGA
TCGAAGAAACGCTACTCGCCTGCATCGACATTCAAGATACCTCATACACT
TTTTGCACTTGATGCAGGCGCTGTTCGTGATGAGTTCCAGATTTTTCGAT
GGGACGGCGTTAACAGGGGCTTTGCAGGCCACAATCAAGACCAAGATTTG
CGATCAGCAATGCGGAATTCTACTGTTTGGGTGTATGAGCTATTTGCAAA
GGAAATTGGTGATGACAAAGCTCGGCGCTATTTGAAGAAAATCGACTATG
GCAACGCCGGTCCTTCGACAAGTAATGGCGATTACTGGATAGAAGGCAGC
CTTGCAATCTCGGCGCAGGAGCAAATTGCATTTCTCAGGAAGCTCTATCG
TAACGAGCTGCCCTTTCGGGTAGAACATCAGCGCTTGGTCAAGGATCTCA
TGATTGTGGAAGCCGGTCGCAACTGGATACTGCGTGCAAAGACGGGCTGG
GAAGGCCGTATGGGTTGGTGGTAGGATGGGTTGAGTGGCCGACTGGCTC
CGTATTCTTCGCACTGAATATTGATACGCCAAACAGAATGGATGATCTTT
TCAAGAGGGAGGCAATCGTGCGGGCAATCCTTCGCTCTATTGAAGCGTTA
CCGCCCAACCCGGCAGTCAACTCGGACGCTGCGCGATAAggatccctgtc
agaccaagtttactcatatatactttagattgatttaaaacttcattttt
aatttaaaaggatctaggtgaagatcctttt gataatctcatgaccaaaa
tcccttaacgtgagattttcgttccactgagcgtcagacccc gtagaaaa
gatcaaaggatcttcttgagatcctttttttctgcgcgtaatctgctgct
tgcaaacaaaaaaaccaccgctaccagcggtggtttgtttgccggatcaa
gagctaccaactctttttccgaaggtaactggcttcagcagagcgcagat
accaaatactgtccttctagtgtagccgtagttaggccaccacttcaaga
actctgtagcaccgcctacatacctcgctctgctaatcctgttaccagtg
gctgctgccagtggcgataagtcgtgtcttaccgggttggactcaagacg
atagttaccggataaggcgcagcggtcgggctgaacggggggttcgtgca
cacagcccagcttggagcgaacgacctacaccgaactgagatacctacag
cgtgagctatgagaaagcgccacgcttcccgaagggagaaaggcggacag
gtatccggtaagcggcagggtcggaacaggagagcgcacgagggagcttc
cagggggaaacgcctggtatctttatagtcctgtcgggtttcgccacctc
tgacttgagcgtcgatttttgtgatgctcgtcaggggggcggagcctatg
gaaaaacgccagcaacgcggcctttttacggttcctggccttttgctggc
cttttgctcacatgttctttcctgcgttatcccctgattctgtggataac
cgtattaccgcctttgagtgagctgataccgctcgccgcagccgaacgac
cgagcgcagcgagtcagtgagcgaggaagcggaagagcgcctgatgcggt
attttctccttacgcatctgtgcggtatttcacaccgcatttggtgcact
ctcagtacaatctgctctgatgccgcatagttaagccagtatacactccg
ctatcgctacgtgactgggtcatggctgcgccccgacacccgccaacacc
cgctgacgcgccctgacgggcttgtctgctcccggcatccgcttacagac
aagctgtgaccgtctccgggagctgcatgtgtcagaggttttcaccgtca
tcaccgaaacgcgcgaggcagctgcggtaaagctcatcagcgtggtcgtg
aagcgattcacagatgtctgcctgttcatccgcgtccagctcgttgagtt
tctccagaagcgttaatgtctggcttctgataaagcgggccatgttaagg
gcgttttttcctgtttggtcactgatgcctccgtgtaagggggatttct
gttcatgggggtaatgataccgatgaaacgagagaggatgctcacgatac
gggttactgatgatgaacatgcccggttactggaacgttgtgagggtaaa
caactggcggtatggatgcggcgggaccagagaaaaatcactcagggtca -continued
```
atgccagcgcttcgttaatacagatgtaggtgttccacagggtagccagc
agcatcctgcgatgcagatccggaacataatggtgcagggcgctgacttc
cgcgtttccagactttacgaaacacggaaaccgaagaccattcatgttgt
tgctcaggtcgcagacgttttgcagcagcagtcgcttcacgttcgctcgc
gtatcggtgattcattctgctaaccagtaaggcaacccgccagcctagc
cgggtcctcaacgacaggagcacgatcatgcgcaccgtggccaggaccc
aacgctgcccgagatgcgccgcgtgcggctgctggagatggcggacgcga
tggatatgttctgccaagggttggtttgcgcattcacagttctccgcaag
aattgattggctccaattcaggagtggtgaatccgttagcgaggtgccgc
cggcttccattcaggtcgaggtggcccggctccatgcaccgcgacgcaac
gcggggaggcagacaaggtatagggcggcgcctacaatccatgccaaccc
gttccatgtgctcgccgaggcggcataaatcgccgtgacgatcagcggtc
cagtgatcgaagttaggctggtaagagccgcgagcgatccttgaagctgt
ccctgatggtcgtcatctacctgcctggacagcatggcctgcaacgcggg
catcccgatgccgccggaagcgagaagaatcataatggggaaggccatcc
agcctcgcgtcgcgaacgccagcaagacgtagcccagcgcgtcggccgcc
atgccggcgataatggcctgcttctcgccgaaacgtttggtggcgggacc
agtgacgaaggcttgagcgagggcgtgcaagattccgaataccgcaagcg
acaggccgatcatcgtcgcgctccagcgaaagcggtcctcgccgaaaatg
acccagagcgctgccggcacctgtcctacgagttgcatgataaagaagac
agtcataagtgcggcgacgatagtcatgccccgcgccaccggaaggagc
tgactgggttgaaggctctcaagggcatcggtcgacgctctcccttatgc
gactcctgcattaggaagcagcccagtagtaggagaggccgagagcaccg
ccgccgcaaggaatggtgcatgcaaggagatggcgcccaacagtcccccg
gccacggggcctgccaccatacccacgccgaaacaagcgctcatgagccc
gaagtggcgagcccgatcttccccatcggtgatgtcggcgatataggcgc
cagcaaccgcacctgtggcgccggtgatgccggccacgatgcgtccggcg
tagaggattcacaggacgggtgtggtcgccatgatcgcgtagtcgatagt
ggctccaagtagcgaagcgagcaggactgggcggcggccaaagcggtcgg
acagtgctccgagaacgggtgcgcatagaaattgcatcaacgcatatagc
gctagcagcacgccatagtgactggcgatgctgtcggaatggacgatatc
ccgcaagaggccggcagtaccggcataaccaagcctatgcctacagcat
ccagggtgacggtgccgaggatgacgatgagcgcattgttagatttcata
cacggtgcctgactgcgttagcaatttaactgtgataaaactaccgcatta
aagcttatcgatgataagctgtcaaacatgagaa
```

Example 23

Synergy MIC Assay

The synergy MIC (sMIC) assay determines the concentration of the BLI required to potentiate the activity of a fixed concentration of a β-lactam antibiotic against β-lactamase producing bacterial strains. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition"). The assay is set-up by serially diluting the BLI across 11 of the 12 wells in each row of a 96-well broth microdilution assay plate, adding the β-lactam at a fixed concentration to all wells in the assay plate, inoculating the assay plate with bacterial strains, and determining the lowest concentration of BLI required to inhibit overnight bacterial growth. Bacterial growth in the $12^{th}$ well of the assay plate, which contains the β-lactam at a fixed concentration but does not contain any BLI, demonstrates that the bacterial strains are resistant to the β-lactam antibiotic (e.g. ceftolozane) at the fixed concentration of 4 μg/mL.

To prepare for MIC testing, frozen glycerol stocks of laboratory engineered, isogenic *E. coli* strains, which contain cloned β-lactamase expressing plasmids were used to streak for isolated colonies on rich, selective LB agar supplemented with 25 μg/mL tetracycline to maintain the plasmid. All strains were incubated at 37° C. for 18-24 hrs.

On the day of testing, primary cultures were started by scraping off 5-10 colonies from the tetracycline supplemented LB plates containing engineered strains. The engineered strain material was suspended in CAMHB (supplemented with tetracycline at 25 μg/mL) in 14 mL culture tubes. All strains were incubated at 37° C. with aeration (200 rpm) for 2 hrs until the OD600 was ≥0.1.

The two compound components of the assay were each prepared in CAMHB and added to the 96-well broth microdilution assay plates. 50 μL, of the BLI was added to each well of the assay plate in 2-fold dilutions with final concentrations ranging from 128 to 0.13 μg/mL. 25 μL, of the β-lactam was added to all wells in the broth microdilution plates at a final concentration of 4 μg/mL. Inoculum cultures were prepared by standardizing the primary cultures to OD600=0.1 and then adding 20 μL of the adjusted primary culture per 1 mL CAMHB for clinical strains or CAMHB (supplemented with tetracycline at 100 μg/mL) for isogenic strains, so that the final inoculum density was ~$10^5$ colony forming units per milliliter. Diluted inoculum cultures were used to inoculate 25 μL per well in 96-well broth microdilution assay plates. The final volume of each well was 100 μL, and contained a BLI at different concentrations, a β-lactam at 4 μg/mL concentration, the bacterial culture at an OD600 of approximately 0.001 and when necessary tetracycline at 25 ug/mL.

Interpreting the sMIC Data:

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. sMIC values were defined as the lowest concentration producing no visible turbidity.

The sMIC values represent the amount of BLI required to potentiate the activity of 4 μg/ml of CXA-101 (Ceftolozane) or ceftazidime to inhibit the growth of the β-lactamase producing bacteria.

sMIC values of representative compounds are shown in Table II.

Example 24

Inhibition Kinetics

Inhibition or inactivation of KPC-2 by test inhibitors was assessed using 100 μM nitrocefin (NCF) as a reporter substrate. Assays were performed in 1×PBS pH 7.4, 0.1 mg/ml BSA, in 96-well half area plates, 50 µl reaction volume. NCF was dissolved in DMSO and diluted in assay buffer. Test inhibitors were dissolved in water or DMSO and serially diluted in the assay with final concentrations between 2000-0.195 µM.

The enzyme activity in the presence of varying concentrations of test inhibitor was determined by monitoring the hydrolysis of NCF spectrophotometrically at 486 nm, for 5 minutes, 25° C., using a SpectraMax Plus384 microplate reader with SoftMax Pro software (Molecular Devices). Data analysis was performed using GraphPad Prism (GraphPad Software, Inc.).

Progress curves were fit to a first-order rate decay equation (Eq. 1) to determine $k_{observed}$ ($k_{obs}$).

$k_{obs}$ vs. inhibitor concentration [I] curves were then fit to Eq.2 to determine the inhibitor dissociation constant (K) and the first order rate constant of enzyme inactivation at infinite inhibitor concentration ($k_{inact}$). Table III shows kinetics results from representative test compounds. A larger $k_{inact}$ K ratio indicates a more effective enzyme inactivator.

$$Y_t = V_0 * (1 - e^{(-k_{obs}*t)})/k_{obs} \qquad \text{Eq. 1}$$

Where Y is the absorbance at time t, $V_0$ is the uninhibited enzyme velocity, $k_{obs}$ is the observed rate constant of the enzyme inactivation.

$$k_{obs} = k_{inact} * [I]/([I] + K(1 + S/K_m)) \qquad \text{Eq. 2}$$

Where S is the NCF concentration, $K_m$ is the KPC-2 $K_m$ for NCF.

Biological data using the procedures described herein are shown for certain compounds in U.S. patent application Ser. Nos. 13/853,443, 13/853,498 and 13/853,506, the contents of which are incorporated herein by reference in their entirety.

We claim:

1. A process for preparing a compound of Formula (A-I):

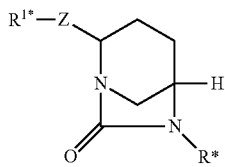

wherein

Z is selected from the group consisting of 1,3,4-oxadiazole, 1,2,4-oxadiazole, 1,3,4-thiadiazole and 1,2,4-thiadiazole;

R* is —OSO$_3$H; and

R$^{1*}$ is selected from:
a. hydrogen;
b.

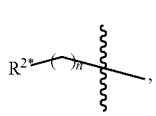

wherein
R$^{2*}$ is selected from

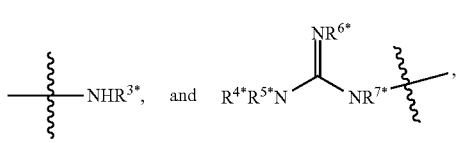

R$^{3*}$ is selected from hydrogen, (C$_1$-C$_3$)-alkyl, aminoalkyl, aminocycloalkyl, hydroxyalkyl,

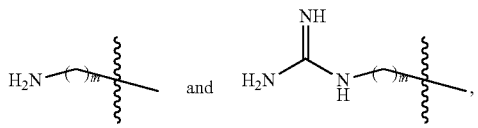

each of R$^{4*}$, R$^{5*}$, R$^{6*}$ and R$^{7*}$ is independently selected from hydrogen or (C$_1$-C$_6$)-alkyl, aminoalkyl, aminocycloalkyl, and hydroxyalkyl, provided that at least one of R$^{4*}$, R$^{5*}$, R$^{6*}$ and R$^{7*}$ is hydrogen, n is selected from 1, 2, 3 and 4, and m is selected from 1, 2 and 3;

c.

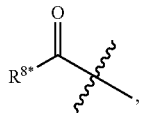

wherein R$^{8*}$ is selected from NH$_2$,

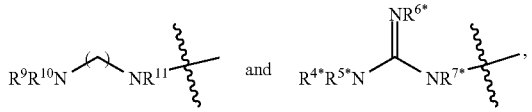

wherein each of R$^{4*}$, R$^{5*}$, R$^{6*}$ and R$^{7*}$ is as described previously and each of R$^9$, R$^{10}$, and R$^{11}$ is independently selected from hydrogen or (C$_1$-C$_6$)-alkyl, provided that at least one of R$^9$, R$^{10}$, and R$^{11}$ is hydrogen;

d. amino;

e.

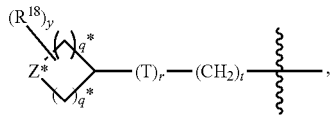

wherein Z* is selected from CR$^{12}$R$^{13}$ or NR$^{14}$, each of R$^{12}$ and R$^{13}$ is independently selected from H, NH$_2$ and

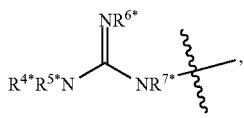

wherein each of R$^{4*}$, R$^{5*}$, R$^{6*}$ and R$^{7*}$ is as described previously, alternatively, R$^{12}$ and R$^{13}$ together with the carbon to which they are attached, form a cycloalkyl or heterocyclyl ring containing 4-6 ring members, R$^{14}$ is selected from H and

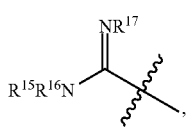

wherein each of R$^{15}$, R$^{16}$, and R$^{17}$ is independently selected from hydrogen, (C$_1$-C$_6$)-alkyl, aminoalkyl, aminocycloalkyl, and hydroxyalkyl, provided that at least one of R$^{15}$, R$^{16}$ and R$^{17}$ is hydrogen, R$^{18}$ is selected from NH$_2$ and

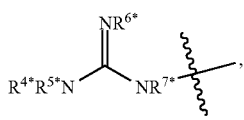

wherein each of R$^{4*}$, R$^{5*}$,
R$^{6*}$ and R$^{7*}$ is as described previously,
each of p* and q* is independently selected from 0, 1, 2 and 3,
T is selected from NH and O
t is selected from 0, 1, 2, 3, and 4, and
each of r and y is independently selected from 0 and 1;

f.

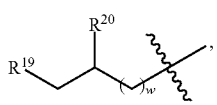

wherein $R^{19}$ is selected from $NH_2$ and

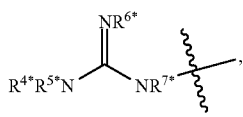

wherein each of $R^{4*}$,
$R^{5*}$, $R^{6*}$ and $R^{7*}$ is as described previously,
$R^{20}$ is selected from amino and hydroxyl, and
w is selected from 0 and 1;

g.

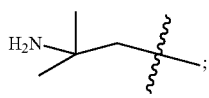 [SMILES: *CC(C)(C)N]

h.

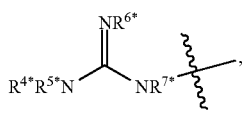

wherein each of $R^{4*}$, $R^{5*}$, $R^{6*}$ and $R^{7*}$ is as described previously;

i.

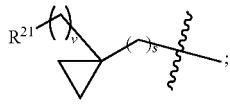

wherein $R^{21}$ is selected from $NH_2$, —$NH(C_1-C_3)$-alkyl and

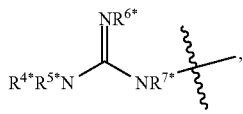

wherein each of $R^{4*}$, $R^{5*}$, $R^{6*}$ and $R^{7*}$ is as described previously,
s is selected from 0 and 1, and
v is selected from 0, 1, 2, and 3;

j.

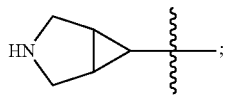

k.

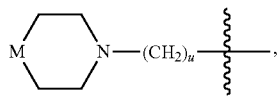

wherein M is selected from $NR^{22}$, $CR^{23}R^{24}$ and O, wherein $R^{22}$ is H or

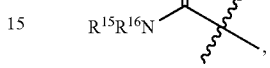

wherein each of $R^{15}$, $R^{16}$ and $R^{17}$ is as described previously,
each of $R^{23}$ and $R^{24}$ is independently selected from H, $NH_2$ and

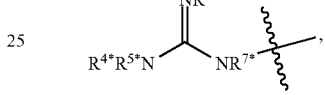

wherein each of $R^{4*}$, $R^{5*}$, $R^{6*}$ and $R^{7*}$ is as described previously, and
u is selected from 0, 1 and 2;

l.

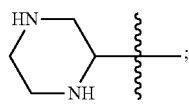

m.

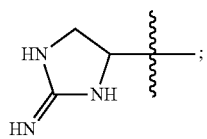 [SMILES: *C1CNC(=N)N1]

n.

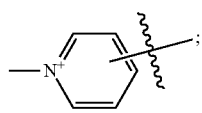

o. $(C_1-C_3)$-unsubstituted alkyl; and p.

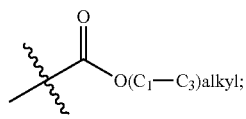

the process comprising the steps of:
(a) reacting compound 1 with lithium hydroxide to produce compound 2a:

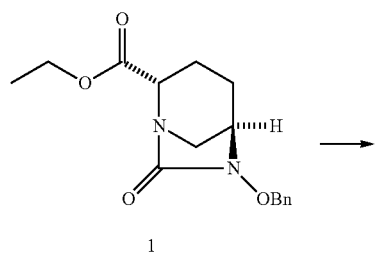

1

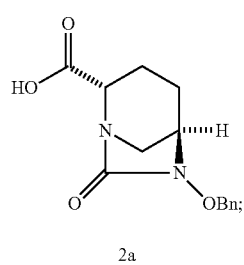

2a or
reacting compound 1 with lithium borohydride, followed by TEMPO-mediated oxidation to produce compound 2b:

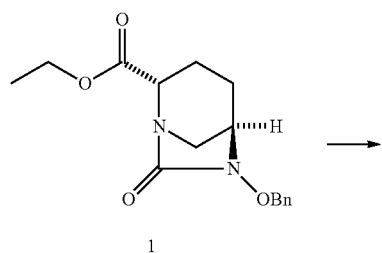

1

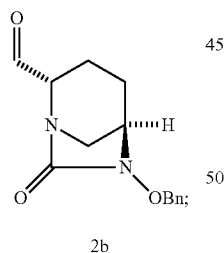

2b (b) converting the carboxylic acid of 2a or the aldehyde of 2b to a heterocyclic ring to produce compound 3:

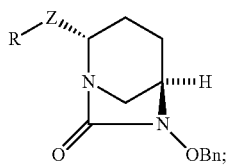

3

(c) debenzylating compound 3 to produce compound 4:

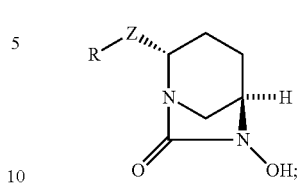

4 and
(d) reacting intermediate 4 with SO$_3$.pyridine complex to produce compound 5:

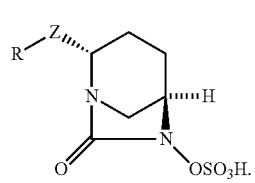

5

2. The process of claim 1, wherein compound of Formula (A-I) is the compound:

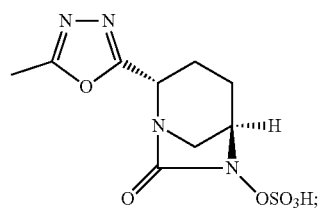

and
wherein
step (a) comprises reacting compound 1 with lithium hydroxide in THF/H$_2$O to produce compound 2a; and
step (b) comprises the steps of:
(1) reacting compound 2a with tert-butyl hydrazinecarboxylate to produce the compound:

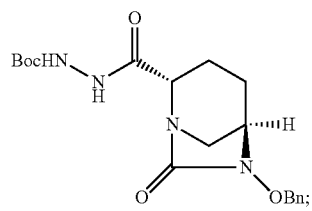 [SMILES: CC(C)(C)OC(=O)NNC(=O)[C@@H]1CC[C@@H]2CN1C(=O)N2OCc1ccccc1]

(2) reacting the product of step (1) with trifluoroacetic acid to produce the compound:

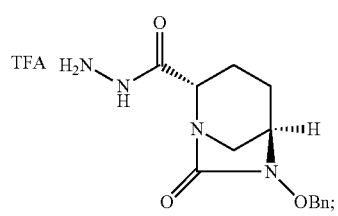 [SMILES: NNC(=O)[C@@H]1CC[C@@H]2CN1C(=O)N2OCc1ccccc1]

(3) reacting the product of step (2) with N-[(Dimethylamino)-1H-1,2,3-triazolo-[4,5-b]pyridin-1-ylmethylene]-N-methylmethanaminium hexafluorophosphate N-oxide (HATU) to produce the compound:

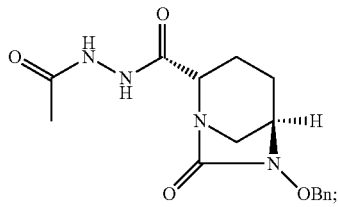

(4) reacting the product of step (3) with triflic anhydride to produce compound:

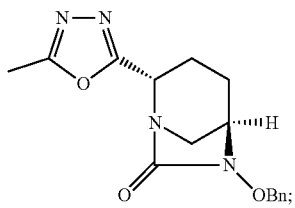 [SMILES: Cc1nnc([C@@H]2CC[C@@H]3CN2C(=O)N3OCc2ccccc2)o1]

step (c) comprises the step of reacting the product of step (b) with Pd/C and $H_2$ to produce the compound:

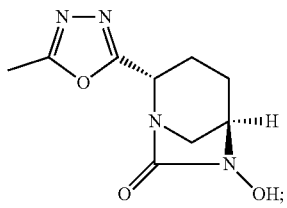 [SMILES: Cc1nnc([C@@H]2CC[C@@H]3CN2C(=O)N3O)o1]

and step (d) comprises reacting the product of step (c) with $SO_3$·pyridine complex to produce the compound:

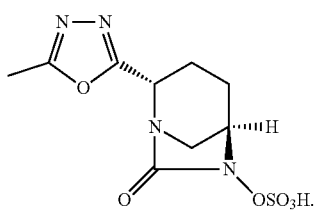

3. The process of claim 1, wherein compound 1 is produced by a process comprising the steps of:

(1) reacting the compound:

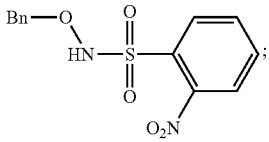

with the compound:

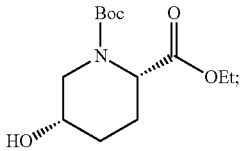 [SMILES: CCOC(=O)[C@@H]1CC[C@H](O)CN1C(=O)OC(C)(C)C]

to produce the compound:

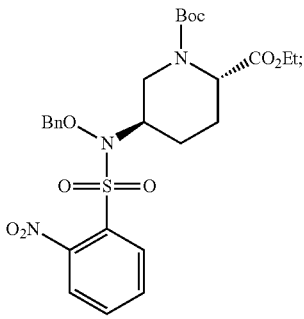 [SMILES: CCOC(=O)[C@@H]1CC[C@@H](N(OCc2ccccc2)S(=O)(=O)c2ccccc2[N+](=O)[O-])CN1C(=O)OC(C)(C)C]

(2) reacting the product of step (1) with lithium hydroxide monohydrate and 2-mercaptoacetic acid to produce the compound:

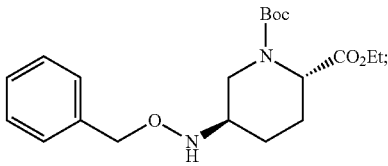 [SMILES: CCOC(=O)[C@@H]1CC[C@@H](NOCc2ccccc2)CN1C(=O)OC(C)(C)C]

(3) deprotecting the product of step (2) to produce the compound:

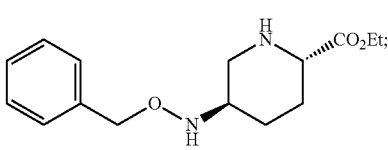 [SMILES: CCOC(=O)[C@@H]1CC[C@@H](NOCc2ccccc2)CN1]

and (4) reacting the product of step (3) with triphosgene such that compound 1 is formed.

* * * * *

```
                        SEQUENCE LISTING

<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: Sythetic primer: pBR-Pbla

<400> SEQUENCE: 1
cgcatatgac tcttcctttt tcaatattat tg                                 32

<210> SEQ ID NO 2
<211> LENGTH: 28
<212> TYPE: DNA
<213> ORGANISM: Artificial Sequence
<220> FEATURE:
<223> OTHER INFORMATION: Sythetic primer: pBR-vec-1

<400> SEQUENCE: 2
gcggatccct gtcagaccaa gtttactc                                      28

<210> SEQ ID NO 3
<211> LENGTH: 28
<212> TYPE: DNA
<213> ORGANISM: Artificial Sequence
<220> FEATURE:
<223> OTHER INFORMATION: Sythetic primer: Pbla-cat

<400> SEQUENCE: 3
gccatatgat ggagaaaaaa atcactgg                                      28

<210> SEQ ID NO 4
<211> LENGTH: 28
<212> TYPE: DNA
<213> ORGANISM: Artificial Sequence
<220> FEATURE:
<223> OTHER INFORMATION: Sythetic primer: Vec-1-cat

<400> SEQUENCE: 4
cgggatccct agagaatagg aacttcgg                                      28

<210> SEQ ID NO 5
<211> LENGTH: 4236
<212> TYPE: DNA
<213> ORGANISM: Artificial Sequence
<220> FEATURE:
<223> OTHER INFORMATION: Synthetic construct: pBR-CBST-cat
```

<400> SEQUENCE: 5

```
ttcttgaaga cgaaagggcc tcgtgatacg cctattttta taggttaatg tcatgataat    60
aatggtttct tagacgtcag gtggcacttt tcggggaaat gtgcgcggaa ccccctatttg   120
tttatttttc taaatacatt caaatatgta tccgctcatg agacaataac cctgataaat   180
gcttcaataa tattgaaaaa ggaagagtca tatggagaaa aaaatcactg gatataccac   240
cgttgatata tcccaatggc atcgtaaaga acatttttgag gcatttcagt cagttgctca   300
atgtacctat aaccagaccg ttcagctgga tattacggcc ttttttaaaga ccgtaaagaa   360
aaataagcac aagttttatc cggcctttat tcacattctt gcccgcctga tgaatgctca   420
tacggaattt cgtatggcaa tgaaagacgg tgagctggtg atatgggata gtgttcaccc   480
ttgttacacc gttttccatg agcaaactga acgttttca tcgctctgga gtgaatacca   540
cgacgatttc cggcagtttc tacacatata ttcgcaagat gtggcgtgtt acggtgaaaa   600
cctggcctat ttccctaaag ggtttattga gaatatgttt ttcgtctcag ccaatccctg   660
ggtgagtttc accagttttg atttaaacgt ggccaatatg gacaacttct tcgcccccgt   720
tttcactatg ggcaaatatt atacgcaagg cgacaaggtg ctgatgccgc tggcgattca   780
ggttcatcat gccgtctgtg atggcttcca tgtcggcaga atgcttaatg aattacaaca   840
gtactgcgat gagtggcagg gcggggcgta agtggcaggg cggggcgtaa ggcgcgccat   900
ttaaatgaag ttcctattcc gaagttccta ttctctaggg atccctgtca gaccaagttt   960
actcatatat actttagatt gatttaaaac ttcatttta atttaaaagg atctaggtga  1020
agatccttt tgataatctc atgaccaaaa tcccttaacg tgagttttcg ttccactgag  1080
cgtcagaccc cgtagaaaag atcaaaggat cttcttgaga tcctttttt ctgcgcgtaa  1140
tctgctgctt gcaaacaaaa aaaccaccgc taccagcggt ggtttgtttg ccggatcaag  1200
agctaccaac tctttttccg aaggtaactg gcttcagcag agcgcagata ccaaatactg  1260
tccttctagt gtagccgtag ttaggccacc acttcaagaa ctctgtagca ccgcctacat  1320
acctcgctct gctaatcctg ttaccagtgg ctgctgccag tggcgataag tcgtgtctta  1380
ccgggttgga ctcaagacga tagttaccgg ataaggcgca gcggtcgggc tgaacggggg  1440
gttcgtgcac acagcccagc ttggagcgaa cgacctacac cgaactgaga tacctacagc  1500
gtgagctatg agaaagcgcc acgcttcccg aagggagaaa ggcggacagg tatccggtaa  1560
gcggcagggt cggaacagga gagcgcacga gggagcttcc agggggaaac gcctggtatc  1620
tttatagtcc tgtcgggttt cgccacctct gacttgagcg tcgatttttg tgatgctcgt  1680
caggggggcg gagcctatgg aaaaacgcca gcaacgcggc ctttttacgg ttcctggcct  1740
tttgctggcc ttttgctcac atgttctttc ctgcgttatc ccctgattct gtggataacc  1800
gtattaccgc ctttgagtga gctgataccg ctcgccgcag ccgaacgacc gagcgcagcg  1860
agtcagtgag cgaggaagcg gaagagcgcc tgatgcggta ttttctcctt acgcatctgt  1920
gcggtatttc acaccgcatt tggtgcactc tcagtacaat ctgctctgat gccgcatagt  1980
taagccagta tacactccgc tatcgctacg tgactgggtc atggctgcgc ccgacaccc   2040
gccaacaccc gctgacgcgc cctgacgggc ttgtctgctc ccggcatccg cttacagaca  2100
agctgtgacc gtctccggga gctgcatgtg tcagaggttt tcaccgtcat caccgaaacg  2160
cgcgaggcag ctgcggtaaa gctcatcagc gtggtcgtga agcgattcac agatgtctgc  2220
ctgttcatcc gcgtccagct cgttgagttt ctccagaagc gttaatgtct ggcttctgat  2280
```

```
aaagcgggcc atgttaaggg cggttttttc ctgtttggtc actgatgcct ccgtgtaagg    2340
gggatttctg ttcatggggg taatgatacc gatgaaacga gagaggatgc tcacgatacg    2400
ggttactgat gatgaacatg cccggttact ggaacgttgt gagggtaaac aactggcggt    2460
atggatgcgg cgggaccaga gaaaaatcac tcagggtcaa tgccagcgct tcgttaatac    2520
agatgtaggt gttccacagg gtagccagca gcatcctgcg atgcagatcc ggaacataat    2580
ggtgcagggc gctgacttcc gcgtttccag actttacgaa acacggaaac cgaagaccat    2640
tcatgttgtt gctcaggtcg cagacgtttt gcagcagcag tcgcttcacg ttcgctcgcg    2700
tatcggtgat tcattctgct aaccagtaag gcaaccccgc cagcctagcc gggtcctcaa    2760
cgacaggagc acgatcatgc gcacccgtgg ccaggaccca acgctgcccg agatgcgccg    2820
cgtgcggctg ctggagatgg cggacgcgat ggatatgttc tgccaagggt tggtttgcgc    2880
attcacagtt ctccgcaaga attgattggc tccaattctt ggagtggtga atccgttagc    2940
gaggtgccgc cggcttccat tcaggtcgag gtggcccggc tccatgcacc gcgacgcaac    3000
gcggggaggc agacaaggta tagggcggcg cctacaatcc atgccaaccc gttccatgtg    3060
ctcgccgagg cggcataaat cgccgtgacg atcagcggtc cagtgatcga agttaggctg    3120
gtaagagccg cgagcgatcc ttgaagctgt ccctgatggt cgtcatctac ctgcctggac    3180
agcatggcct gcaacgcggg catcccgatg ccgccggaag cgagaagaat cataatgggg    3240
aaggccatcc agcctcgcgt cgcgaacgcc agcaagacgt agcccagcgc gtcggccgcc    3300
atgccggcga taatggcctg cttctcgccg aaacgtttgg tggcgggacc agtgacgaag    3360
gcttgagcga gggcgtgcaa gattccgaat accgcaagcg acaggccgat catcgtcgcg    3420
ctccagcgaa agcggtcctc gccgaaaatg acccagagcg ctgccggcac ctgtcctacg    3480
agttgcatga taaagaagac agtcataagt gcggcgacga tagtcatgcc ccgcgcccac    3540
cggaaggagc tgactgggtt gaaggctctc aagggcatcg gtcgacgctc tcccttatgc    3600
gactcctgca ttaggaagca gcccagtagt aggttgaggc cgttgagcac cgccgccgca    3660
aggaatggtg catgcaagga gatggcgccc aacagtcccc cggccacggg gcctgccacc    3720
atacccacgc cgaaacaagc gctcatgagc ccgaagtggc gagcccgatc ttccccatcg    3780
gtgatgtcgg cgatataggc gccagcaacc gcacctgtgg cgccggtgat gccggccacg    3840
atgcgtccgg cgtagaggat tcacaggacg ggtgtggtcg ccatgatcgc gtagtcgata    3900
gtggctccaa gtagcgaagc gagcaggact gggcggcggc caaagcggtc ggacagtgct    3960
ccgagaacgg gtgcgcatag aaattgcatc aacgcatata gcgctagcag cacgccatag    4020
tgactggcga tgctgtcgga atggacgata tcccgcaaga ggcccggcag taccggcata    4080
accaagccta tgcctacagc atccagggtg acggtgccga ggatgacgat gagcgcattg    4140
ttagatttca tacacggtgc ctgactgcgt tagcaattta actgtgataa actaccgcat    4200
taaagcttat cgatgataag ctgtcaaaca tgagaa                              4236
```

<210> SEQ ID NO 6
<211> LENGTH: 4391
<212> TYPE: DNA
<213> ORGANISM: Artificial Sequence
<220> FEATURE:
<223> OTHER INFORMATION: Synthetic construct: pBR-CBST-KPC-2

<400> SEQUENCE: 6

```
ttcttgaaga cgaaagggcc tcgtgatacg cctatttttta taggttaatg tcatgataat      60
aatggtttct tagacgtcag gtggcacttt tcggggaaat gtgcgcggaa cccctatttg     120
```

| | |
|---|---|
| tttattttt taaatacatt caaatatgta tccgctcatg agacaataac cctgataaat | 180 |
| gcttcaataa tattgaaaaa ggaagagtca tatgtcactg tatcgccgtc tagttctgct | 240 |
| gtcttgtctc tcatggccgc tggctggctt ttctgccacc gcgctgacca acctcgtcgc | 300 |
| ggaaccattc gctaaactcg aacaggactt tggcggctcc atcggtgtgt acgcgatgga | 360 |
| taccggctca ggcgcaactg taagttaccg cgctgaggag cgcttcccac tgtgcagctc | 420 |
| attcaagggc tttcttgctg ccgctgtgct ggctcgcagc cagcagcagg ccggcttgct | 480 |
| ggacacaccc atccgttacg gcaaaaatgc gctggttccg tggtcaccca tctcggaaaa | 540 |
| atatctgaca acaggcatga cggtggcgga gctgtccgcg gccgccgtgc aatacagtga | 600 |
| taacgccgcc gccaatttgt tgctgaagga gttgggcggc ccggccgggc tgacggcctt | 660 |
| catgcgctct atcggcgata ccacgttccg tctggaccgc tgggagctgg agctgaactc | 720 |
| cgccatccca ggcgatgcgc gcgataccctc atcgccgcgc gccgtgacgg aaagcttaca | 780 |
| aaaactgaca ctgggctctg cactggctgc gccgcagcgg cagcagtttg ttgattggct | 840 |
| aaagggaaac acgaccggca accaccgcat ccgcgcggcg gtgccggcag actgggcagt | 900 |
| cggagacaaa accggaacct gcggagtgta tggcacggca aatgactatg ccgtcgtctg | 960 |
| gcccactggg cgcgcaccta ttgtgttggc cgtctacacc cgggcgccta acaaggatga | 1020 |
| caagcacagc gaggccgtca tcgccgctgc ggctagactc gcgctcgagg gattgggcgt | 1080 |
| caacgggcag taaggatccc tgtcagacca agttactca tatatacttt agattgattt | 1140 |
| aaaacttcat ttttaattta aaaggatcta ggtgaagatc cttttttgata atctcatgac | 1200 |
| caaaatccct taacgtgagt tttcgttcca ctgagcgtca gaccccgtag aaaagatcaa | 1260 |
| aggatcttct tgagatcctt ttttctgcg cgtaatctgc tgcttgcaaa caaaaaaacc | 1320 |
| accgctacca gcggtggttt gtttgccgga tcaagagcta ccaactcttt ttccgaaggt | 1380 |
| aactggcttc agcagagcgc agataccaaa tactgtcctt ctagtgtagc cgtagttagg | 1440 |
| ccaccacttc aagaactctg tagcaccgcc tacatacctc gctctgctaa tcctgttacc | 1500 |
| agtggctgct gccagtggcg ataagtcgtg tcttaccggg ttggactcaa gacgatagtt | 1560 |
| accggataag gcgcagcggt cgggctgaac ggggggttcg tgcacacagc ccagcttgga | 1620 |
| gcgaacgacc tacaccgaac tgagatacct acagcgtgag ctatgagaaa gcgccacgct | 1680 |
| tcccgaaggg agaaaggcgg acaggtatcc ggtaagcggc agggtcggaa caggagagcg | 1740 |
| cacgagggag cttccagggg gaaacgcctg gtatctttat agtcctgtcg ggtttcgcca | 1800 |
| cctctgactt gagcgtcgat ttttgtgatg ctcgtcaggg gggcggagcc tatggaaaaa | 1860 |
| cgccagcaac gcggcctttt tacggttcct ggccttttgc tggccttttg ctcacatgtt | 1920 |
| ctttcctgcg ttatccctg attctgtgga taaccgtatt accgcctttg agtgagctga | 1980 |
| taccgctcgc cgcagccgaa cgaccgagcg cagcgagtca gtgagcgagg aagcggaaga | 2040 |
| gcgcctgatg cggtattttc tccttacgca tctgtgcggt atttcacacc gcatttggtg | 2100 |
| cactctcagt acaatctgct ctgatgccgc atagttaagc cagtatacac tccgctatcg | 2160 |
| ctacgtgact gggtcatggc tgcgccccga cacccgccaa cacccgctga cgcgccctga | 2220 |
| cgggcttgtc tgctcccggc atccgcttac agacaagctg tgaccgtctc cgggagctgc | 2280 |
| atgtgtcaga ggttttcacc gtcatcaccg aaacgcgcga gcagctgcg gtaaagctca | 2340 |
| tcagcgtggt cgtgaagcga ttcacagatg tctgcctgtt catccgcgtc cagctcgttg | 2400 |
| agtttctcca gaagcgttaa tgtctggctt ctgataaagc gggccatgtt aagggcggtt | 2460 |

| | |
|---|---:|
| ttttcctgtt tggtcactga tgcctccgtg taaggggggat ttctgttcat ggggggtaatg | 2520 |
| ataccgatga aacgagagag gatgctcacg atacgggtta ctgatgatga acatgcccgg | 2580 |
| ttactggaac gttgtgaggg taaacaactg gcggtatgga tgcggcggga ccagagaaaa | 2640 |
| atcactcagg gtcaatgcca gcgcttcgtt aatacagatg taggtgttcc acagggtagc | 2700 |
| cagcagcatc ctgcgatgca gatccggaac ataatggtgc agggcgctga cttccgcgtt | 2760 |
| tccagacttt acgaaacacg gaaaccgaag accattcatg ttgttgctca ggtcgcagac | 2820 |
| gttttgcagc agcagtcgct tcacgttcgc tcgcgtatcg gtgattcatt ctgctaacca | 2880 |
| gtaaggcaac cccgccagcc tagccgggtc ctcaacgaca ggagcacgat catgcgcacc | 2940 |
| cgtggccagg acccaacgct gcccgagatg cgccgcgtgc ggctgctgga gatggcggac | 3000 |
| gcgatggata tgttctgcca agggttggtt tgcgcattca cagttctccg caagaattga | 3060 |
| ttggctccaa ttcttggagt ggtgaatccg ttagcgaggt gccgccggct tccattcagg | 3120 |
| tcgaggtggc ccggctccat gcaccgcgac gcaacgcggg gaggcagaca aggtataggg | 3180 |
| cggcgcctac aatccatgcc aacccgttcc atgtgctcgc cgaggcggca taaatcgccg | 3240 |
| tgacgatcag cggtccagtg atcgaagtta ggctggtaag agccgcgagc gatccttgaa | 3300 |
| gctgtccctg atggtcgtca tctacctgcc tggacagcat ggcctgcaac gcgggcatcc | 3360 |
| cgatgccgcc ggaagcgaga agaatcataa tggggaaggc catccagcct cgcgtcgcga | 3420 |
| acgccagcaa gacgtagccc agcgcgtcgg ccgccatgcc ggcgataatg gcctgcttct | 3480 |
| cgccgaaacg tttggtggcg ggaccagtga cgaaggcttg agcgagggcg tgcaagattc | 3540 |
| cgaataccgc aagcgacagg ccgatcatcg tcgcgctcca gcgaaagcgg tcctcgccga | 3600 |
| aaatgaccca gagcgctgcc ggcacctgtc ctacgagttg catgataaag aagacagtca | 3660 |
| taagtgcggc gacgatagtc atgccccgcg cccaccggaa ggagctgact gggttgaagg | 3720 |
| ctctcaaggg catcggtcga cgctctccct tatgcgactc ctgcattagg aagcagccca | 3780 |
| gtagtaggtt gaggccgttg agcaccgccg ccgcaaggaa tggtgcatgc aaggagatgg | 3840 |
| cgcccaacag tcccccggcc acggggcctg ccaccatacc cacgccgaaa caagcgctca | 3900 |
| tgagcccgaa gtggcgagcc cgatcttccc catcggtgat gtcggcgata taggcgccag | 3960 |
| caaccgcacc tgtggcgccg gtgatgccgg ccacgatgcg tccggcgtag aggattcaca | 4020 |
| ggacgggtgt ggtcgccatg atcgcgtagt cgatagtggc tccaagtagc gaagcgagca | 4080 |
| ggactgggcg gcggccaaag cggtcggaca gtgctccgag aacgggtgcg catagaaatt | 4140 |
| gcatcaacgc atatagcgct agcagcacgc catagtgact ggcgatgctg tcggaatgga | 4200 |
| cgatatcccg caagaggccc ggcagtaccg gcataaccaa gcctatgcct acagcatcca | 4260 |
| gggtgacggt gccgaggatg acgatgagcg cattgttaga tttcatacac ggtgcctgac | 4320 |
| tgcgttagca atttaactgt gataaactac cgcattaaag cttatcgatg ataagctgtc | 4380 |
| aaacatgaga a | 4391 |

<210> SEQ ID NO 7
<211> LENGTH: 4116
<212> TYPE: DNA
<213> ORGANISM: Artificial Sequence
<220> FEATURE:
<223> OTHER INFORMATION: Synthetic construct: pBR-CBST-CTX-M-15

<400> SEQUENCE: 7

| | |
|---|---:|
| ttcttgaaga cgaaagggcc tcgtgatacg cctatttttta taggttaatg tcatgataat | 60 |
| aatggtttct tagacgtcag gtggcacttt tcggggaaat gtgcgcggaa ccctatttg | 120 |

| | | | | |
|---|---|---|---|---|
| tttattttc | taaatacatt | caaatatgta | tccgctcatg agacaataac cctgataaat | 180 |
| gcttcaataa | tattgaaaaa | ggaagagtca | tatggaatct gttaaatcag cgagttgaga | 240 |
| tcaaaaaatc | tgaccttgtt | aactataatc | cgattgcgga aaagcacgtc aatgggacga | 300 |
| tgtcactggc | tgagcttagc | gcggccgcgc | tacagtacag cgataacgtg gcgatgaata | 360 |
| agctgattgc | tcacgttggc | ggcccggcta | gcgtcaccgc gttcgcccga cagctgggag | 420 |
| acgaaacgtt | ccgtctcgac | cgtaccgagc | cgacgttaaa caccgccatt ccgggcgatc | 480 |
| cgcgtgatac | cacttcacct | cgggcaatgg | cgcaaactct gcggaatctg acgctgggta | 540 |
| aagcattggg | cgacagccaa | cgggcgcagc | tggtgacatg gatgaaaggc aataccaccg | 600 |
| gtgcagcgag | cattcaggct | ggactgcctg | cttcctgggt tgtgggggat aaaaccggca | 660 |
| gcggtggcta | tggcaccacc | aacgatatcg | cggtgatctg gccaaaagat cgtgcgccgc | 720 |
| tgattctggt | cacttacttc | acccagcctc | aacctaaggc agaaagccgt cgcgatgtat | 780 |
| tagcgtcggc | ggctaaaatc | gtcaccgacg | gtttgtaagg atccctgtca gaccaagttt | 840 |
| actcatatat | actttagatt | gatttaaaac | ttcattttta atttaaaagg atctaggtga | 900 |
| agatcctttt | tgataatctc | atgaccaaaa | tcccttaacg tgagttttcg ttccactgag | 960 |
| cgtcagaccc | cgtagaaaag | atcaaaggat | cttcttgaga tcctttttt ctgcgcgtaa | 1020 |
| tctgctgctt | gcaaacaaaa | aaaccaccgc | taccagcggt ggtttgtttg ccggatcaag | 1080 |
| agctaccaac | tcttttccg | aaggtaactg | gcttcagcag agcgcagata ccaaatactg | 1140 |
| tccttctagt | gtagccgtag | ttaggccacc | acttcaagaa ctctgtagca ccgcctacat | 1200 |
| acctcgctct | gctaatcctg | ttaccagtgg | ctgctgccag tggcgataag tcgtgtctta | 1260 |
| ccgggttgga | ctcaagacga | tagttaccgg | ataaggcgca gcggtcgggc tgaacggggg | 1320 |
| gttcgtgcac | acagcccagc | ttggagcgaa | cgacctacac cgaactgaga tacctacagc | 1380 |
| gtgagctatg | agaaagcgcc | acgcttcccg | aagggagaaa ggcggacagg tatccggtaa | 1440 |
| gcggcagggt | cggaacagga | gagcgcacga | gggagcttcc agggggaaac gcctggtatc | 1500 |
| tttatagtcc | tgtcgggttt | cgccacctct | gacttgagcg tcgatttttg tgatgctcgt | 1560 |
| caggggggcg | gagcctatgg | aaaaacgcca | gcaacgcggc cttttacgg ttcctggcct | 1620 |
| tttgctggcc | ttttgctcac | atgttctttc | ctgcgttatc ccctgattct gtggataacc | 1680 |
| gtattaccgc | ctttgagtga | gctgataccg | ctcgccgcag ccgaacgacc gagcgcagcg | 1740 |
| agtcagtgag | cgaggaagcg | gaagagcgcc | tgatgcggta ttttctcctt acgcatctgt | 1800 |
| gcggtatttc | acaccgcatt | tggtgcactc | tcagtacaat ctgctctgat gccgcatagt | 1860 |
| taagccagta | tacactccgc | tatcgctacg | tgactgggtc atggctgcgc cccgacaccc | 1920 |
| gccaacaccc | gctgacgcgc | cctgacgggc | ttgtctgctc ccggcatccg cttacagaca | 1980 |
| agctgtgacc | gtctccggga | gctgcatgtg | tcagaggttt tcaccgtcat caccgaaacg | 2040 |
| cgcgaggcag | ctgcggtaaa | gctcatcagc | gtggtcgtga agcgattcac agatgtctgc | 2100 |
| ctgttcatcc | gcgtccagct | cgttgagttt | ctccagaagc gttaatgtct ggcttctgat | 2160 |
| aaagcgggcc | atgttaaggg | cggttttttc | ctgtttggtc actgatgcct ccgtgtaagg | 2220 |
| gggatttctg | ttcatggggg | taatgatacc | gatgaaacga gagaggatgc tcacgatacg | 2280 |
| ggttactgat | gatgaacatg | cccggttact | ggaacgttgt gagggtaaac aactggcggt | 2340 |
| atggatgcgg | cggaccagaa | gaaaaatcac | tcagggtcaa tgccagcgct tcgttaatac | 2400 |
| agatgtaggt | gttccacagg | gtagccagca | gcatcctgcg atgcagatcc ggaacataat | 2460 |

```
ggtgcagggc gctgacttcc gcgtttccag actttacgaa acacggaaac cgaagaccat    2520
tcatgttgtt gctcaggtcg cagacgtttt gcagcagcag tcgcttcacg ttcgctcgcg    2580
tatcggtgat tcattctgct aaccagtaag gcaacccgc cagcctagcc gggtcctcaa     2640
cgacaggagc acgatcatgc gcacccgtgg ccaggaccca acgctgcccg agatgcgccg    2700
cgtgcggctg ctggagatgg cggacgcgat ggatatgttc tgccaagggt tggtttgcgc    2760
attcacagtt ctccgcaaga attgattggc tccaattctt ggagtggtga atccgttagc    2820
gaggtgccgc cggcttccat tcaggtcgag gtggcccggc tccatgcacc gcgacgcaac    2880
gcggggaggc agacaaggta tagggcggcg cctacaatcc atgccaaccc gttccatgtg    2940
ctcgccgagg cggcataaat cgccgtgacg atcagcggtc cagtgatcga agttaggctg    3000
gtaagagccg cgagcgatcc ttgaagctgt ccctgatggt cgtcatctac ctgcctggac    3060
agcatggcct gcaacgcggg catcccgatg ccgccggaag cgagaagaat cataatgggg    3120
aaggccatcc agcctcgcgt cgcgaacgcc agcaagacgt agcccagcgc gtcggccgcc    3180
atgccggcga taatggcctg cttctcgccg aaacgtttgg tggcgggacc agtgacgaag    3240
gcttgagcga gggcgtgcaa gattccgaat accgcaagcg acaggccgat catcgtcgcg    3300
ctccagcgaa agcggtcctc gccgaaaatg acccagagcg ctgccggcac ctgtcctacg    3360
agttgcatga taaagaagac agtcataagt gcggcgacga tagtcatgcc ccgcgcccac    3420
cggaaggagc tgactgggtt gaaggctctc aagggcatcg gtcgacgctc tcccttatgc    3480
gactcctgca ttaggaagca gcccagtagt aggttgaggc cgttgagcac cgccgccgca    3540
aggaatggtg catgcaagga gatggcgccc aacagtcccc cggccacggg gcctgccacc    3600
atacccacgc cgaaacaagc gctcatgagc ccgaagtggc gagcccgatc ttccccatcg    3660
gtgatgtcgg cgatataggc gccagcaacc gcacctgtgg cgccggtgat gccggccacg    3720
atgcgtccgg cgtagaggat tcacaggacg ggtgtggtcg ccatgatcgc gtagtcgata    3780
gtggctccaa gtagcgaagc gagcaggact gggcggcggc caaagcggtc ggacagtgct    3840
ccgagaacgg gtgcgcatag aaattgcatc aacgcatata gcgctagcag cacgccatag    3900
tgactggcga tgctgtcgga atggacgata tcccgcaaga ggcccggcag taccggcata    3960
accaagccta tgcctacagc atccagggtg acggtgccga ggatgacgat gagcgcattg    4020
ttagatttca tacacggtgc ctgactgcgt tagcaattta actgtgataa actaccgcat    4080
taaagcttat cgatgataag ctgtcaaaca tgagaa                              4116

<210> SEQ ID NO 8
<211> LENGTH: 4370
<212> TYPE: DNA
<213> ORGANISM: Artificial Sequence
<220> FEATURE:
<223> OTHER INFORMATION: Synthetic construct: pBR-CBST-SHV-12

<400> SEQUENCE: 8
ttcttgaaga cgaaagggcc tcgtgatacg cctatttta taggttaatg tcatgataat       60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtca tatgcgttat attcgcctgt gtattatctc     240
cctgttagcc accctgccgc tggcggtaca cgccagcccg cagccgcttg agcaaattaa    300
acaaagcgaa agccagctgt cgggccgcgt aggcatgata gaaatggatc tggccagcgg    360
ccgcacgctg accgcctggc gcgccgatga acgctttccc atgatgagca cctttaaagt    420
```

```
agtgctctgc ggcgcagtgc tggcgcgggt ggatgccggt gacgaacagc tggagcgaaa    480
gatccactat cgccagcagg atctggtgga ctactcgccg gtcagcgaaa acaccttgc     540 cgacggcatg acggtcggcg aactctgcgc cgccgccatt accatgagcg ataacagcgc    600
cgccaatctg ctgctggcca ccgtcggcgg ccccgcagga ttgactgcct ttttgcgcca    660
gatcggcgac aacgtcaccc gccttgaccg ctgggaaacg gaactgaatg aggcgcttcc    720
cggcgacgcc cgcgacacca ctaccccggc cagcatggcc gcgaccctgc gcaagctgct    780
gaccagccag cgtctgagcg cccgttcgca acggcagctg ctgcagtgga tggtggacga    840
tcgggtcgcc ggaccgttga tccgctccgt gctgccggcg ggctggttta tcgccgataa    900
gaccggagct agcaagcggg gtgcgcgcgg gattgtcgcc ctgcttggcc gaataacaa     960 agcagagcgc attgtggtga tttatctgcg ggatacccg gcgagcatgg ccgagcgaaa    1020
tcagcaaatc gccgggatcg gcgcggcgct gatcgagcac tggcaacgct aaggatccct   1080
gtcagaccaa gtttactcat atatacttta gattgattta aaacttcatt tttaatttaa   1140
aaggatctag gtgaagatcc ttttttgataa tctcatgacc aaaatccctt aacgtgagtt   1200
ttcgttccac tgagcgtcag accccgtaga aaagatcaaa ggatcttctt gagatccttt   1260
ttttctgcgc gtaatctgct gcttgcaaac aaaaaaacca ccgctaccag cggtggtttg   1320
tttgccggat caagagctac caactctttt tccgaaggta actggcttca gcagagcgca   1380
gataccaaat actgtccttc tagtgtagcc gtagttaggc caccacttca gaactctgt    1440 agcaccgcct acatacctcg ctctgctaat cctgttacca gtggctgctg ccagtggcga   1500
taagtcgtgt cttaccgggt tggactcaag acgatagtta ccggataagg cgcagcggtc   1560
gggctgaacg gggggttcgt gcacacagcc cagcttggag cgaacgacct acaccgaact   1620
gagataccta cagcgtgagc tatgagaaag cgccacgctt cccgaaggga gaaaggcgga   1680
caggtatccg gtaagcggca gggtcggaac aggagagcgc acgagggagc ttccaggggg   1740
aaacgcctgg tatctttata gtcctgtcgg gtttcgccac ctctgacttg agcgtcgatt   1800
tttgtgatgc tcgtcagggg ggcggagcct atggaaaaac gccagcaacg cggcctttt    1860 acggttcctg gccttttgct ggccttttgc tcacatgttc tttcctgcgt tatcccctga   1920
ttctgtggat aaccgtatta ccgcctttga gtgagctgat accgctcgcc gcagccgaac   1980
gaccgagcgc agcgagtcag tgagcgagga agcggaagag cgcctgatgc ggtattttct   2040
ccttacgcat ctgtgcggta tttcacaccg catttggtgc actctcagta caatctgctc   2100
tgatgccgca tagttaagcc agtatacact ccgctatcgc tacgtgactg ggtcatggct   2160
gcgccccgac acccgccaac accgctgac gcgccctgac gggcttgtct gctcccggca    2220
tccgcttaca gacaagctgt gaccgtctcc gggagctgca tgtgtcagag gttttcaccg   2280
tcatcaccga aacgcgcgag gcagctgcgg taaagctcat cagcgtggtc gtgaagcgat   2340
tcacagatgt ctgcctgttc atccgcgtcc agctcgttga gtttctccag aagcgttaat   2400
gtctggcttc tgataaagcg ggccatgtta agggcggttt ttcctgtttt ggtcactgat   2460
gcctccgtgt aagggggatt tctgttcatg ggggtaatga taccgatgaa acgagagagg   2520
atgctcacga tacgggttac tgatgatgaa catgcccggt tactggaacg ttgtgagggt   2580
aaacaactgg cggtatggat gcggcgggac cagagaaaaa tcactcaggg tcaatgccag   2640
cgcttcgtta atacagatgt aggtgttcca cagggtagcc agcagcatcc tgcgatgcag   2700
atccggaaca taatggtgca gggcgctgac ttccgcgttt ccagacttta cgaaacacgg   2760
```

```
aaaccgaaga ccattcatgt tgttgctcag gtcgcagacg ttttgcagca gcagtcgctt    2820
cacgttcgct cgcgtatcgg tgattcattc tgctaaccag taaggcaacc ccgccagcct    2880
agccgggtcc tcaacgacag gagcacgatc atgcgcaccc gtggccagga cccaacgctg    2940
cccgagatgc gccgcgtgcg gctgctggag atggcggacg cgatggatat gttctgccaa    3000
gggttggttt gcgcattcac agttctccgc aagaattgat tggctccaat tcttggagtg    3060
gtgaatccgt tagcgaggtg ccgccggctt ccattcaggt cgaggtggcc cggctccatg    3120
caccgcgacg caacgcgggg aggcagacaa ggtatagggc ggcgcctaca atccatgcca    3180
acccgttcca tgtgctcgcc gaggcggcat aaatcgccgt gacgatcagc ggtccagtga    3240
tcgaagttag gctggtaaga gccgcgagcg atccttgaag ctgtccctga tggtcgtcat    3300
ctacctgcct ggacagcatg gcctgcaacg cgggcatccc gatgccgccg gaagcgagaa    3360
gaatcataat ggggaaggcc atccagcctc gcgtcgcgaa cgccagcaag acgtagccca    3420
gcgcgtcggc cgccatgccg gcgataatgg cctgcttctc gccgaaacgt ttggtggcgg    3480
gaccagtgac gaaggcttga gcgagggcgt gcaagattcc gaataccgca agcgacaggc    3540
cgatcatcgt cgcgctccag cgaaagcggt cctcgccgaa aatgacccag agcgctgccg    3600
gcacctgtcc tacgagttgc atgataaaga agacagtcat aagtgcggcg acgatagtca    3660
tgccccgcgc ccaccggaag gagctgactg ggttgaaggc tctcaagggc atcggtcgac    3720
gctctccctt atgcgactcc tgcattagga agcagcccag tagtaggttg aggccgttga    3780
gcaccgccgc cgcaaggaat ggtgcatgca aggagatggc gcccaacagt cccccggcca    3840
cggggcctgc caccatacccc acgccgaaac aagcgctcat gagcccgaag tggcgagccc    3900
gatcttcccc atcggtgatg tcggcgatat aggcgccagc aaccgcacct gtggcgccgg    3960
tgatgccggc cacgatgcgt ccggcgtaga ggattcacag gacgggtgtg gtcgccatga    4020
tcgcgtagtc gatagtggct ccaagtagcg aagcgagcag gactgggcgg cggccaaagc    4080
ggtcggacag tgctccgaga acgggtgcgc atagaaattg catcaacgca tatagcgcta    4140
gcagcacgcc atagtgactg gcgatgctgt cggaatggac gatatcccgc aagaggcccg    4200
gcagtaccgg cataaccaag cctatgccta cagcatccag ggtgacggtg ccgaggatga    4260
cgatgagcgc attgttagat ttcatacacg gtgcctgact gcgttagcaa tttaactgtg    4320
ataaactacc gcattaaagc ttatcgatga taagctgtca acatgagaa    4370
```

<210> SEQ ID NO 9
<211> LENGTH: 4655
<212> TYPE: DNA
<213> ORGANISM: Artificial Sequence
<220> FEATURE:
<223> OTHER INFORMATION: Synthetic construct: pBR-CBST-P99

<400> SEQUENCE: 9

```
ttcttgaaga cgaaagggcc tcgtgatacg cctatttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtca tatgatgaga aaatcccttt gctgcgccct     240
gctgctcggc atctcttgct ctgctctcgc cacgccagtg tcagaaaaac agctggcgga     300
ggtggtcgcg aatacgatta ccccgctgat gaaagcccag tctgttccag gcatggcggt     360
ggccgttatt tatcagggaa aaccgcacta ttacacattt ggcaaggccg atatcgcggc     420
gaataaaccc gttacgcctc agaccctgtt cgagctgggt tctataagta aaaccttcac     480
```

```
cggcgtttta ggtggggatg ccattgctcg cggtgaaatt tcgctggacg atgcggtgac      540
cagatactgg ccacagctga cgggcaagca gtggcagggt attcgtatgc tggatctcgc      600
cacctacacc gctggcggcc tgccgctaca ggtaccggat gaggtcacgg ataacgcctc      660
cctgctgcgc ttttatcaaa actggcagcc gcagtggaag cctggcacaa cgcgtcttta      720
cgccaacgcc agcatcggtc tttttggtgc gctggcggtc aaaccttctg catgcccta       780 tgagcaggcc atgacgacgc gggtccttaa gccgctcaag ctggaccata cctggattaa      840
cgtgccgaaa gcggaagagg cgcattacgc ctggggctat cgtgacggta agcggtgcg       900 cgtttcgccg ggtatgctgg atgcacaagc ctatggcgtg aaaaccaacg tgcaggatat      960
ggcgaactgg gtcatggcaa acatggcgcc ggagaacgtt gctgatgcct cacttaagca     1020
gggcatcgcg ctggcgcagt cgcgctactg gcgtatcggg tcaatgtatc agggtctggg     1080
ctgggagatg ctcaactggc ccgtggaggc caacacggtg gtcgagggca gcacagtaa      1140 ggtagcactg gcgccgttgc ccgtggcaga agtgaatcca ccggctcccc cggtcaaagc     1200
gtcctgggtc cataaaacgg gctctactgg cgggtttggc agctacgtgg cctttattcc     1260
tgaaaagcag atcggtattg tgatgctcgc gaatacaagc tatccgaacc cggcacgcgt     1320
tgaggcggca taccatatcc tcgaggcgct acagtaagga tccctgtcag accaagttta     1380
ctcatatata ctttagattg atttaaaact tcatttttaa tttaaaagga tctaggtgaa     1440 gatcctttt gataatctca tgaccaaaat cccttaacgt gagttttcgt tccactgagc      1500
gtcagacccc gtagaaaaga tcaaaggatc ttcttgagat ccttttttc tgcgcgtaat      1560 ctgctgcttg caaacaaaaa accaccgct accagcggtg gtttgtttgc cggatcaaga     1620
gctaccaact cttttccga aggtaactgg cttcagcaga gcgcagatac caaatactgt      1680
ccttctagtg tagccgtagt taggccacca cttcaagaac tctgtagcac cgcctacata     1740
cctcgctctg ctaatcctgt taccagtggc tgctgccagt ggcgataagt cgtgtcttac     1800
cgggttggac tcaagacgat agttaccgga taaggcgcag cggtcgggct gaacggggg      1860 ttcgtgcaca cagcccagct tggagcgaac gacctacacc gaactgagat acctacagcg     1920
tgagctatga aaagcgcca cgcttcccga agggagaaag gcggacaggt atccggtaag     1980
cggcagggtc ggaacaggag agcgcacgag ggagcttcca gggggaaacg cctggtatct     2040
ttatagtcct gtcgggtttc gccacctctg acttgagcgt cgatttttgt gatgctcgtc     2100
aggggggcgg agcctatgga aaacgccag caacgcggcc ttttacggt tcctggcctt      2160 ttgctggcct tttgctcaca tgttctttcc tgcgttatcc cctgattctg tggataaccg     2220
tattaccgcc tttgagtgag ctgataccgc tcgccgcagc cgaacgaccg agcgcagcga     2280
gtcagtgagc gaggaagcgg aagagcgcct gatgcggtat tttctcctta cgcatctgtg     2340
cggtatttca caccgcattt ggtgcactct cagtacaatc tgctctgatg ccgcatagtt     2400
aagccagtat acactccgct atcgctacgt gactgggtca tggctgcgcc ccgacacccg     2460
ccaacacccg ctgacgcgcc ctgacgggct tgtctgctcc cggcatccgc ttacagacaa     2520
gctgtgaccg tctccgggag ctgcatgtgt cagaggtttt caccgtcatc accgaaacgc     2580
gcgaggcagc tgcggtaaag ctcatcagcg tggtcgtgaa gcgattcaca gatgtctgcc     2640
tgttcatccg cgtccagctc gttgagtttc tccagaagcg ttaatgtctg gcttctgata     2700
aagcgggcca tgttaaggc ggttttttcc tgtttggtca ctgatgcctc cgtgtaaggg     2760
ggatttctgt tcatgggggt aatgataccg atgaaacgag agaggatgct cacgatacgg     2820
```

| | |
|---|---|
| gttactgatg atgaacatgc ccggttactg aacgttgtg agggtaaaca actggcggta | 2880 |
| tggatgcggc gggaccagag aaaaatcact cagggtcaat gccagcgctt cgttaataca | 2940 |
| gatgtaggtg ttccacaggg tagccagcag catcctgcga tgcagatccg aacataatg | 3000 |
| gtgcagggcg ctgacttccg cgtttccaga ctttacgaaa cacggaaacc gaagaccatt | 3060 |
| catgttgttg ctcaggtcgc agacgttttg cagcagcagt cgcttcacgt tcgctcgcgt | 3120 |
| atcggtgatt cattctgcta accagtaagg caaccccgcc agcctagccg ggtcctcaac | 3180 |
| gacaggagca cgatcatgcg caccgtggc caggacccaa cgctgcccga gatgcgccgc | 3240 |
| gtgcggctgc tggagatggc ggacgcgatg gatatgttct gccaagggtt ggtttgcgca | 3300 |
| ttcacagttc tccgcaagaa ttgattggct ccaattcttg gagtggtgaa tccgttagcg | 3360 |
| aggtgccgcc ggcttccatt caggtcgagg tggcccggct ccatgcaccg cgacgcaacg | 3420 |
| cggggaggca gacaaggtat agggcggcgc ctacaatcca tgccaacccg ttccatgtgc | 3480 |
| tcgccgaggc ggcataaatc gccgtgacga tcagcggtcc agtgatcgaa gttaggctgg | 3540 |
| taagagccgc gagcgatcct tgaagctgtc cctgatggtc gtcatctacc tgcctggaca | 3600 |
| gcatggcctg caacgcgggc atcccgatgc cgccggaagc gagaagaatc ataatgggga | 3660 |
| aggccatcca gcctcgcgtc gcgaacgcca gcaagacgta gcccagcgcg tcggccgcca | 3720 |
| tgccggcgat aatggcctgc ttctcgccga aacgtttggt ggcgggacca gtgacgaagg | 3780 |
| cttgagcgag ggcgtgcaag attccgaata ccgcaagcga caggccgatc atcgtcgcgc | 3840 |
| tccagcgaaa gcggtcctcg ccgaaaatga cccagagcgc tgccggcacc tgtcctacga | 3900 |
| gttgcatgat aaagaagaca gtcataagtg cggcgacgat agtcatgccc cgcgcccacc | 3960 |
| ggaaggagct gactgggttg aaggctctca agggcatcgg tcgacgctct cccttatgcg | 4020 |
| actcctgcat taggaagcag cccagtagta ggttgaggcc gttgagcacc gccgccgcaa | 4080 |
| ggaatggtgc atgcaaggag atggcgccca acagtccccc ggccacgggg cctgccacca | 4140 |
| tacccacgcc gaaacaagcg ctcatgagcc cgaagtggcg agcccgatct tccccatcgg | 4200 |
| tgatgtcggc gatataggcg ccagcaaccg cacctgtggc gccggtgatg ccggcacga | 4260 |
| tgcgtccggc gtagaggatt cacaggacgg gtgtggtcgc catgatcgcg tagtcgatag | 4320 |
| tggctccaag tagcgaagcg agcaggactg ggcggcggcc aaagcggtcg acagtgctc | 4380 |
| cgagaacggg tgcgcataga aattgcatca acgcatatag cgctagcagc acgccatagt | 4440 |
| gactggcgat gctgtcggaa tggacgatat cccgcaagag gcccggcagt accggcataa | 4500 |
| ccaagcctat gcctacagca tccagggtga cggtgccgag gatgacgatg agcgcattgt | 4560 |
| tagatttcat acacggtgcc tgactgcgtt agcaatttaa ctgtgataaa ctaccgcatt | 4620 |
| aaagcttatc gatgataagc tgtcaaacat gagaa | 4655 |

<210> SEQ ID NO 10
<211> LENGTH: 4337
<212> TYPE: DNA
<213> ORGANISM: Artificial Sequence
<220> FEATURE:
<223> OTHER INFORMATION: Synthetic construct: pBR-CBST-OXA-15

<400> SEQUENCE: 10

| | |
|---|---|
| ttcttgaaga cgaaagggcc tcgtgatacg cctatttta taggttaatg tcatgataat | 60 |
| aatggtttct tagacgtcag gtggcacttt tcggggaaat gtgcgcggaa cccctatttg | 120 |
| tttatttttc taaatacatt caaatatgta tccgctcatg agacaataac cctgataaat | 180 |
| gcttcaataa tattgaaaaa ggaagagtca tatggcaatc cgaatcttcg cgatactttt | 240 |

```
ctccattttt tctcttgcca ctttcgcgca tgcgcaagaa ggcacgctag aacgttctga    300
ctggaggaag tttttcagcg aatttcaagc caaaggcacg atagttgtgg cagacgaacg    360
ccaagcggat cgtgccatgt tggtttttga tcctgtgcga tcgaagaaac gctactcgcc    420
tgcatcgaca ttcaagatac ctcatacact ttttgcactt gatgcaggcg ctgttcgtga    480
tgagttccag atttttcgat gggacggcgt taacaggggc tttgcaggcc acaatcaaga    540
ccaagatttg cgatcagcaa tgcggaattc tactgtttgg gtgtatgagc tatttgcaaa    600
ggaaattggt gatgacaaag ctcggcgcta tttgaagaaa atcgactatg caacgccgg     660 tccttcgaca agtaatggcg attactggat agaaggcagc cttgcaatct cggcgcagga    720
gcaaattgca tttctcagga agctctatcg taacgagctg ccctttcggg tagaacatca    780
gcgcttggtc aaggatctca tgattgtgga agccggtcgc aactggatac tgcgtgcaaa    840
gacgggctgg gaaggccgta tgggttggtg ggtaggatgg gttgagtggc cgactggctc    900
cgtattcttc gcactgaata ttgatacgcc aaacagaatg gatgatcttt tcaagaggga    960
ggcaatcgtg cgggcaatcc ttcgctctat tgaagcgtta ccgcccaacc cggcagtcaa   1020
ctcggacgct gcgcgataag gatccctgtc agaccaagtt tactcatata tactttagat   1080
tgatttaaaa cttcattttt aatttaaaag gatctaggtg aagatccttt ttgataatct   1140
catgaccaaa atcccttaac gtgagttttc gttccactga gcgtcagacc ccgtagaaaa   1200
gatcaaagga tcttcttgag atcctttttt tctgcgcgta atctgctgct tgcaaacaaa   1260
aaaaccaccg ctaccagcgg tggtttgttt gccggatcaa gagctaccaa ctcttttcc    1320 gaaggtaact ggcttcagca gagcgcagat accaaatact gtccttctag tgtagccgta   1380
gttaggccac cacttcaaga actctgtagc accgcctaca tacctcgctc tgctaatcct   1440
gttaccagtg gctgctgcca gtggcgataa gtcgtgtctt accgggttgg actcaagacg   1500
atagttaccg gataaggcgc agcggtcggg ctgaacgggg ggttcgtgca cacagcccag   1560
cttggagcga acgacctaca ccgaactgag atacctacag cgtgagctat gagaaagcgc   1620
cacgcttccc gaagggagaa aggcggacag gtatccggta agcggcaggg tcggaacagg   1680
agagcgcacg agggagcttc caggggggaaa cgcctggtat ctttatagtc ctgtcgggtt   1740
tcgccacctc tgacttgagc gtcgattttt gtgatgctcg tcagggggggc ggagcctatg   1800 gaaaaacgcc agcaacgcgg ccttttttacg gttcctggcc ttttgctggc cttttgctca   1860
catgttcttt cctgcgttat cccctgattc tgtggataac cgtattaccg cctttgagtg   1920
agctgatacc gctcgccgca gccgaacgac cgagcgcagc gagtcagtga gcgaggaagc   1980
ggaagagcgc ctgatgcggt attttctcct tacgcatctg tgcggtattt cacaccgcat   2040
ttggtgcact ctcagtacaa tctgctctga tgccgcatag ttaagccagt atacactccg   2100
ctatcgctac gtgactgggt catggctgcg ccccgacacc cgccaacacc cgctgacgcg   2160
ccctgacggg cttgtctgct cccggcatcc gcttacagac aagctgtgac cgtctccggg   2220
agctgcatgt gtcagaggtt ttcaccgtca tcaccgaaac gcgcgaggca gctgcggtaa   2280
agctcatcag cgtggtcgtg aagcgattca cagatgtctg cctgttcatc cgcgtccagc   2340
tcgttgagtt ctccagaagc gttaatgtc tggcttctga taaagcgggc catgttaagg   2400
```

```
gcggttttttt cctgtttggt cactgatgcc tccgtgtaag ggggatttct gttcatgggg    2460
gtaatgatac cgatgaaacg agagaggatg ctcacgatac gggttactga tgatgaacat    2520
gcccggttac tggaacgttg tgagggtaaa caactggcgg tatggatgcg gcgggaccag    2580
agaaaaatca ctcagggtca atgccagcgc ttcgttaata cagatgtagg tgttccacag    2640
ggtagccagc agcatcctgc gatgcagatc cggaacataa tggtgcaggg cgctgacttc    2700 cgcgttttcca gactttacga aacacggaaa ccgaagacca ttcatgttgt tgctcaggtc    2760
gcagacgttt tgcagcagca gtcgcttcac gttcgctcgc gtatcggtga ttcattctgc    2820
taaccagtaa ggcaaccccg ccagcctagc cgggtcctca acgacaggag cacgatcatg    2880
cgcacccgtg gccaggaccc aacgctgccc gagatgcgcc gcgtgcggct gctggagatg    2940
gcggacgcga tggatatgtt ctgccaaggg ttggtttgcg cattcacagt tctccgcaag    3000
aattgattgg ctccaattct tggagtggtg aatccgttag cgaggtgccg ccggcttcca    3060
ttcaggtcga ggtggcccgg ctccatgcac cgcgacgcaa cgcggggagg cagacaaggt    3120
atagggcggc gcctacaatc catgccaacc cgttccatgt gctcgccgag gcggcataaa    3180
tcgccgtgac gatcagcggt ccagtgatcg aagttaggct ggtaagagcc gcgagcgatc    3240
cttgaagctg tccctgatgg tcgtcatcta cctgcctgga cagcatggcc tgcaacgcgg    3300
gcatcccgat gccgccggaa gcgagaagaa tcataatggg gaaggccatc cagcctcgcg    3360
tcgcgaacgc cagcaagacg tagcccagcg cgtcggccgc catgccggcg ataatggcct    3420
gcttctcgcc gaaacgtttg gtggcgggac cagtgacgaa ggcttgagcg agggcgtgca    3480
agattccgaa taccgcaagc gacaggccga tcatcgtcgc gctccagcga aagcggtcct    3540
cgccgaaaat gacccagagc gctgccggca cctgtcctac gagttgcatg ataaagaaga    3600
cagtcataag tgcggcgacg atagtcatgc cccgcgccca ccggaaggag ctgactgggt    3660
tgaaggctct caagggcatc ggtcgacgct ctcccttatg cgactcctgc attaggaagc    3720
agcccagtag taggttgagg ccgttgagca ccgccgccgc aaggaatggt gcatgcaagg    3780
agatggcgcc caacagtccc ccggccacgg ggcctgccac catacccacg ccgaaacaag    3840
cgctcatgag cccgaagtgg cgagcccgat cttccccatc ggtgatgtcg gcgatatagg    3900
cgccagcaac cgcacctgtg gcgccggtga tgccggccac gatgcgtccg gcgtagagga    3960
ttcacaggac gggtgtggtc gccatgatcg cgtagtcgat agtggctcca agtagcgaag    4020
cgagcaggac tgggcggcgg ccaaagcggt cggacagtgc tccgagaacg ggtgcgcata    4080
gaaattgcat caacgcatat agcgctagca gcacgccata tgactggcg atgctgtcgg    4140 aatggacgat atcccgcaag aggcccggca gtaccggcat aaccaagcct atgcctacag    4200
catccagggt gacggtgccg aggatgacga tgagcgcatt gttagatttc atacacggtg    4260
cctgactgcg ttagcaattt aactgtgata aactaccgca ttaaagctta tcgatgataa    4320
gctgtcaaac atgagaa                                                   4337
```